United States Patent
Reglos et al.

(10) Patent No.: US 9,084,591 B2
(45) Date of Patent: Jul. 21, 2015

(54) RETRACTOR

(71) Applicant: NeuroStructures, LLC, Irvine, CA (US)

(72) Inventors: Joey Reglos, Lake Forest, CA (US); Moti Altarac, Irvine, CA (US); John Fredrick Stephani, Soquel, CA (US)

(73) Assignee: NeuroStructures, Inc., Irvine, CA (US)

( * ) Notice: Subject to any disclaimer, the term of this patent is extended or adjusted under 35 U.S.C. 154(b) by 94 days.

(21) Appl. No.: 13/734,317

(22) Filed: Jan. 4, 2013

(65) Prior Publication Data

US 2014/0114137 A1 Apr. 24, 2014

Related U.S. Application Data

(60) Provisional application No. 61/717,202, filed on Oct. 23, 2012.

(51) Int. Cl.
 *A61B 1/32* (2006.01)
 *A61B 17/02* (2006.01)
 *A61B 17/34* (2006.01)

(52) U.S. Cl.
 CPC ......... *A61B 17/0206* (2013.01); *A61B 17/0293* (2013.01); *A61B 17/3421* (2013.01)

(58) Field of Classification Search
 CPC ........... A61B 17/0293; A61B 17/0206; A61B 17/3421
 USPC ............ 600/201–246; 606/86 R, 86 A, 86 B; 384/53
 See application file for complete search history.

(56) References Cited

U.S. PATENT DOCUMENTS

| | | | |
|---|---|---|---|
| 835,968 A | | 11/1906 | Mennes |
| 1,400,616 A | | 12/1921 | McCrory et al. |
| 2,144,156 A | * | 1/1939 | Johnson ............................. 464/7 |
| 3,353,875 A | * | 11/1967 | Karge .............................. 384/45 |
| 3,591,906 A | * | 7/1971 | Leiber ........................ 29/898.03 |
| 3,659,909 A | * | 5/1972 | Egbert ............................. 384/56 |
| 3,941,060 A | * | 3/1976 | Morsbach ..................... 104/247 |
| 4,010,741 A | | 3/1977 | Gauthier |
| 4,562,832 A | | 1/1986 | Wilder et al. |
| 4,747,394 A | | 5/1988 | Watanabe |

(Continued)

FOREIGN PATENT DOCUMENTS

| DE | 8704901 U1 | 7/1987 |
|---|---|---|
| EP | 428567 A1 | 5/1991 |

(Continued)

OTHER PUBLICATIONS

Nagoya Screw Mfg. Co. Ltd, JP 11262491 A, Sep. 28, 1999, Machine translation performed on Aug. 30, 2013, pp. 1-13.*

*Primary Examiner* — Eduardo C Robert
*Assistant Examiner* — Jacqueline Johanas
(74) *Attorney, Agent, or Firm* — Rimas Lukas

(57) ABSTRACT

The retractor system for use in spinal surgery and other types of surgical procedures that is a simple and efficient solution for minimally invasive access to thoracolumbar spine is disclosed. The fully customizable design allows the surgeon to independently angle the retractor blades and expand the retractor in both cephalad-caudal and medial-lateral directions. With an offering of a range of blade lengths, access can be tailored to the patient's anatomy. The retractor system provides versatility and control ensuring minimal tissue trauma.

8 Claims, 43 Drawing Sheets

(56) References Cited

U.S. PATENT DOCUMENTS

| | | | |
|---|---|---|---|
| 4,817,587 A | 4/1989 | Janese | |
| 4,867,141 A | 9/1989 | Nakada et al. | |
| 4,898,566 A * | 2/1990 | Hakansson | 464/167 |
| 4,932,395 A | 6/1990 | Mehdizadeh | |
| 5,052,373 A | 10/1991 | Michelson | |
| 5,067,477 A * | 11/1991 | Santangelo | 600/222 |
| 5,156,463 A * | 10/1992 | Zaguroli, Jr. | 384/53 |
| 5,167,223 A * | 12/1992 | Koros et al. | 600/232 |
| 5,284,129 A | 2/1994 | Agbodoe et al. | |
| 5,320,374 A * | 6/1994 | Farris et al. | 280/276 |
| 5,363,841 A | 11/1994 | Coker | |
| 5,372,597 A * | 12/1994 | Hotchkiss et al. | 606/56 |
| 5,429,121 A | 7/1995 | Gadelius | |
| D361,381 S | 8/1995 | Koros et al. | |
| 5,512,038 A | 4/1996 | O'neal et al. | |
| 5,569,300 A | 10/1996 | Redmon | |
| 5,573,226 A * | 11/1996 | Smith | 254/395 |
| 5,667,481 A * | 9/1997 | Villalta et al. | 600/224 |
| 5,688,223 A | 11/1997 | Rosendahl | |
| 5,728,046 A | 3/1998 | Mayer et al. | |
| 5,741,261 A | 4/1998 | Moskovitz et al. | |
| 5,769,781 A | 6/1998 | Chappuis | |
| 5,779,629 A | 7/1998 | Hohlen | |
| 5,785,647 A | 7/1998 | Tompkins et al. | |
| 5,785,648 A | 7/1998 | Min | |
| 5,792,044 A | 8/1998 | Foley et al. | |
| 5,885,291 A | 3/1999 | Moskovitz et al. | |
| 5,885,292 A | 3/1999 | Moskovitz et al. | |
| 5,891,147 A | 4/1999 | Moskovitz et al. | |
| 5,902,233 A | 5/1999 | Farley et al. | |
| 5,928,139 A | 7/1999 | Koros et al. | |
| 5,928,199 A | 7/1999 | Nakagami | |
| 5,931,777 A | 8/1999 | Sava | |
| 5,944,658 A | 8/1999 | Koros et al. | |
| 5,984,867 A | 11/1999 | Deckman et al. | |
| 6,007,487 A | 12/1999 | Foley et al. | |
| 6,074,343 A | 6/2000 | Nathanson et al. | |
| 6,083,154 A | 7/2000 | Liu et al. | |
| 6,102,852 A | 8/2000 | Liu | |
| 6,102,928 A | 8/2000 | Bonutti | |
| 6,113,273 A * | 9/2000 | Eberle et al. | 384/40 |
| 6,139,493 A | 10/2000 | Koros et al. | |
| 6,159,179 A | 12/2000 | Simonson | |
| 6,189,843 B1 * | 2/2001 | Pfister | 248/161 |
| 6,206,826 B1 | 3/2001 | Mathews et al. | |
| 6,214,001 B1 | 4/2001 | Casscells et al. | |
| 6,214,004 B1 | 4/2001 | Coker | |
| 6,224,597 B1 | 5/2001 | Coker | |
| 6,228,022 B1 | 5/2001 | Friesem et al. | |
| 6,296,609 B1 | 10/2001 | Brau | |
| 6,354,995 B1 | 3/2002 | Hoftman et al. | |
| 6,361,492 B1 | 3/2002 | Santilli | |
| 6,416,465 B2 | 7/2002 | Brau | |
| 6,431,025 B1 | 8/2002 | Koros et al. | |
| 6,505,969 B2 * | 1/2003 | Senger | 384/56 |
| 6,530,883 B2 | 3/2003 | Bookwalter et al. | |
| 6,530,926 B1 | 3/2003 | Davison | |
| 6,679,833 B2 | 1/2004 | Smith et al. | |
| 6,723,043 B2 | 4/2004 | Kleeman et al. | |
| 6,746,396 B1 * | 6/2004 | Segermark et al. | 600/233 |
| 6,800,084 B2 | 10/2004 | Davison et al. | |
| 6,811,558 B2 | 11/2004 | Davison et al. | |
| 6,821,243 B2 | 11/2004 | Pagliuca et al. | |
| 6,837,891 B2 | 1/2005 | Davison et al. | |
| 6,858,032 B2 * | 2/2005 | Chow et al. | 606/80 |
| 6,916,330 B2 | 7/2005 | Simonson | |
| 6,929,606 B2 | 8/2005 | Ritland | |
| 6,942,417 B2 * | 9/2005 | Schwarzbich | 403/109.1 |
| 6,951,538 B2 | 10/2005 | Ritland | |
| 7,001,397 B2 | 2/2006 | Davison et al. | |
| 7,008,431 B2 | 3/2006 | Simonson | |
| 7,033,369 B2 | 4/2006 | Davison et al. | |
| 7,056,321 B2 | 6/2006 | Pagliuca et al. | |
| 7,074,226 B2 | 7/2006 | Roehm, III et al. | |
| 7,079,883 B2 | 7/2006 | Marino et al. | |
| 7,104,692 B1 * | 9/2006 | Lu | 384/49 |
| 7,156,805 B2 | 1/2007 | Thalgott et al. | |
| 7,179,225 B2 | 2/2007 | Shluzas et al. | |
| 7,210,485 B2 | 5/2007 | Zinkel | |
| 7,261,688 B2 | 8/2007 | Smith et al. | |
| 7,270,632 B2 | 9/2007 | Santilli | |
| 7,276,024 B1 | 10/2007 | Royse et al. | |
| 7,407,483 B2 | 8/2008 | Perez-Cruet et al. | |
| 7,427,264 B2 | 9/2008 | Nowitzke et al. | |
| 7,497,014 B2 * | 3/2009 | Muller | 29/898.03 |
| 7,537,565 B2 | 5/2009 | Bass | |
| 7,582,058 B1 | 9/2009 | Miles et al. | |
| 7,691,057 B2 | 4/2010 | Miles et al. | |
| 7,758,501 B2 * | 7/2010 | Frasier et al. | 600/233 |
| 7,850,608 B2 * | 12/2010 | Hamada | 600/219 |
| 8,038,611 B2 * | 10/2011 | Raymond et al. | 600/231 |
| 8,052,098 B1 * | 11/2011 | Kowaleski | 248/49 |
| 8,206,293 B2 | 6/2012 | Reglos et al. | |
| 8,211,012 B2 * | 7/2012 | Wing et al. | 600/215 |
| 8,226,554 B2 * | 7/2012 | McBride et al. | 600/219 |
| 8,517,935 B2 * | 8/2013 | Marchek et al. | 600/233 |
| 8,882,661 B2 * | 11/2014 | Hutton et al. | 600/201 |
| 2002/0077632 A1 | 6/2002 | Tsou | |
| 2003/0073998 A1 | 4/2003 | Pagliuca et al. | |
| 2003/0139648 A1 | 7/2003 | Foley et al. | |
| 2003/0167059 A1 | 9/2003 | Young | |
| 2003/0187431 A1 | 10/2003 | Simonson | |
| 2003/0191371 A1 | 10/2003 | Smith et al. | |
| 2003/0236447 A1 | 12/2003 | Ritland | |
| 2004/0024291 A1 | 2/2004 | Zinkel | |
| 2004/0215199 A1 | 10/2004 | Zinkel | |
| 2004/0230191 A1 | 11/2004 | Frey et al. | |
| 2005/0004593 A1 | 1/2005 | Simonson | |
| 2005/0021030 A1 | 1/2005 | Pagliuca et al. | |
| 2005/0038440 A1 | 2/2005 | Larson et al. | |
| 2005/0070919 A1 | 3/2005 | Lieberman | |
| 2005/0080320 A1 | 4/2005 | Lee et al. | |
| 2005/0080418 A1 | 4/2005 | Simonson et al. | |
| 2005/0137461 A1 | 6/2005 | Marchek et al. | |
| 2005/0149035 A1 | 7/2005 | Pimenta et al. | |
| 2005/0154395 A1 | 7/2005 | Robbins et al. | |
| 2005/0159650 A1 | 7/2005 | Raymond et al. | |
| 2005/0159651 A1 | 7/2005 | Raymond et al. | |
| 2005/0165405 A1 | 7/2005 | Tsou | |
| 2005/0203490 A1 | 9/2005 | Simonson | |
| 2005/0216002 A1 | 9/2005 | Simonson | |
| 2005/0228233 A1 | 10/2005 | Ritland | |
| 2005/0277812 A1 | 12/2005 | Myles | |
| 2005/0288677 A1 | 12/2005 | Stauber | |
| 2006/0030858 A1 | 2/2006 | Simonson et al. | |
| 2006/0030861 A1 | 2/2006 | Simonson et al. | |
| 2006/0030872 A1 | 2/2006 | Culbert et al. | |
| 2006/0074445 A1 | 4/2006 | Gerber et al. | |
| 2006/0106416 A1 | 5/2006 | Raymond et al. | |
| 2006/0129033 A1 | 6/2006 | Frasier et al. | |
| 2006/0155170 A1 | 7/2006 | Hanson et al. | |
| 2006/0200185 A1 | 9/2006 | Marchek et al. | |
| 2006/0200186 A1 | 9/2006 | Marchek et al. | |
| 2006/0206008 A1 | 9/2006 | Dalton | |
| 2006/0224044 A1 | 10/2006 | Marchek et al. | |
| 2006/0224045 A1 | 10/2006 | Whipple et al. | |
| 2007/0038033 A1 | 2/2007 | Jones et al. | |
| 2007/0073110 A1 | 3/2007 | Larson et al. | |
| 2007/0073111 A1 | 3/2007 | Bass | |
| 2007/0100212 A1 | 5/2007 | Pimenta et al. | |
| 2007/0100366 A1 | 5/2007 | Dziedzic et al. | |
| 2007/0156023 A1 | 7/2007 | Frasier et al. | |
| 2007/0156024 A1 * | 7/2007 | Frasier et al. | 600/219 |
| 2007/0156025 A1 | 7/2007 | Marchek et al. | |
| 2007/0156026 A1 | 7/2007 | Frasier et al. | |
| 2007/0191685 A1 | 8/2007 | LeVahn et al. | |
| 2007/0191686 A1 | 8/2007 | Sharratt et al. | |
| 2007/0203400 A1 | 8/2007 | Santilli | |
| 2007/0208226 A1 | 9/2007 | Grey et al. | |
| 2007/0208227 A1 | 9/2007 | Smith et al. | |
| 2007/0208228 A1 | 9/2007 | Pavento et al. | |
| 2007/0208229 A1 | 9/2007 | Prusmack | |
| 2007/0208366 A1 | 9/2007 | Pellegrino et al. | |
| 2007/0213596 A1 | 9/2007 | Hamada | |

(56) References Cited

U.S. PATENT DOCUMENTS

| | | |
|---|---|---|
| 2007/0213597 A1 | 9/2007 | Wooster |
| 2007/0219416 A1 | 9/2007 | Perez-Cruet et al. |
| 2007/0225568 A1 | 9/2007 | Colleran |
| 2007/0225743 A1 | 9/2007 | Lamadon |
| 2007/0232864 A1 | 10/2007 | Sharp et al. |
| 2007/0238932 A1 | 10/2007 | Jones et al. |
| 2007/0244489 A1 | 10/2007 | Patel et al. |
| 2007/0255109 A1 | 11/2007 | Stein et al. |
| 2007/0260125 A1 | 11/2007 | Strauss et al. |
| 2007/0270655 A1 | 11/2007 | Smith et al. |
| 2007/0276190 A1 | 11/2007 | Tsahakis |
| 2007/0276191 A1 | 11/2007 | Selover et al. |
| 2008/0021284 A1* | 1/2008 | Hestad et al. ............... 600/201 |
| 2008/0114208 A1* | 5/2008 | Hutton et al. ............... 600/201 |
| 2008/0188718 A1 | 8/2008 | Spitler et al. |
| 2008/0214898 A1 | 9/2008 | Warren |
| 2008/0215081 A1 | 9/2008 | Hsueh et al. |
| 2008/0221394 A1 | 9/2008 | Melkent et al. |
| 2008/0221586 A1 | 9/2008 | Garcia-Bengochea et al. |
| 2008/0234550 A1 | 9/2008 | Hawkes et al. |
| 2008/0249372 A1 | 10/2008 | Reglos et al. |
| 2009/0221877 A1 | 9/2009 | Woods |
| 2009/0221878 A1 | 9/2009 | Gorek |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |
| 2009/0259108 A1 | 10/2009 | Miles et al. |
| 2011/0245620 A1* | 10/2011 | Hamada ..................... 600/219 |
| 2011/0270042 A1* | 11/2011 | Giulianotti et al. .......... 600/228 |
| 2011/0270314 A1* | 11/2011 | Mueller et al. .............. 606/264 |
| 2011/0313256 A1* | 12/2011 | Raymond et al. ............ 600/231 |
| 2013/0023735 A1* | 1/2013 | Brown et al. ............... 600/229 |
| 2014/0088370 A1* | 3/2014 | Giulianotti et al. .......... 600/228 |

FOREIGN PATENT DOCUMENTS

| | | |
|---|---|---|
| EP | 632997 A1 | 1/1995 |
| EP | 1829488 A1 | 9/2007 |
| FR | 1019217 A | 1/1953 |
| FR | 2788958 A1 | 8/2000 |
| FR | 2807313 A1 | 10/2001 |
| JP | 11262491 A * | 9/1999 |
| WO | WO9001298 A1 | 2/1990 |
| WO | WO9216151 A1 | 10/1992 |
| WO | WO02060330 A1 | 8/2002 |
| WO | WO02062235 A2 | 8/2002 |
| WO | WO2004000140 A1 | 12/2003 |
| WO | WO2004022155 A2 | 3/2004 |
| WO | WO2004028382 A2 | 4/2004 |
| WO | WO2004047650 A2 | 6/2004 |
| WO | WO2005032385 A1 | 4/2005 |
| WO | WO2005053513 A2 | 6/2005 |
| WO | WO 2005/060837 A3 | 7/2005 |
| WO | WO2005060613 A2 | 7/2005 |
| WO | WO2005060837 A2 | 7/2005 |
| WO | WO2005070329 A2 | 8/2005 |
| WO | WO2005094695 A2 | 10/2005 |
| WO | WO2005122871 A2 | 12/2005 |
| WO | WO2006017507 A2 | 2/2006 |
| WO | WO2006049917 A2 | 5/2006 |
| WO | WO 2006/058079 A2 | 6/2006 |
| WO | WO2005096735 A9 | 8/2006 |
| WO | WO2005122871 A3 | 8/2006 |
| WO | WO2006096517 A2 | 9/2006 |
| WO | WO2006104990 A1 | 10/2006 |
| WO | WO2006105068 A1 | 10/2006 |
| WO | WO2006107472 A2 | 10/2006 |
| WO | WO2006108067 A2 | 10/2006 |
| WO | WO2006116336 A2 | 11/2006 |
| WO | WO2006138515 A2 | 12/2006 |
| WO | WO2007103173 A2 | 9/2007 |
| WO | WO2007103997 A2 | 9/2007 |
| WO | WO2007114982 A1 | 10/2007 |
| WO | WO2007118177 A2 | 10/2007 |
| WO | WO2007118179 A2 | 10/2007 |
| WO | WO2008121421 A1 | 10/2008 |

* cited by examiner

DETAIL A SCALE 16 : 1

SECTION B-B

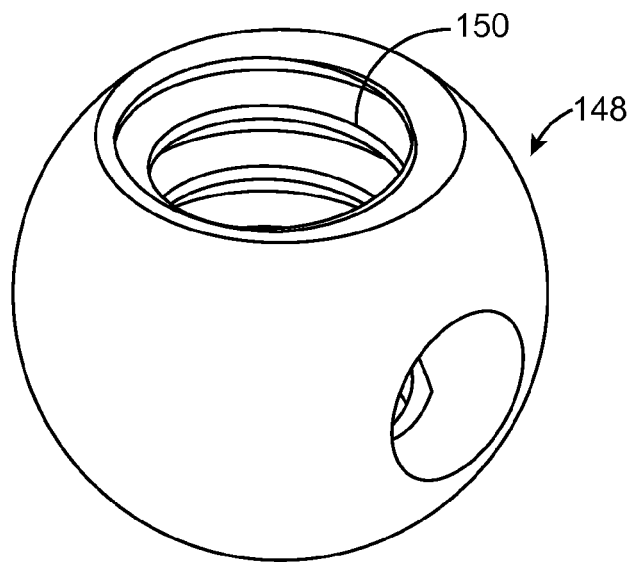
FIG. 16
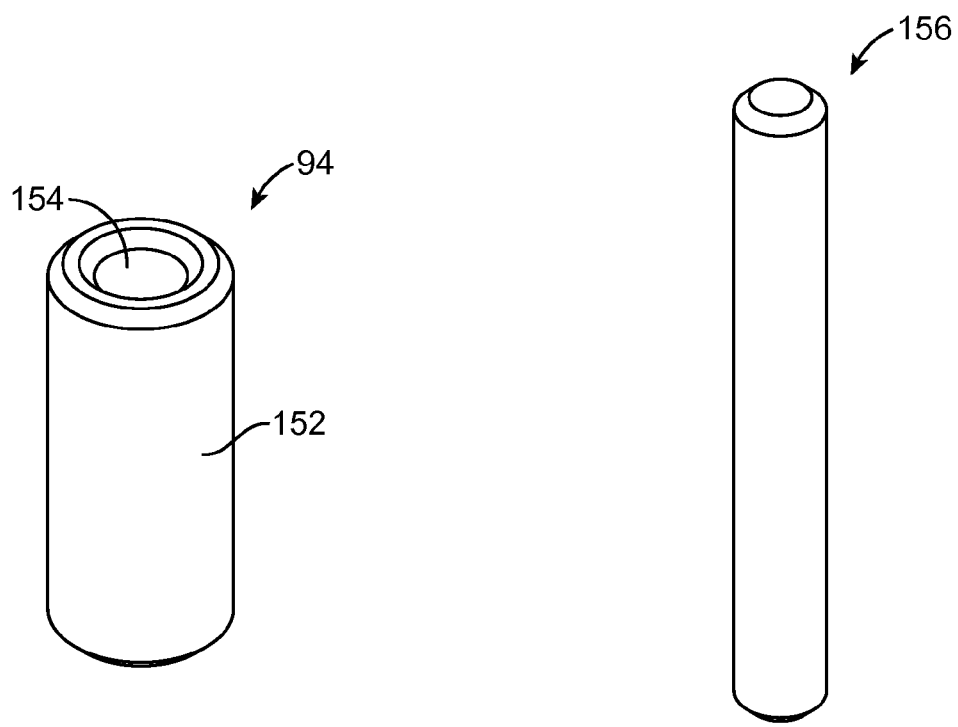
FIG. 17A
FIG. 17B

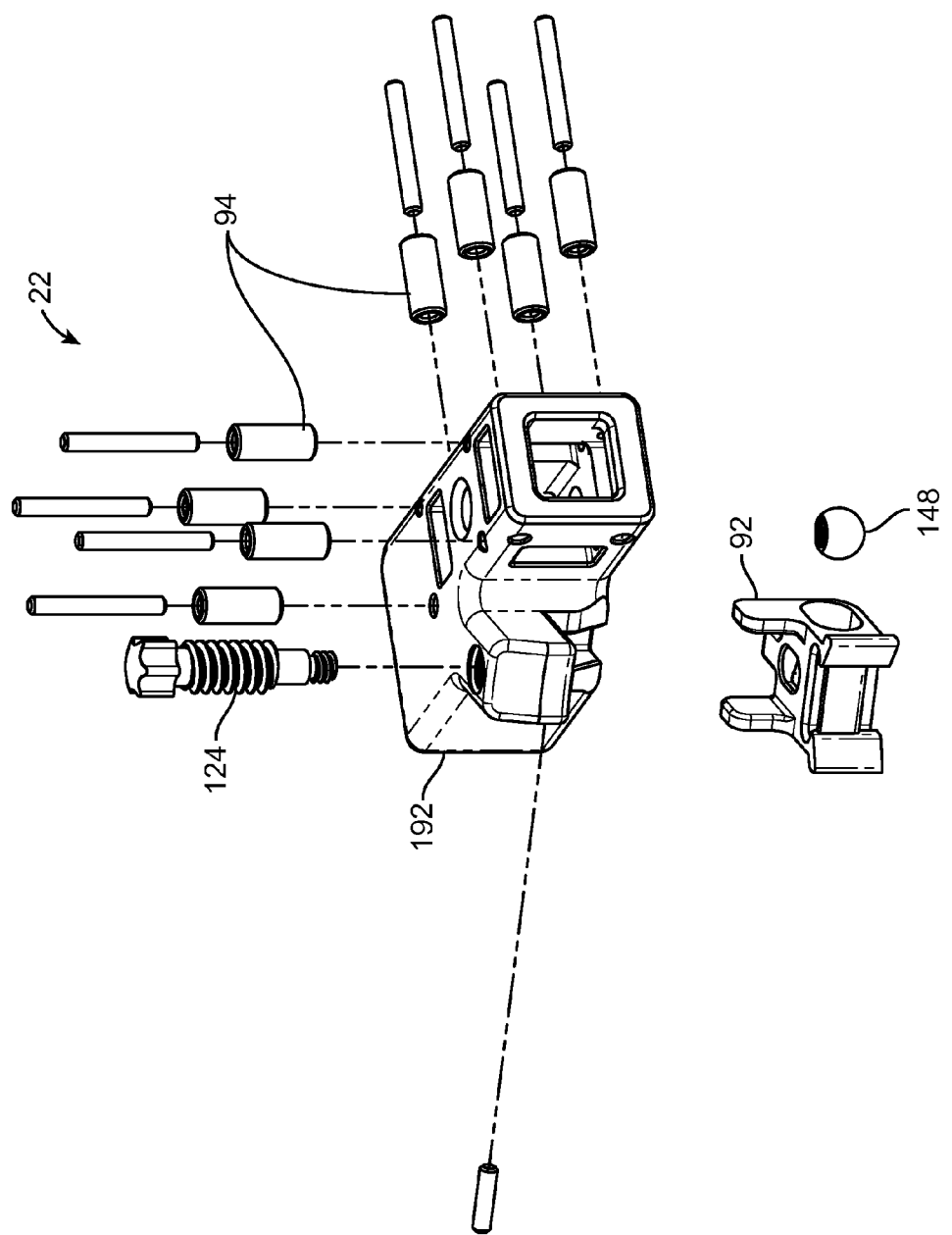

SECTION B-B

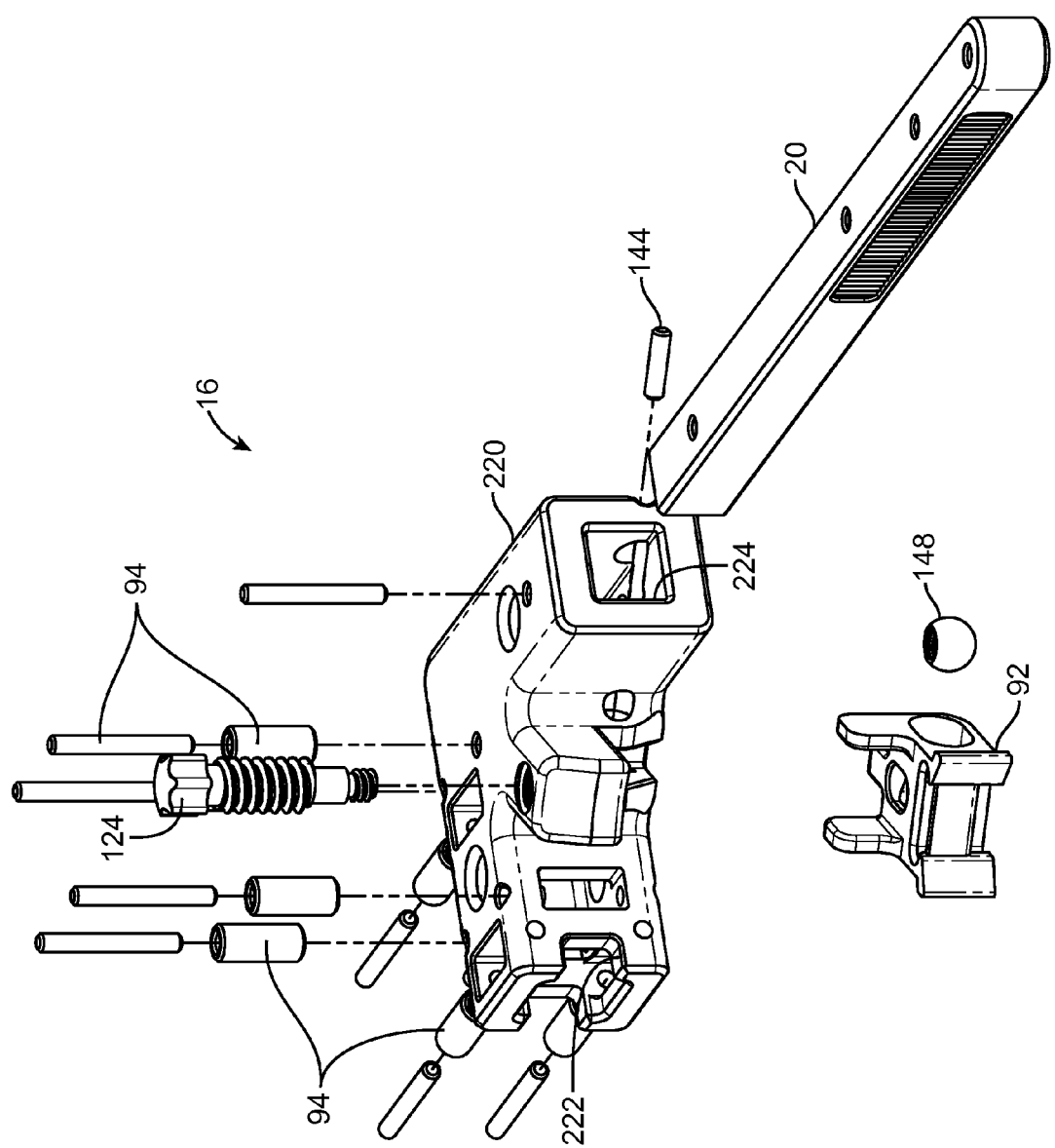

SECTION B-B

SECTION B-B

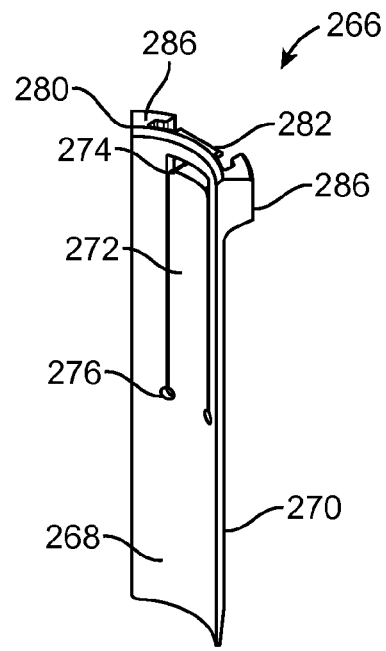
FIG. 29A
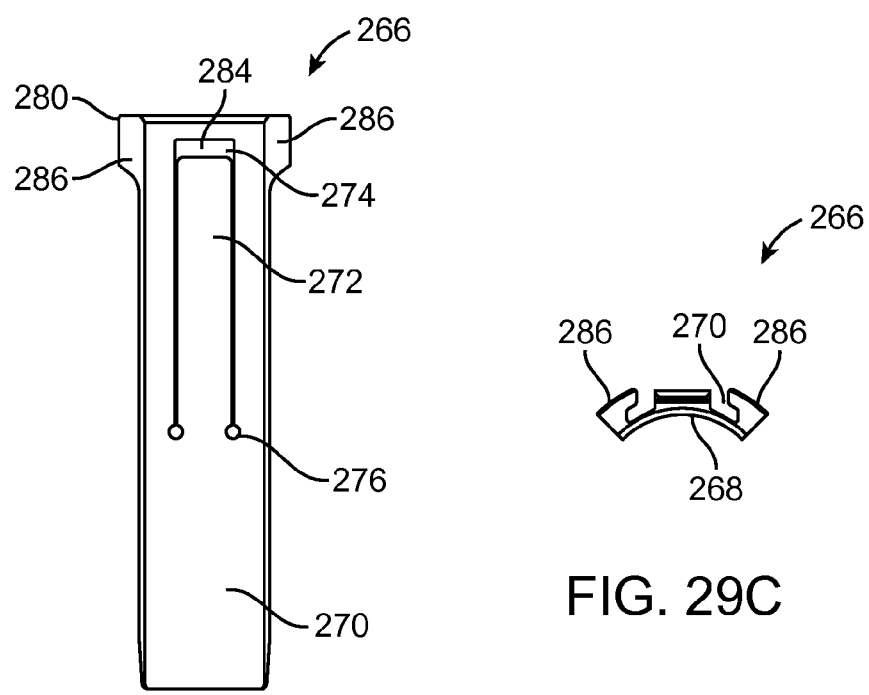
FIG. 29B
FIG. 29C

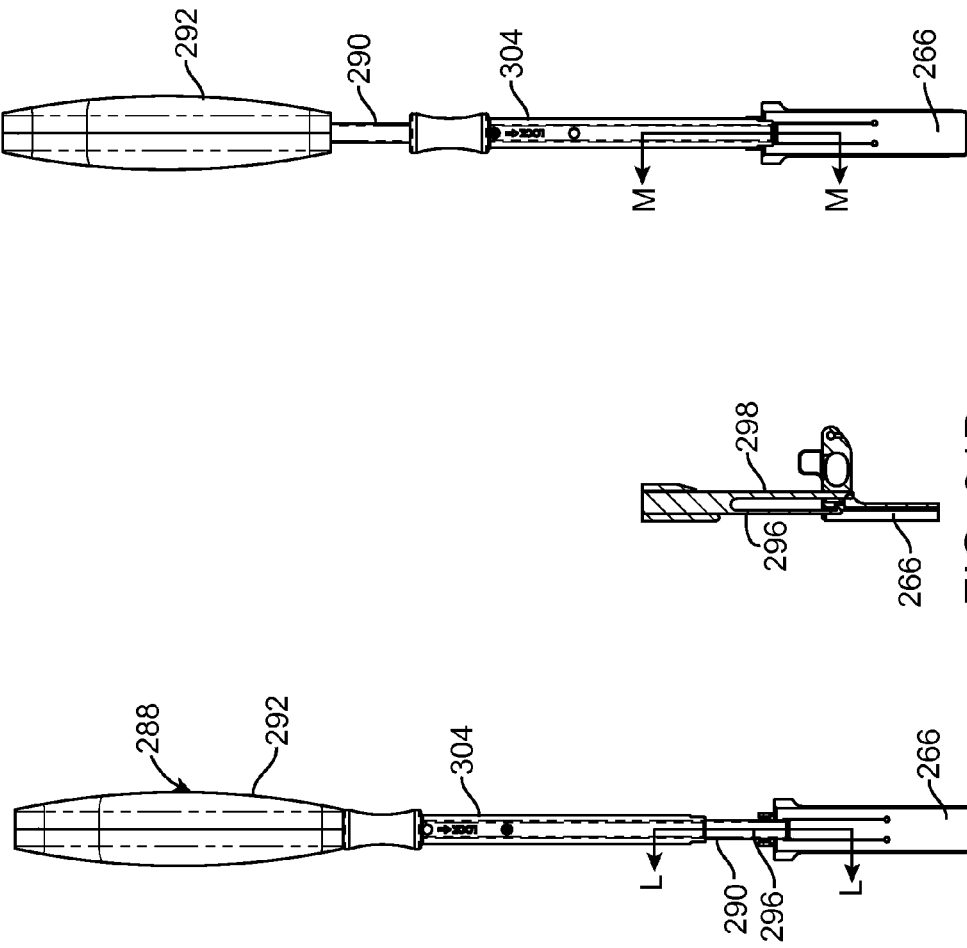

RETRACTOR

CROSS-REFERENCE TO RELATED APPLICATION

This application claims priority to and benefit of U.S. Provisional Patent Application Ser. No. 61/717,202 entitled "Retractor" filed on Oct. 23, 2012 which is incorporated herein by reference in its entirety.

FIELD

This invention relates to surgical instruments and methods and, more particularly, to surgical retractors for use in spinal surgery and other types of surgical procedures.

BACKGROUND

Surgical procedures often require the creation of a surgical exposure to clear the field for the surgeon and to provide access to the desired area. The surgical exposure is usually started with an incision of a suitable depth. Surgical instruments known as retractors are then inserted into the incision and used to pull back skin, muscle and other soft tissue to permit access to the region of interest, reach deeper regions of the body, protect adjacent tissues and provide the surgeon with clear visibility of the area of the surgical field.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades can be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

The retractors in use today retract the opening created in the body of the patient in a uniform manner. If the surgeon needs a large opening near the spine, for instance, the opening in the body of the patient is typically retracted in a uniform manner. In an "open" spinal surgical procedure, large bands of muscles in the back are stripped free from the spine and retracted off to each side. This allows for excellent visualization of the spine and easy access for the surgeon. The downside of "open" surgery is that there can be considerable back pain from the muscle retraction. Also, the muscles develop some degree of permanent scar formation and damage as a result of the necessary retraction. This creates significant trauma for the patient and increases the patient's recovery time. What is needed is a surgical retractor customized for spinal surgery that gives a surgeon a suitable area within the body to work on the patient while reducing the required incision size. This reduces trauma to the patient and reduces the patient's recovery time.

SUMMARY

According to one aspect of the invention, a surgical retractor is disclosed. The surgical retractor includes a first rail and a second rail connected at an angle and defining a retractor plane. The first rail includes an outer surface and a plurality of teeth recessed with respect to the outer surface such that the plurality of teeth does not extend beyond the outer surface. The second rail includes an outer surface and a plurality of teeth recessed with respect to the outer surface such that the plurality of teeth of the second rail does not extend beyond the outer surface of the second rail. The retractor further includes a first slider configured to slide inwardly and outwardly along the first rail and carry a first blade at an angle to the retractor plane. The first slider includes a first lock configured to arrest movement of the first slider in at least one direction relative to the first rail. The first slider includes a plurality of bearings arranged about the outer surface of the first rail such that the plurality of bearings does not contact the plurality of teeth of the first rail. The second slider is configured to slide inwardly and outwardly along the second rail and carry a second blade at an angle to the retractor plane. The second slider includes a second lock configured to arrest movement of the second slider in at least one direction relative to the second rail. The second slider includes a plurality of bearings housed in the second slider and arranged about the outer surface of second rail such that the plurality of bearings does not contact the plurality of teeth of the second rail.

According to another aspect of the invention, a surgical retractor is disclosed. The surgical retractor includes a first rail and a second rail connected at an angle and defining a retractor plane. The first rail includes an outer surface and a plurality of teeth recessed with respect to the outer surface such that the plurality of teeth does not extend beyond the outer surface. The second rail includes an outer surface and a plurality of teeth recessed with respect to the outer surface such that the plurality of teeth of the second rail does not extend beyond the outer surface of the second rail. The retractor further includes a first slider configured to slide inwardly and outwardly along the first rail and carry a first blade at an angle to the retractor plane. The first slider includes a first lock configured to arrest movement of the first slider in at least one direction relative to the first rail. The first slider includes a plurality of bearings arranged about the outer surface of the first rail such that the plurality of bearings does not contact the plurality of teeth of the first rail. The second slider is configured to slide inwardly and outwardly along the second rail and carry a second blade at an angle to the retractor plane. The second slider includes a second lock configured to arrest movement of the second slider in at least one direction relative to the second rail. The second slider includes a plurality of bearings housed in the second slider and arranged about the outer surface of second rail such that the plurality of bearings does not contact the plurality of teeth of the second rail. The retractor further includes a third slider configured to slide inwardly and outwardly along the first rail and carry a third blade at an angle to the retractor plane. The third slider includes a third lock configured to arrest movement of the third slider in at least one direction relative to the first rail. The third slider includes a plurality of bearings arranged about the outer surface of the first rail such that the plurality of bearings does not contact the plurality of teeth of the first rail. The second rail is connected to the third slider. The further including a third rail connected to the second slider. The third rail is in the retractor plane and angled with respect to the first rail. The third rail includes an outer surface and a plurality of teeth recessed with respect to the outer surface such that the plurality of teeth does not extend beyond the outer surface. A fourth slider is configured to slide inwardly and outwardly along the third rail and carry a fourth blade at an angle to the retractor plane. The fourth slider includes a fourth lock configured to arrest movement of the fourth slider in at least one direction relative to the third rail. The fourth slider includes a plurality of bearings arranged about the outer surface of the third rail such that the plurality of bearings does not contact the plurality of teeth of the third rail.

According to another aspect of the invention a surgical retractor is discloses. The retractor includes at least two retractor blades that extend from a retractor body that are insertable into a surgical site. At least one of the retractor blades is movable relative to the other in order to expand the surgical site. The retractor body includes at least one rail and at least one slider. The at least one slider carries at least one retractor blade and is configured to move bidirectionally on the rail. The slider has an inner surface defining a passageway that is sized larger than the rail. The passageway is configured to receive the rail in the passageway such that the rail does not contact the inner surface and is configured to contact a plurality of antifriction bearings disposed inside the slider.

BRIEF DESCRIPTION OF THE DRAWINGS

FIG. 16 is a top perspective view of a tow angle return according to the present invention.

FIG. 17A is a top perspective view of a cylindrical bearing according to the present invention.

FIG. 17B is a top perspective view of a pin according to the present invention.

FIG. 23 is an exploded view of the third slider according to the present invention.

FIG. 25 is top perspective exploded view of the second slider and third rail according to the present invention.

FIG. 29A is a top perspective view of the blade according to the present invention.

FIG. 29B is an end elevational view of the blade according to the present invention.

FIG. 29C is a top view of the blade according to the present invention.

FIG. 31A is an end elevational view of the blade instrument connected to the blade according to the present invention.

FIG. 31B is a cross-sectional view taken along line L-L of FIG. 31A of the blade instrument connected to the blade according to the present invention.

FIG. 31C is an end elevational view of the blade instrument connected to the blade according to the present invention.

FIG. 31D is a cross-sectional view taken along line M-M of FIG. 31C of the blade instrument connected to the blade according to the present invention.

DETAILED DESCRIPTION

Figure 1:
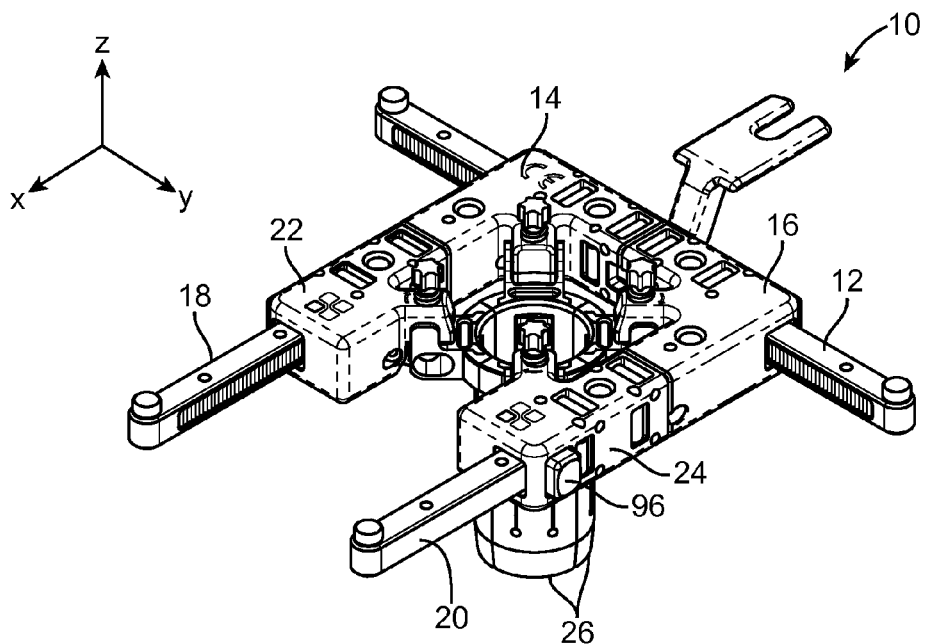
FIG. 1 is a top perspective view of the retractor according to the present invention.
Figure 2:
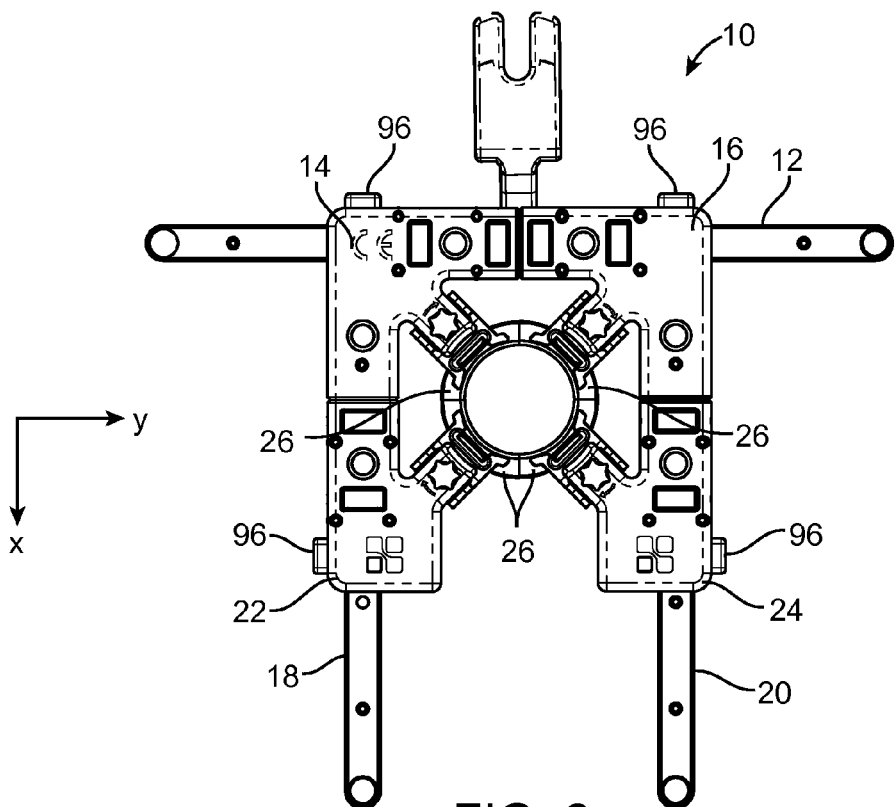
FIG. 2 is a top view of the retractor according to the present invention.
Figure 3:
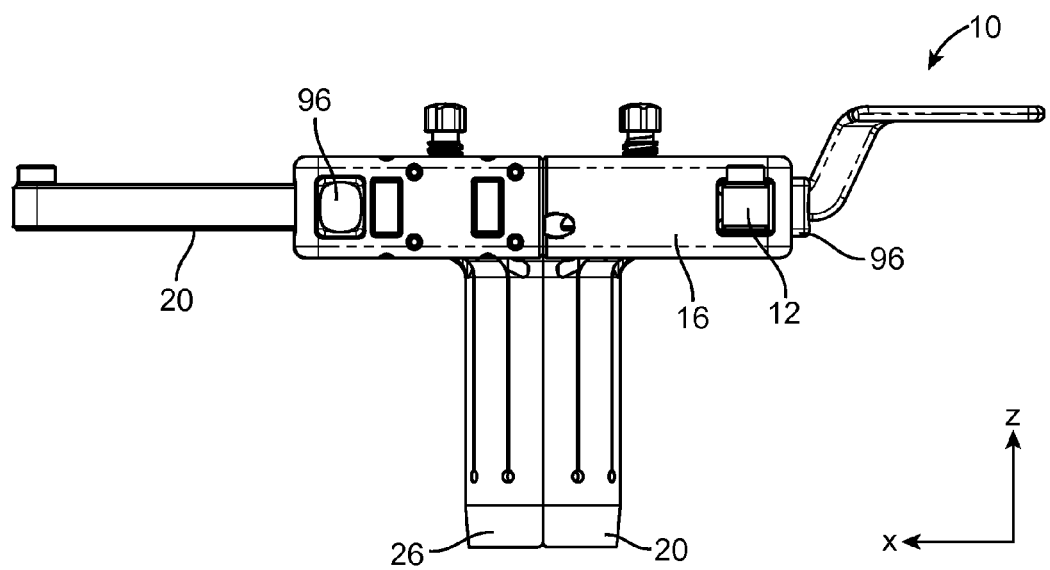
FIG. 3 is a side elevation view of the retractor according to the present invention.
Figure 4:
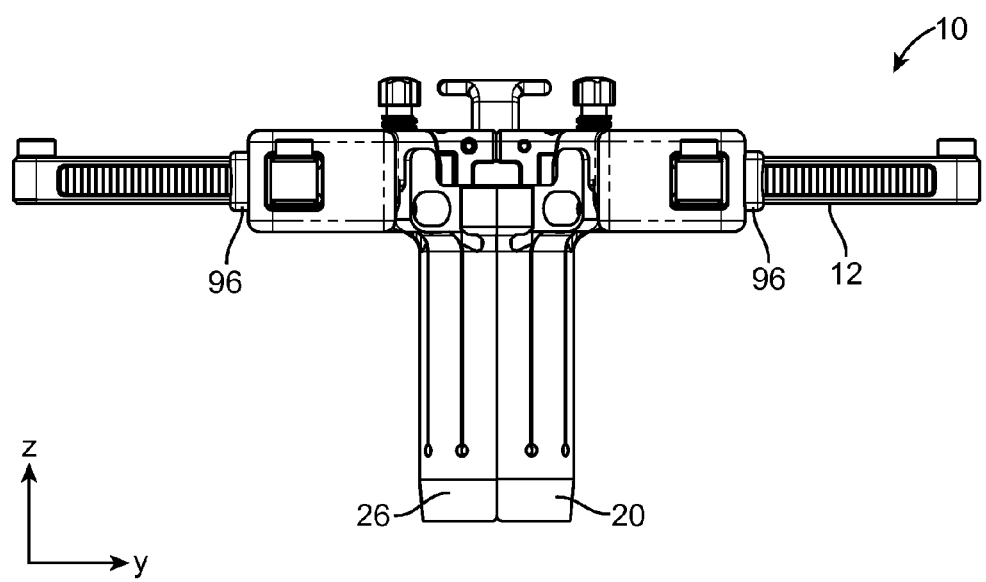
FIG. 4 is an end elevation view of the retractor according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw"

includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of surgical retractors.

In use, the whole retractor assembly shown in the figures is introduced into the surgical field. Upon introduction, the initial configuration of the retractor is in a closed position such that the retractor blades extend downwardly and all of the distal ends of each blade are in close proximity to one another to allow ease of introduction. Once inserted at the desired location, the retractor forms a small field of visibility. The surgeon then causes the blades to be expanded outwardly by operating the various constructs shown in the figures to customize the degree and directions of retraction. One or more of the blades rotate outwardly and/or translate along multi-axial directions. Once in position, the blades are then locked to achieve a custom retraction according to surgeon preference and patient anatomy. The expanded blades act to spread the muscle and tissue further to provide retraction beyond the ring of view formed when the retractor is first inserted. The retractor of the present invention is customized for the demands of spinal surgery and reduces the "creep" of muscle or other tissue into the surgical field leaving a larger and more secure surgical area to be exposed for surgical access, increased visibility and stability.

The entire device may be constructed of surgical steel, or alternatively, various components of the device may be constructed of one or more materials selected from the group consisting of stainless steel, titanium and plastics.

With reference to the figures, the retractor will now be described in detail. Various views of a retractor 10 according to the present invention are shown in FIGS. 1-4. The retractor 10 includes at least one main or first rail 12. A first slider 14 and a second slider 16 are connected to the at least one main rail 12. A second rail 18 is connected to the first slider 14 and a third rail 20 is connected to the second slider 16. A third slider 22 is connected to the second rail 18 and a fourth slider 24 is connected to the third rail 24. The main or first rail 12, the second rail 18 and third rail 20 together with first, second, third and fourth sliders 14, 16, 22, 24 are all coplanar or parallel to the X-Y plane. The three rails 12, 18, 20 form three coplanar sides of a polygon in the X-Y plane and the sliders 14, 16, 22, 24 each carry at least one blade 26. Each of the blades 26 extends downwardly from the sliders 14, 16, 22, 24 in a direction substantially perpendicular to the X-Y plane and in a direction substantially parallel to the Z-axis. In the variation shown, the second rail 18 is connected to the first slider 14 such that the second rail 18 is substantially perpendicular to the first rail 12 and the third rail 20 is connected to the second slider 16 such that the third rail 20 is substantially perpendicular to the first rail 12. Therefore, the polygon formed in the X-Y plane is a three-sided rectangle or three-sided square with the side opposite and parallel to the main or first rail 12 being absent or open. The interior of the retractor polygon defines the retractor zone.

Figure 5:
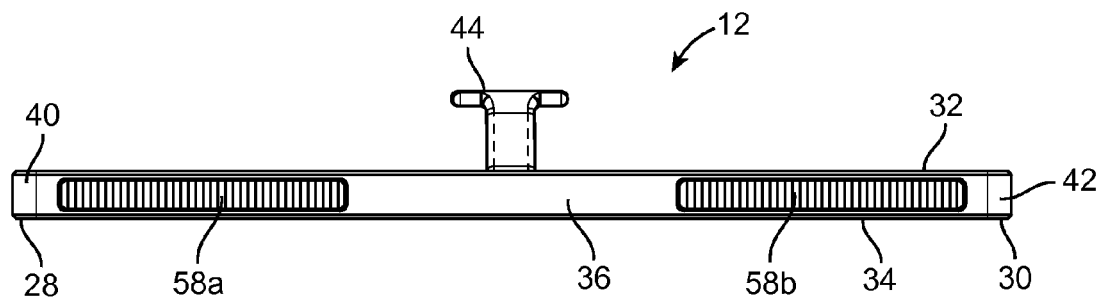
FIG. 5 is an end elevation view of the first rail according to the present invention.
Figure 6:
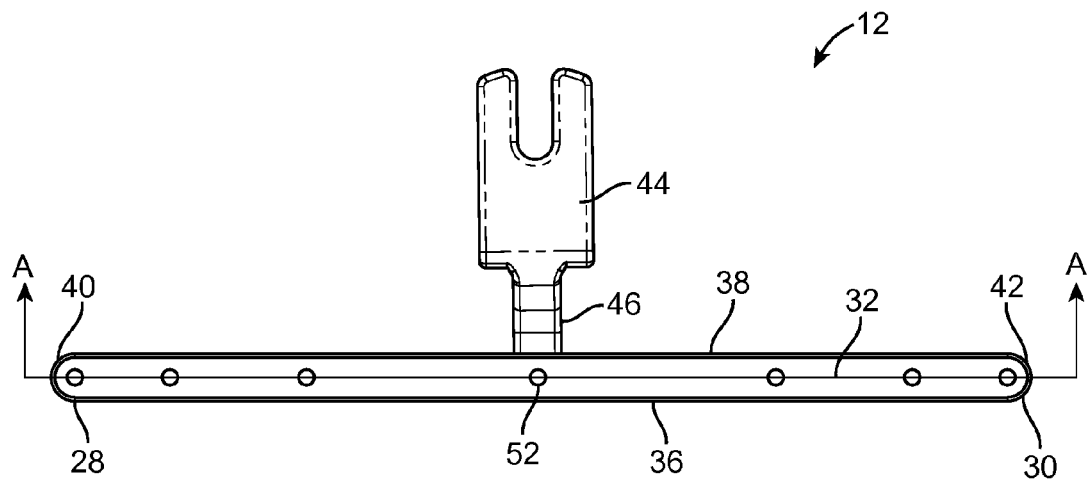
FIG. 6 is a top view of the first rail according to the present invention.
Figure 7:
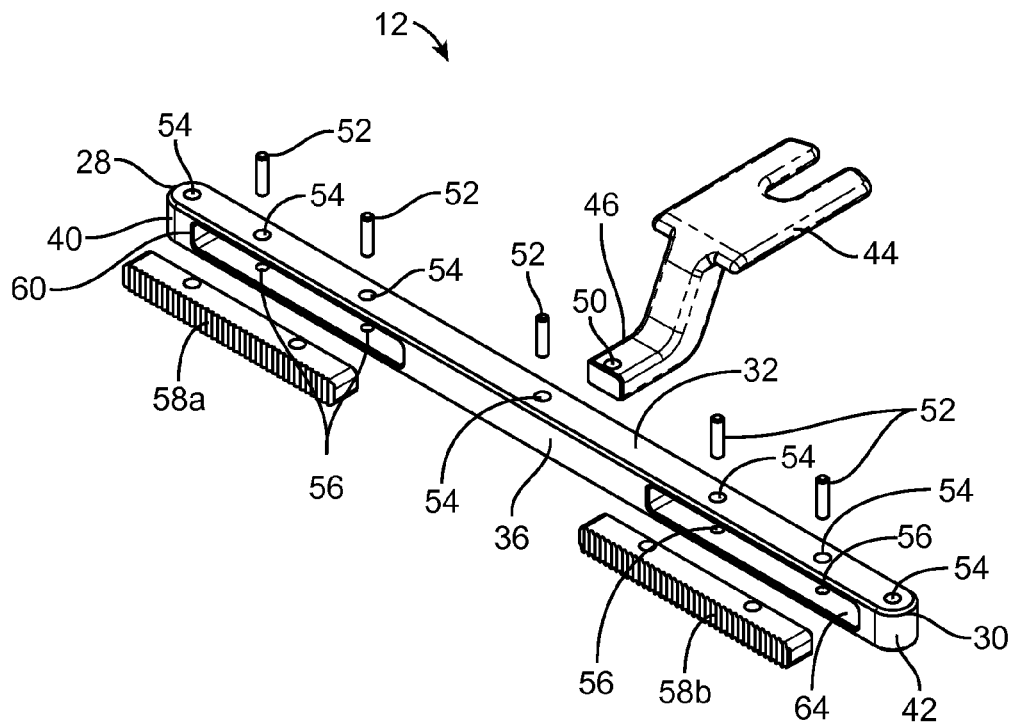
FIG. 7 is an exploded top perspective view of the first rail according to the present invention.

Turning now to FIGS. 5-7, there is shown a first or main rail 12 according to the present invention. The main rail 12 is an elongate, straight bar that is made of metal such as surgical steel or titanium. The main rail 12 includes a first distal end 28 and a second distal end 30 and has a top surface 32 and a bottom surface 34 interconnected by an inner surface 36 and an outer surface 38 to define a substantially square or rectangular cross-section perpendicular to the longitudinal axis of the main rail 12. A curved first end surface 40 is formed at the first distal end 28 and a curved second end surface 42 is formed at the second distal end 30.

A handle 44 is optionally included with the first rail 12. The handle 44 includes a leg 46 that is inserted into a leg opening (not shown) formed in the outer surface 38 of the main rail 12. A pin 52 is passed through an aperture 54 in the top surface 32, through a pin aperture 50 formed in the leg 46 and into an aperture 56 formed in the bottom surface 34 and the pin 52 is laser welded to connect the handle 44 to the main rail 12.

The main rail 12 further includes at least one track 58. FIGS. 5-7 show a variation having a first track 58a and a second track 58b connected to the main rail 12. Although two tracks 58a, 58b are shown the invention is not so limited and multiple tracks or a single track that is longer is within the scope of the present invention. The first track 58a is disposed in a first track-receiving portion 60 and the second track 62 is disposed in a second track-receiving portion 64. Each of the first and second tracks 58, 62 is an elongate bar having a square or rectangular cross-section taken perpendicular to the longitudinal axis or has a cross-section that has the same shape as, although smaller in size than, the cross-section of the first rail 12 within which it is disposed. In the variation shown in FIGS. 5-7, the first track 58 is identical to the second track 62 having the same length, shape and configuration that can be seen in greater detail in FIGS. 8-10.

Figure 8:
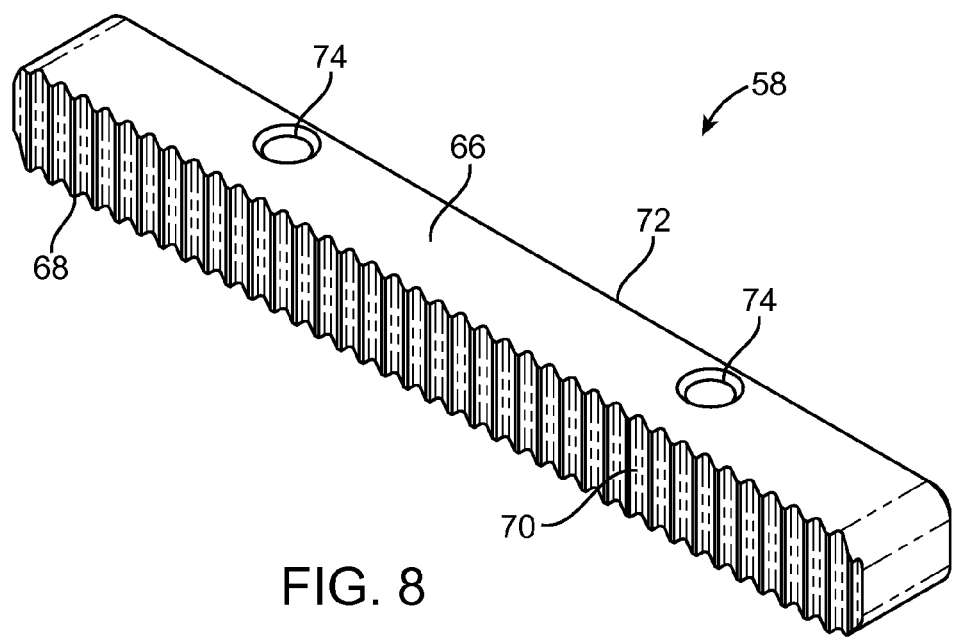
FIG. 8 is a top perspective view of a track according to the present invention.
Figure 9:
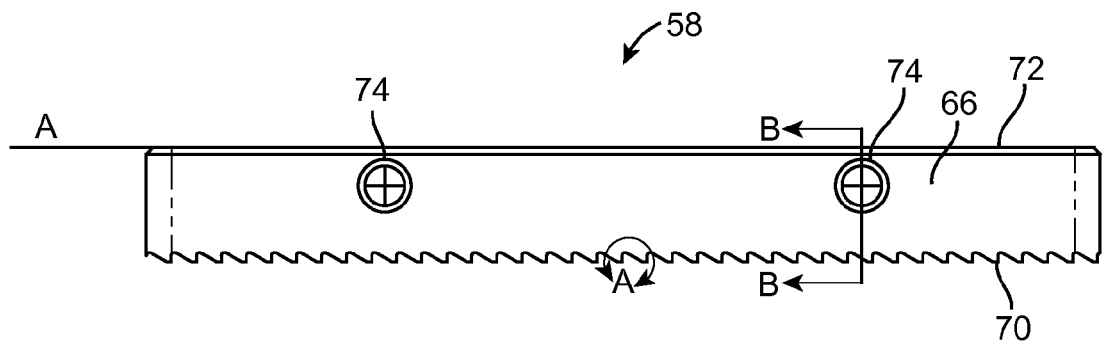
FIG. 9 is a top view of a track according to the present invention.
Figure 10:
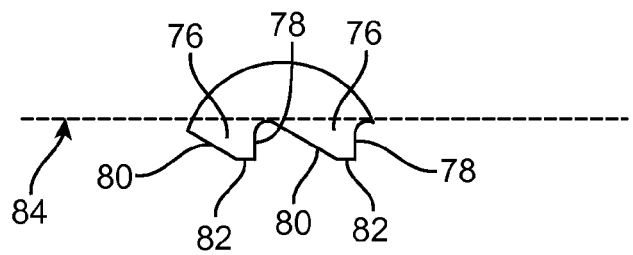
FIG. 10 is a sectional view of a track according to the present invention.

Turning now to FIGS. 8-10, the track 58 includes a flat top surface 66 and a flat bottom surface 68 interconnected by a toothed inner surface 70 and a flat outer surface 72. Pin apertures 74 extend from the top surface 66 to the bottom surface 68 and are sized and configured for receiving pins 52 for connecting the at least one tracks 58 to a rail. The inner surface 70 of the track 58 is toothed providing a gearing surface or rack for engagement with respective sliders to lock or permit motion of the respective sliders relative to the rail. The inner surface 70 is provided with a plurality of teeth 76, the detail of which is shown in FIG. 10.

With particular reference to FIG. 10, two adjacent teeth 76 are shown. Each tooth 76 includes a right flank 78 interconnected to a left flank 80 at a top land 82 or point. At least one of the right or left flanks 78, 80 is substantially perpendicular to a baseline 84 and at least one of the right or left flanks 78, 80 is angled with respect to the baseline 84. In FIG. 10, the left flank 80 is shown angled with respect to the baseline 84 to permit unidirectional movement of a slider, gear tooth or locking tooth in a direction from the left flank 80 toward the right flank 78.

Turning back to FIGS. 5-7, the first track-receiving portion 60 is sized and configured to receive the first track 58a and the second track-receiving portion 64 is sized and configured to receive the second track 58b. The first and second track-receiving portions 60, 64 are recesses or channels sized and configured to receive their respect tracks 58a, 58b. Pins 52 are passed through apertures 54 in the top surface 32 and bottom surface 34 of the first rail 12 and through pin apertures 74 in the tracks 58, 62. The pins 52 are laser welded to connect the tracks 58, 62 to the first rail 12. As mentioned above, a variation having a single track is within the scope of the invention; wherein the single track is longer and extends across most of the first rail to permit engagement with both sliders 14, 16.

Still referencing FIGS. 5-10, the two tracks 58a, 58b provide the first rail 12 with two toothed surfaces 70 such that the teeth 76 are recessed from the inner surface 36 of the first rail 12 as can be seen in FIG. 6. The teeth 76 do not protrude or extend beyond the outer surface 36 of the first rail 12. In one variation, the top land 82 of each tooth 76 is even with the outer surface 36 of the rail 36. In another variation, the top land 82 is slightly recessed or setback from the outer surface 36 of the top rail 12. In general, the right or left flanks 78, 80 do not protrude beyond the outer surface 36 of the first rail 12. Thereby, the tracks 58a, 58b are set within the respective receiving portions 60, 64. In another variation, the first rail 12 does not include first and second tracks 58a, 58b located within first and second track-receiving portions 60, 64, respectively; instead, the first rail 12 itself is provided with at least one toothed surface as described integrally formed with the rail 12 instead of being formed as insertable tracks separate from the rail. Furthermore, the at least one toothed surface can be located along one or more surfaces of the first rail 12 such as the top surface 32, bottom surface 34, inner surface 36 and/or outer surface 38.

The tracks 58a, 58b are configured to engage a locking tooth of the first and second sliders 14, 16 to lock the first and second sliders 14, 16 from movement relative to the first rail 12. Disengagement of a locking tooth from the one of the sliders 14, 16 permits the disengaged slider to move relative to the first rail 12. In another variation, engagement of the locking tooth with a track 58 locks the slider only in one direction along the Y-axis and the slider is free to move in the opposite direction. This unidirectional locking of a slider advantageously facilitates the opening or increasing of the retractor zone without requiring the release of the locking tooth. Preferably, the track and locking tooth are configured such that the locking tooth and track 58 locks movement of the slider in a direction that closes reduces the retraction zone. In other words, the sliders 14, 16 are permitted to move outwardly away from the handle 44 along the first rail 12 by the locking tooth ramping over one of the right or left flanks. For example, in the first track 58a, the right flanks 78 are angled to permit movement of the first slider 14 along the first rail 12 in an outwardly direction with the locking tooth engaged. In the second track 58b, the left flanks 80 are angled to permit movement of the second slider 16 in an outwardly direction with the locking tooth engaged.

Still referencing FIGS. 5-10, the first track 58a is placed proximally to the first distal end 28 of the first rail 12 such that the left flanks 80 of all of the teeth 76 on the first track 58 are configured to permit unidirectional travel of the first slider 14 in a direction parallel to the X-axis and away from the handle 44 and toward the first distal end 28. Hence, the left flanks 80 of all of the teeth 76 on the first track 58 are perpendicular to the base 84 or top land 82 and the right flanks 78 are angled to permit the first slider 14 to move outwardly toward the first distal end 28 but prevent or restrict movement of the first slider 14 toward the handle 44 or the second distal end 30 while the locking tooth is engaged.

The second track 60 is placed proximally to the second distal end 30 of the first rail 12 such that the left flanks 80 of all of the teeth 76 on the second track 60 are configured to permit unidirectional travel of the second slider 16 in a direction parallel to the X-axis and away from the handle 44 and toward the second distal end 30. Hence, the right flanks 78 of all of the teeth 76 on the second track 60 are perpendicular to the base 84 or top land 82 when viewed from the top and the left flanks 78 are angled to permit the second slider 16 to move outwardly toward the second distal end 30 but prevent or restrict movement of the second slider 16 toward the handle 44 or the first distal end 28 while the locking tooth of the slider 44 is engaged.

Figure 11:
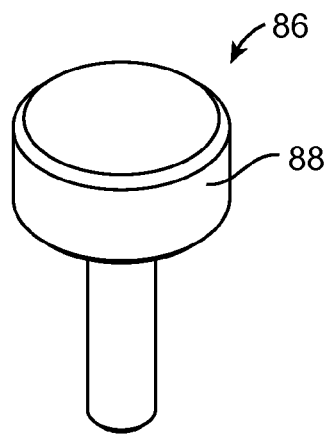
FIG. 11 is a top perspective view of stop pin according to the present invention.

Still referencing FIGS. 1-7 and FIG. 11, the first rail 12 includes an aperture 54 near the first distal end 28 extending from the top surface 32 to the bottom surface 34 of the first rail 12 configured to receive a stop pin 86 having an enlarged head 88 as shown in FIG. 11. The enlarged head 88 is positioned above the top surface 32 when the stop pin 86 is in place and serves to stop the sliding motion of the first slider 14 preventing it from moving off the first rail 12. A similar aperture 54 is located near the second distal end 30 extending from the top surface 32 to the bottom surface 34 of the first rail 12 configured to receive a stop pin 86 having an enlarged head 88. The enlarged head 88 extends above the top surface 32 when the stop pin 86 is in place and serves to stop the sliding motion of the second slider 16 preventing it from falling off the first rail 12. Of course, the stop pins 86 are placed after the sliders 14, 16 are connected to the first rail 12. The sliders 14, 16 are arrested when traveling toward the handle 44 by abutting the handle 44 itself.

Figure 12:
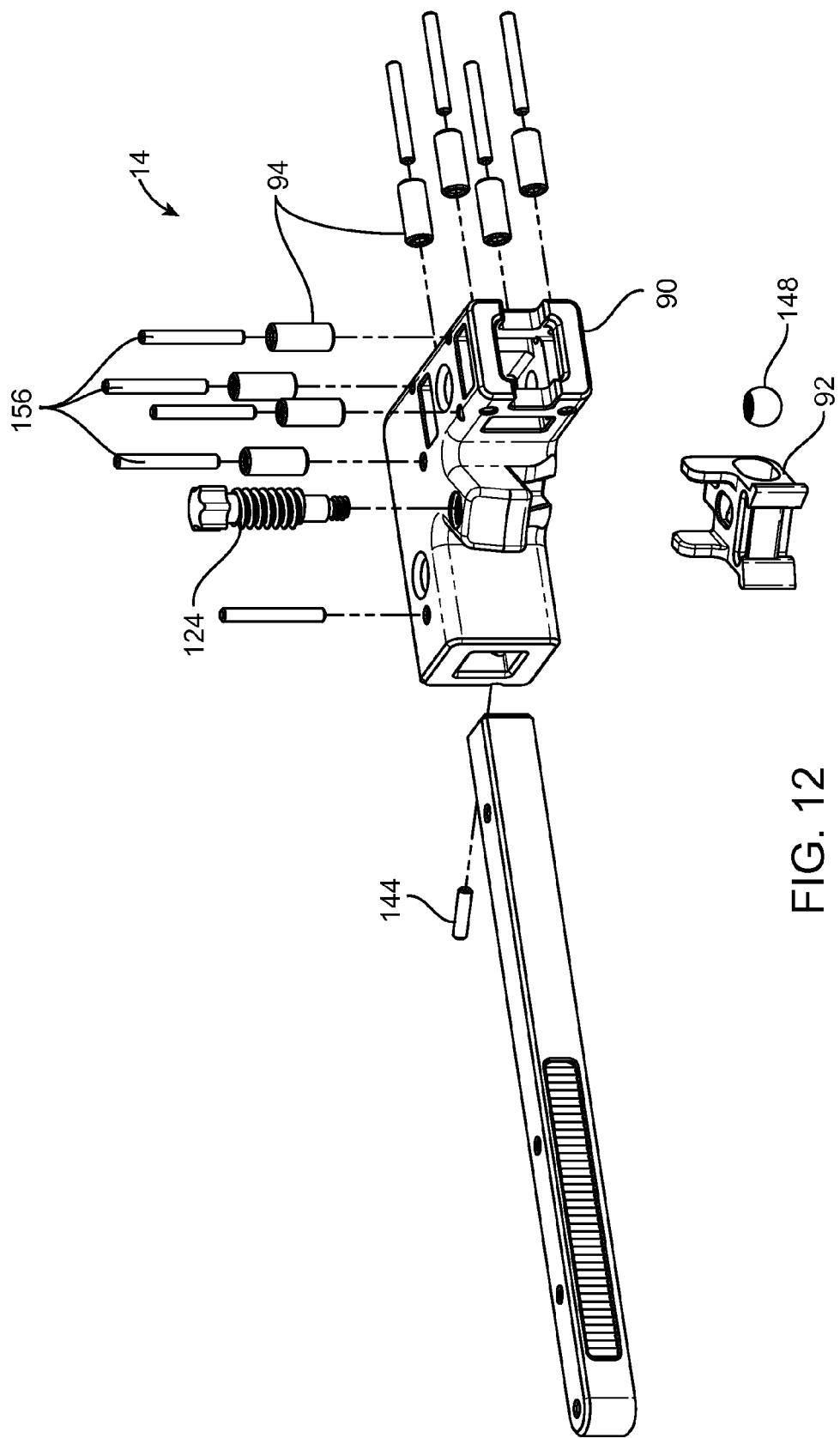
FIG. 12 is top perspective exploded view of the first slider and second rail according to the present invention.
Figure 13A:
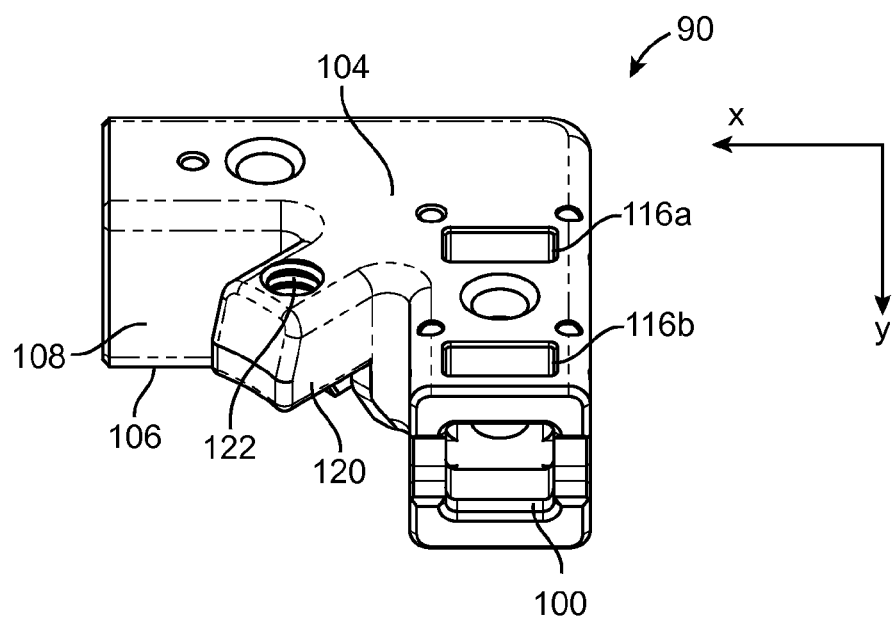
FIG. 13A is a top perspective view of the housing of the first slider according to the present invention.
Figure 13B:
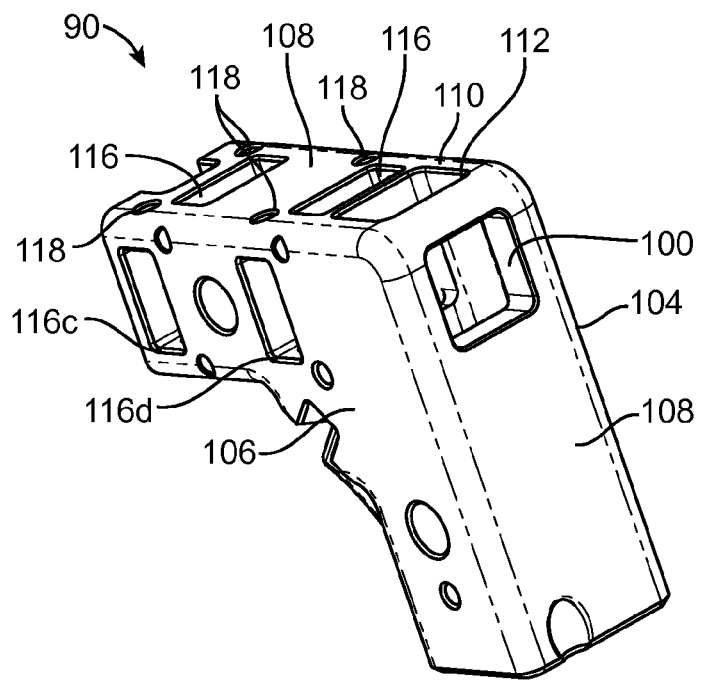
FIG. 13B is a bottom perspective view of a housing of the first slider according to the present invention.
Figure 13C:
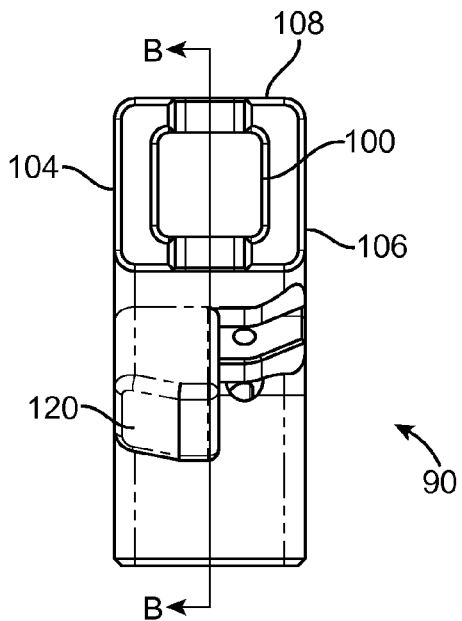
FIG. 13C is an end elevational view of a housing of the first slider according to the present invention.
Figure 13D:
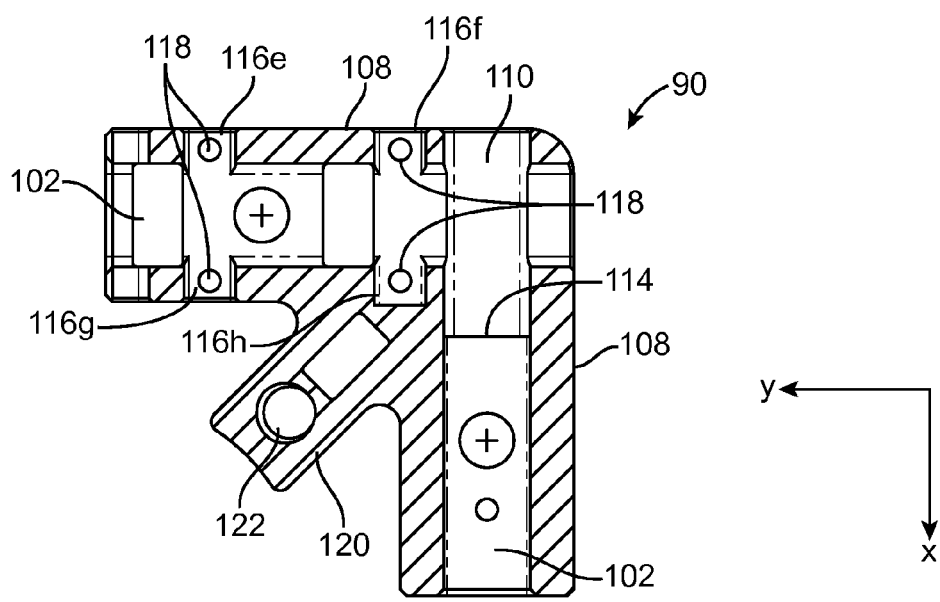
FIG. 13D is a cross-sectional view taken along line B-B of FIG. 13C of a housing of the first slider according to the present invention.

Turning now to FIGS. 12-13, the first slider 14 will now be described. The slider 14 includes a housing 90, a blade mount 92, a plurality of antifriction bearings 94 and a lock 96 shown in FIGS. 18a-18b.

The housing 90 of the first slider 14 is made of any suitable material including any metal such as steel, surgical steel or titanium and defines a first rail receiving portion 100 and a second rail receiving portion 102. The housing is polygonal forming a substantially L-shaped structure having a top surface 104 and a bottom surface 106 interconnected by a plurality of side walls having side surfaces 108 to the outside to define the housing 90. The first rail receiving portion 100 is formed as a channel or passageway sized and configured to receive the first rail 12 in sliding engagement therein. The passageway of first rail receiving portion 100 includes a first opening formed in a side surface 108 at one end of the housing 90 and extends to a second opening formed in a side surface 108 at a second end of the housing directly opposite from the first opening to define the passageway. The passageway has a cross-sectional area that is slightly larger than the cross-sectional area of the first rail 12 and a cross-sectional shape that is the same as the cross-sectional shape of the first rail 12.

The housing 90 includes a second rail receiving portion 102. The second rail receiving portion 102 is formed as a channel or passageway that is sized and configured to receive the second rail 18 therein. The passageway of second rail receiving portion 102 includes a first opening formed in a side surface 108 at one end of the housing 90. A second opening formed in a side surface 108 at a second end opposite the first opening is optional as an alternative variation. The passageway extends from the first opening into the housing 90 and does not necessarily have to extend or open to the second surface 108 opposite the first opening. The passageway has a cross-sectional area that is slightly larger than the cross-sectional area of the second rail 18 and a cross-sectional shape that is the same as the cross-sectional shape defined by the second rail 18. The first rail receiving portion 100 and the second rail receiving portion 102 are shown to be perpendicular to each other with the first rail receiving portion 100 substantially parallel to the Y-axis and the second rail receiving portion substantially parallel to the X-axis. Although the first and second rail receiving portions 100, 102 are shown to be configured at 90 degrees to each other, the invention is not so limited and the first and second rail receiving portions 100, 102 can be angled with respect to each other. For example, the angle between the first and second rail-receiving portions 100, 102 can be acute at approximately 30 degrees as angled as far apart as approximately 150 degrees.

The housing 90 further includes a lock receiving portion 110. The lock receiving portion 110 is sized and configured to receive a lock 96 therein. The lock receiving portion 110 intersects with the first rail receiving portion 100, preferably, at approximately 90 degrees. The lock receiving portion 110 includes an opening 112 in a side surface 108 of the housing 90 and defines a channel or passageway extending inwardly from the opening 112 and into the housing 90. The lock receiving portion 110 traverses or crosses the first rail receiving portion 100. The lock receiving portion 110 includes a back wall or stop 114 formed at the inside end of the lock receiving portion 110. In the variation shown in FIGS. 13a-13d, the lock receiving portion 110 is aligned with the second rail receiving portion 102, both being perpendicular to the first rail receiving portion 100.

Still referencing FIGS. 13a-13d, the housing 90 further includes one or more bearing receiving portions 116 along at least two sides of the first rail receiving portion 100 and interconnecting with the first rail receiving portion 100. The bearing receiving portions 116 are shown to be square or rectangular in shape, although they can have any cross-sectional shape and be curved or rounded. One side of each of the square or rectangular shaped bearing receiving portion 116 is open to the first rail receiving portion 100 such that when an antifriction bearing 94 is inserted in the bearing receiving portion 100, it provides a point or line contact with the first rail 12. In the variation shown in FIGS. 13a-13d, there are a total of eight bearing receiving portions 116 adjacent to the first rail receiving portion 100. Two bearing receiving portions 116a, 116b (see FIG. 13a) are located above the first rail receiving portion 100 and generally adjacent to the top surface 32 of the first rail 12 when it is inserted. Two bearing receiving portions 116c, 116d (see FIG. 13b) are located below the first rail receiving portion 100 and generally adjacent to the bottom surface 34 of the first rail 12 when it is inserted into the housing 90. Hence, there are four bearing receiving portions 116a, 116b, 116c, 116d each having a longitudinal axis that is parallel to the X-axis or otherwise perpendicular to the longitudinal length of the first rail 12 when inserted. The housing 90 further includes pin apertures 118 opening to the side surfaces 108 on either side of the first rail receiving portion 100. The pin apertures 118 extend inwardly to interconnect with the bearing receiving portions 116 and hold the antifriction bearings 94 in position. The pin apertures 118 have a cross-sectional area that is smaller than the cross-sectional area of the bearing receiving portions 116 taken perpendicular to the longitudinal axes of the bearing receiving portions or Y-axis.

Furthermore, two bearing receiving portions 116e, 116f (see FIG. 13d) are located along one side of first rail receiving portion 100 and generally adjacent to the one side of the first rail 12 when it is inserted into the housing 90. Two bearing receiving portions 116g, 116h (see FIG. 13) are located along the opposite or other side of the first rail receiving portion 100 and generally adjacent to the opposite or other side of the first rail 12 when it is inserted into the housing 90. Hence, there are four bearing receiving portions 116e, 116f, 116g, 116h each having a longitudinal axis that is parallel to the Z-axis or otherwise perpendicular to the longitudinal length of the first rail 12 when inserted. The housing 90 further includes pin apertures 118 opening to the top and bottom surfaces 104, 106 on either side of the first rail receiving portion 100. The pin apertures 118 extend inwardly to interconnect with the bearing receiving portions 116 and are configured to receive bearing pins to hold the antifriction bearings 94 in position. The pin apertures 118 have a cross-sectional area that is smaller than the cross-sectional area of the bearing receiving portions 116 taken perpendicular to the longitudinal axes of the bearing receiving portions 116.

The housing 90 further includes a blade mount portion 120. The blade mount portion 120 is configured to connect to a blade mount 92. The blade mount portion 120 of the housing 90 is configured as a flange that extends outwardly from the housing 90 and toward the retractor zone. In the variation shown in FIGS. 13a-13d, the blade mount portion 120 is located in the seat of an L-shaped housing 90 such that the flange extends between and at an angle to the first rail receiving portion 100 and the second rail receiving portion 102. The blade mount portion 120 includes a threaded aperture 122 configured to receive a threaded tow angle post 124.

Figure 14:
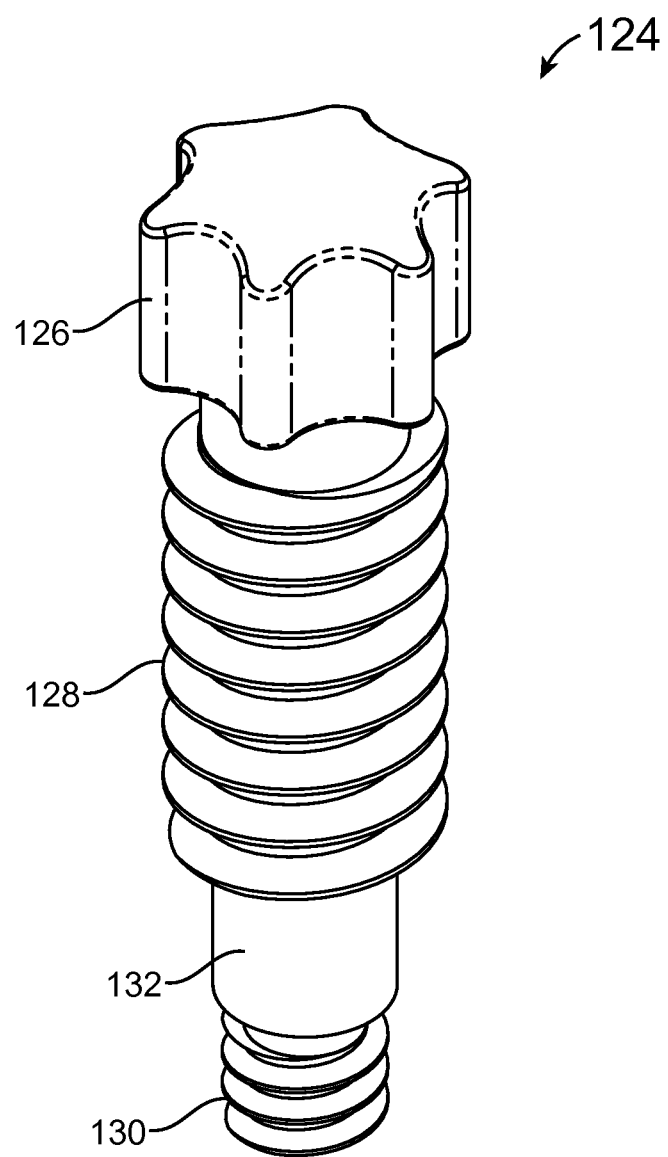
FIG. 14 is a top perspective view of a tow angle post according to the present invention.

The tow angle post 124 is shown in FIG. 14. The tow angle post 124 is an elongated fastener having a driving head 126 at the proximal end for engagement with an instrument for driving the post 124 inside the threaded aperture 122. The tow angle post 124 also includes a middle threaded portion 128 and a distal threaded portion 130. A middle non-threaded portion 132 is provided on the tow angle post 124 between the middle threaded portion 128 and a distal threaded portion 130. The distal threaded portion 130 and the non-threaded portion 132 are smaller in diameter relative to the middle threaded portion 128. The tow angle post 124 is configured to be threadingly inserted into the threaded aperture 122 of the blade mount portion 120 of the housing 90. With the tow angle post 124 inserted, the non-threaded portion 132 and the distal threaded portion 130 extend to receive a blade mount 92.

Figure 15B:
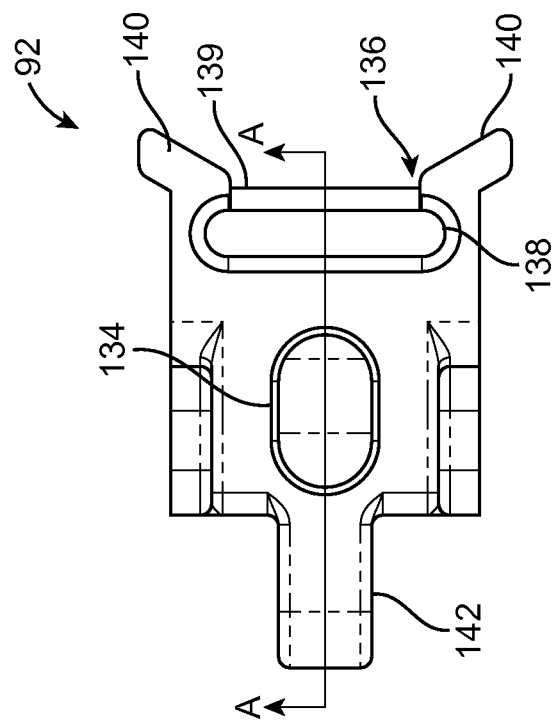
FIG. 15B is a top view of the blade mount according to the present invention.
Figure 15A:
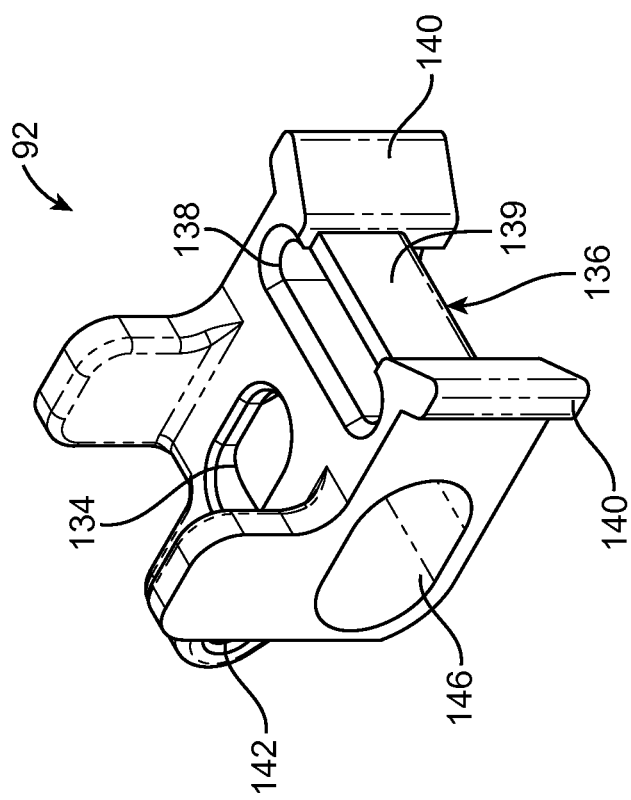
FIG. 15A is a top perspective view of the blade mount according to the present invention.

A blade mount 92 according to the present invention is shown in FIG. 15. The blade mount 92 is configured to connect to the blade mount portion 120 of the housing 90 and, in particular, pivotably attach to underneath the flange. The blade mount 92 includes an aperture 134 for receiving the distal end of the tow angle post 124. The blade mount 92 includes a blade receiving portion 136 configured to connect to a blade 26 according to the present invention. The blade receiving portion 136 includes an elongated or elliptical aperture 138 having a sidewall 139 that is configured to connect with therein a retractor blade 26 according to the present invention. Two outwardly extending flanges 140 serve to stabilize a blade 26 that is connected to the blade mount 92. The blade mount 92 includes an aperture 142 configured for receiving a pin 144 (see FIG. 12) there through. A corresponding pin aperture is formed in the housing 90 and configured to receive the pin to connect the blade mount 92 in a pivotable manner to the housing 90. An additional opening 146 of the slider 14 is formed as a window extending into the blade mount 92 and intersecting with the tow angle post aperture 122 for the attachment of tow angle return.

With a tow angle post 124 inserted into the threaded aperture 122 of the housing 90 and its distal non-threaded 132 and threaded portion 130 extending beyond the housing 90, the blade mount 92 is pivotably connected to the housing 90 by passing a pin 144 through the pin aperture 142 and by passing the aperture 134 of the blade mount 92 onto the distal portion of the tow angle post 124 such that the blade mount 92 is positioned on the non-threaded portion 132. The blade mount 92 is captured between the housing 90 and a tow angle return 148.

Turning now to FIG. 16, a tow angle return 148 will now be described. The tow angle return 148 is a spherically shaped element with a threaded aperture 150 configured to thread onto the distal threaded portion 130 of the tow angle post 124. When threaded onto the distal end of the tow angle post 124, the tow angle return 148 serves to capture the blade mount 92 between the tow angle return 148 and the housing 90. When the tow angle post 124 is threaded into the housing 90, the tow angle post 124 moves downwardly allowing the blade mount 92 to angulate about the pin 144 in a downward direction. When the tow angle post 124 is threaded up and outwardly from the housing 90, the tow angle post 124 moves upwardly with the tow angle return 148 contacting the blade mount 92 and pulling or angulating the blade mount 92 upwardly. Removal of the tow angle post 124 is prevented by the tow angle return 148 threaded onto the distal threaded portion 130 of the tow angle post 124.

Turning now to FIGS. 17a-17b, there is shown an antifriction bearing 94 according to the present invention. The bearing 94 is an elongated cylinder made of appropriate material such as surgical steel or titanium. The elongate cylinder has a circular cross-section and defines an outer surface 152 and an inner surface 154. The inner surface 154 forms a lumen extending between an open proximal end and an open distal end. FIG. 17b shows a pin 156 sized and configured for insertion into the lumen of the bearing 94. The length of the pin 156 is longer than the bearing 94 such that the proximal end and distal end of the pin 156 extend beyond the proximal and distal openings of the bearing 94, respectively. The bearings 94 are sized and configured to fit inside the bearing receiving portions 116 and the pin apertures 118 of the housing 90 to connect the bearing 94 to the housing 90 by welding the pins 156 to the housing 90 capturing the bearings 94 within the bearing receiving portions 116 such that the bearings 94 are free to rotate relative to the housing 90. Alternatively, a cage or other retainer can be employed to secure the antifriction bearings 94 to the housing 90. The antifriction bearing 94 is a cylindrical roller having straight sides that provide a line contact with the first rail 12. The cylindrical rollers are small and may be considered to be needle rollers. Other antifriction elements such as spherical or ball bearings can be used in combination or instead of the cylindrical roller bearings shown in the figures. The roller bearings 94 are disposed in the bearing receiving portions 116 and retained therein by bearing pins 156 welded to the housing 90. The cylindrical bearings 94 are connected to the housing 90 such that they can rotate about their respective pins 156 relative to the housing 90. When connected to the housing 90, the antifriction bearings 94 extend or protrude slightly into first rail receiving portion 100 to contact the first rail 12 disposed therein.

Figure 18A:
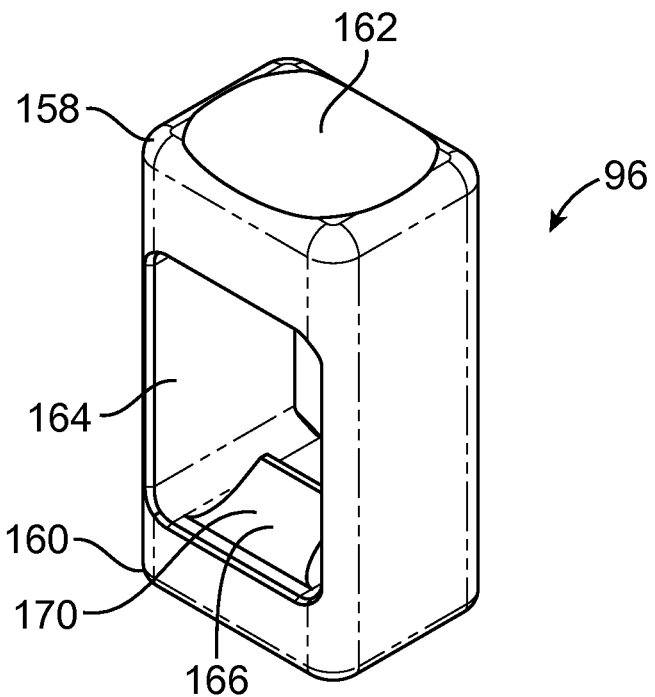
FIG. 18A is a top perspective view of a lock according to the present invention.
Figure 18B:
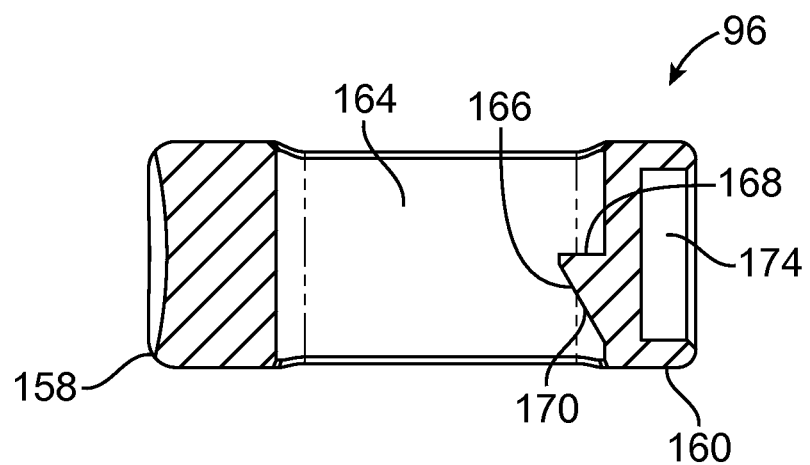
FIG. 18B is a cross-sectional view of a lock according to the present invention.

Turning now to FIGS. 18a-18b, there is shown a lock 96 according to the present invention. The lock 96 is sized and configured to be disposed inside the lock receiving portion 110 of the housing 90. The lock 96 is an elongate shape having a square or rectangular cross section having a first end 158 and a second end 160. The first end 158 includes an outer surface that extends beyond a side surface 108 of the housing 90 and is configured to be depressible by a finger of a user and as such may include a concave depression 162 for receiving a finger of a user. The lock 96 includes a throughway 164 extending through the lock 96 from one side surface to another side surface and is configured to receive the first rail 12. The throughway 164 includes an inner surface that includes a locking tooth 166. The locking tooth 166 extends from the inner surface and into the throughway 164. The protruding locking tooth 166 includes a locking surface or flank 168 that is substantially perpendicular with respect to the inner surface and an angled or ramped surface or flank 170 that is angled with respect to the inner surface of the lock 96.

The throughway 164 is sized and configured to receive the first rail 12 inside the throughway 164. Also, the locking tooth 166 is sized and configured to engage with the teeth 76 of the first track 58a of the first rail 12 such that the locking flank 168 of the locking tooth 166 engages the perpendicular flanks of the first track 58a. The angled flank 170 of the locking tooth 166 permits sliding engagement with the angled flanks of the first track 58a such that the locking tooth 166 serves as a unidirectional stop. The lock 96 includes a spring 172 depicted in FIG. 19 that is disposed between the lock 96 and the housing 90. In particular, the spring 172 is disposed in a spring receiving portion 174 formed at the second end 160 of the lock 96 with the opposite end of the spring 172 abutting the back wall or stop 114 formed at the inside end of the lock receiving portion 110. The lock receiving portion 110 may also include a spring receiving portion to receive the other end of the spring 172. The spring 172 is positioned to bias the lock 96 outwardly relative to the housing 90 such that the locking tooth 166 of the lock 96 is engaged with the teeth 76 of the rail 12.

The first slider 14 is assembled with respect to the first rail 12 by inserting the first rail 12 into the first rail receiving portion 100 of the housing 90. Before the first rail 12 crosses the lock receiving portion 110 of the housing, the lock spring 172 is disposed inside the lock receiving portion 110 followed by the lock 96 which is oriented such that the through-way 164 of the lock 96 is aligned with the first rail receiving portion 110. The lock 96 may have to be depressed slightly to pass the first rail 12 through the lock throughway 164. Hence, the lock 96 is captured by the first rail 12 inside the housing 90. The distal end 28 of the first rail 12 is passed through the housing 90 until the aperture 50 at first distal end 28 extends out from the housing 90. A stop pin 86 is then inserted into the aperture 50 to prevent the slider 14 from sliding off the first distal end 28. The first rail 12 is inserted into the first rail receiving portion 110 such that the teeth 76 of the first track 58a face inwardly towards the locking tooth 166 of the lock 96 for engagement therewith. The lock 96 is biased by the spring 172 such that the locking tooth 166 engages the teeth 76 of the track 58a. Since the lock 96 is movable by depressing the first end relative 158 to the housing 90 to thereby release the locking tooth 166 from the teeth 76 of the track 58a, the track 58a can then be moved along the rail 12 in any direction along the Y-axis. In the variation shown, the slider 12 is free to move outwardly toward the first distal end 28 of the first rail 12 with the locking tooth 166 engaged with the teeth 76 on the rail 12 by nature of the ramped locking tooth 166 engaging the angled flacks of the track 58a. This configuration permits the slider 12 to move outwardly toward the first distal end 28 while the locking tooth 166 is engaged with the track 58a but the lock prevents movement of the slider 12 inwardly away from the first distal end 28 as the perpendicular flank 168 of the locking tooth 166 and the perpendicular flank of the track 58a would engage each other to arrest movement of the first slider 14 relative to the first rail 12. This configuration allows the slider 14 to move outwardly to expand the tissue opening or wound area preventing the collapse of the tissue opening allowing users to take surgical action in the retracted zone. To close or move the slider 14 to close or reduce the retraction or tissue opening, the user would depress the first end 158 of the lock 96 to release the locking tooth 166 from engagement with the first track 58a. The first rail 12 does not contact the housing 90. Instead, the first rail 12 is configured to contact one or more antifriction bearings 94.

Figure 20:
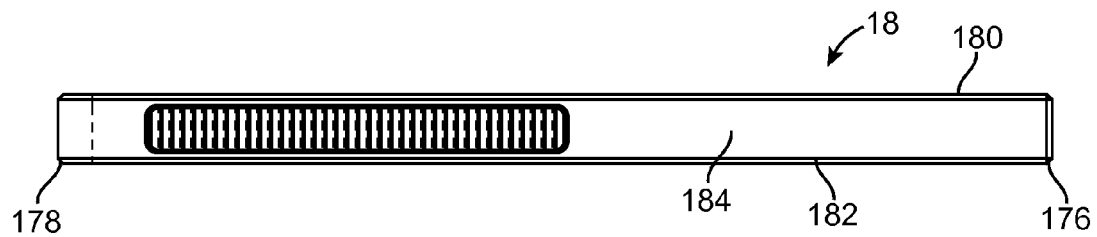
FIG. 20 is a side elevation view of the second rail according to the present invention.
Figure 21:
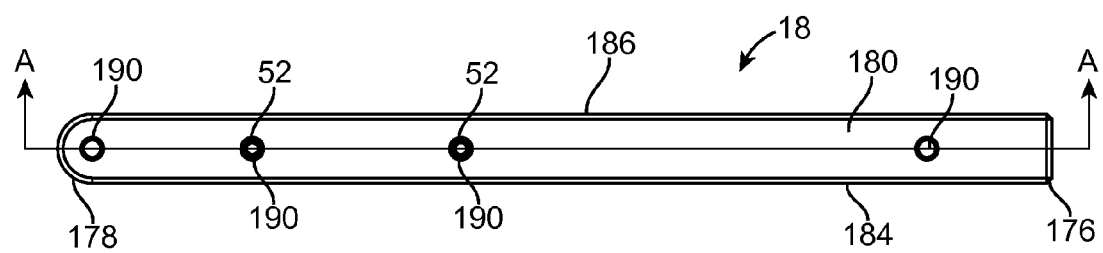
FIG. 21 is a top view of the second rail according to the present invention.
Figure 22:
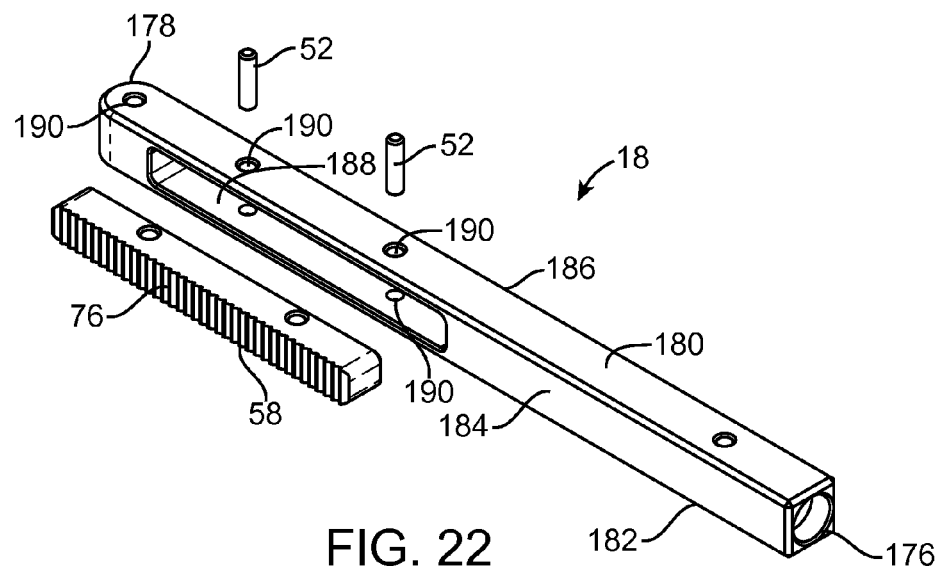
FIG. 22 is a top perspective exploded view of the second rail according to the present invention.
Figure 24B:
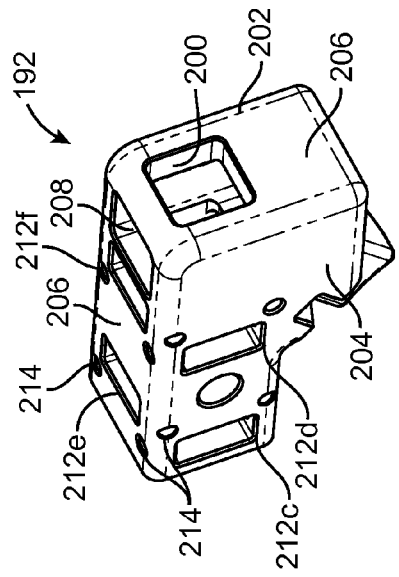
FIG. 24B is a bottom perspective view of the housing of the third slider according to the present invention.
Figure 24D:
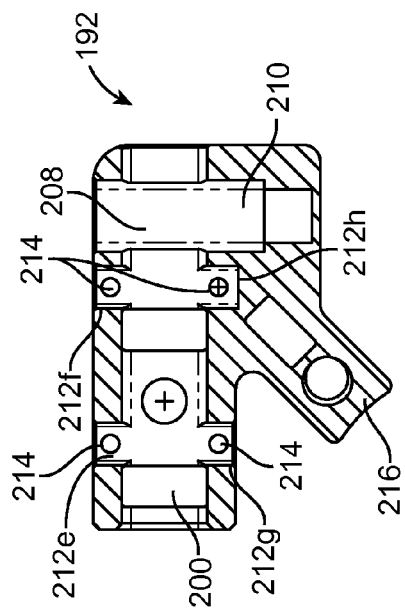
FIG. 24D is a cross-sectional view taken along line B-B of FIG. 24C of the housing of the third slider according to the present invention.
Figure 24A:
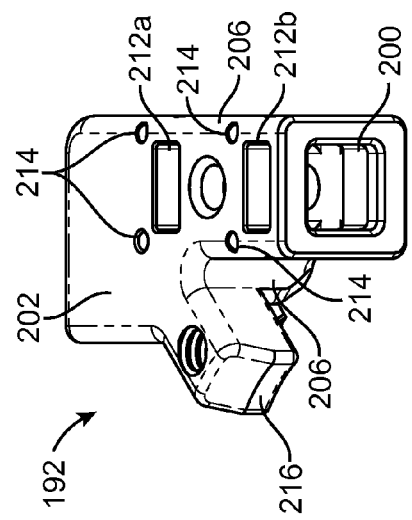
FIG. 24A is top perspective view of the housing of the third slider according to the present invention.
Figure 24C:
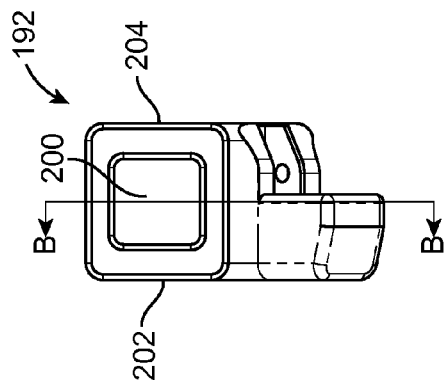
FIG. 24C is an end elevational view of the housing of the third slider according to the present invention.
Figure 26A:
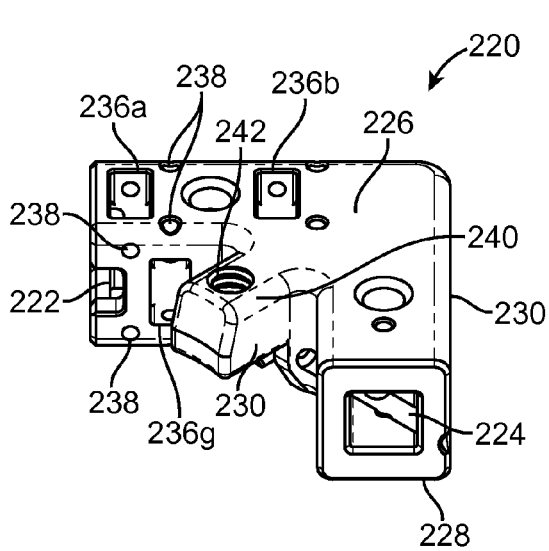
FIG. 26A is a top perspective view of the housing of the second slider according to the present invention.
Figure 26B:
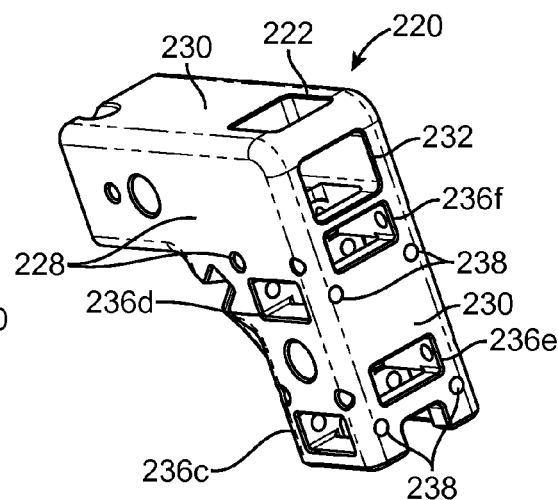
FIG. 26B is a bottom perspective view of the housing of the second slider according to the present invention.
Figure 26C:
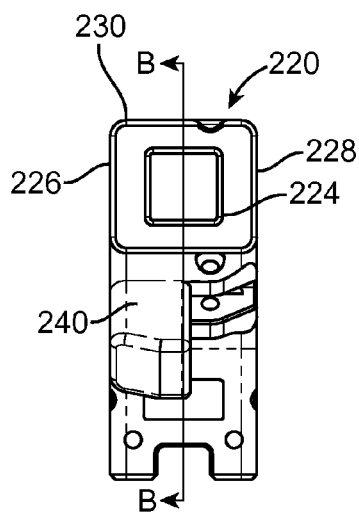
FIG. 26C is an end elevational view of the housing of the second slider according to the present invention.
Figure 26D:
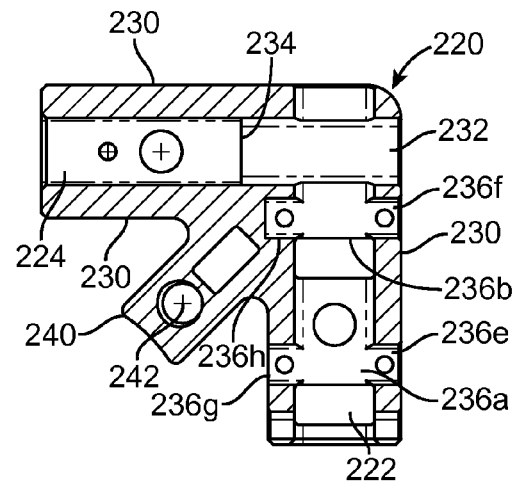
FIG. 26D is a cross-sectional view taken along line B-B of FIG. 26C of the housing of the second slider according to the present invention.

Turning now to FIGS. 20-22, there is shown a second rail 18 according to the present invention. The second rail 18 is an elongate, straight bar that is made of metal such as surgical steel or titanium. The second rail 18 includes a proximal end 176 and a distal end 178 and has a top surface 180 and a bottom surface 182 interconnected by an inner surface 184 and an outer surface 186 to define a substantially square or rectangular cross-section perpendicular to the longitudinal axis of the second rail 18. A curved end surface is formed at the distal end 178. The proximal end 176 of the second rail 18 is sized and configured to be received inside the second rail receiving portion 102 of the first slider 14. The second rail 14 is inserted into the second rail receiving portion 102 of the first slider 14 and pins 52 are passed through apertures in the first slider 14 and second rail 18 and welded to connect the second rail 18 to the first slider 14. Because the second rail receiving portion 102 is perpendicular to the first rail receiving portion 100, the second rail 18 will be perpendicular to the first rail 12 when connected to the first slider 14. Movement of the first slider 14 will result in movement of the second rail 18 along with the first slider 14.

The second rail 18 includes at least one track 58. The track 58 is the same as described above with respect to FIGS. 8-10. The track 58 is disposed in a track-receiving portion 188 of the second rail 18. The track-receiving portion 188 is sized and configured to receive the track 58. Pins 52 are passed through apertures 190 in the top surface 180 and bottom surface 182 of the second rail 18 and through pin apertures 74 in the track 58. The pins 52 are laser welded to connect the track 58 to the second rail 18. Teeth 76 on the track 58 are configured to engage a locking tooth on the third slider 22 such that movement of the third slider 22 with respect to the second rail 18 is prevented or locked. In the variation shown in the figures, the third slider 22 is permitted to travel in one direction and locked in the opposite direction while the locking tooth of the third slider 22 is engaged with the teeth 76 of the track 58. In such a variation, the flanks are of the locking tooth and track are configured to permit ramped travel over the teeth in one direction and configured to lock against perpendicular flanks in the opposite direction. Preferably the teeth 76 on the track 58 and the locking tooth on the third slider 22 are configured to lock or prevent the third slider 22 from moving toward the first slider 14 while the locking tooth of the third slider 22 is engaged with the teeth 76 on the track 58. This configuration advantageously permits the retraction zone to be easily opened increased in size by moving the third slider 22 outwardly away from the first slider 14 without requiring release or disengagement of the locking tooth. This configuration also advantageously prevents the third slider 22 from creeping toward the first slider 14 and reducing the size of the retracted opening.

Still referencing FIGS. 20-22, the track 58 provides the second rail 18 with a toothed surface that is recessed from the inner surface 184 of the second rail 18. The teeth 76 do not protrude or extend beyond the outer surface of the second rail 18. In one variation, the top land of each tooth is even with the inner surface 184 of the second rail 18. In another variation, the top land is slightly recessed or setback from the inner surface 184 of the second rail 18. In general, the right or left flanks do not protrude beyond the inner surface 184 of the second rail 18. Thereby, the track 58 is set within the track receiving portion 188. In another variation, the second rail 18 does not include a track 58 located within track receiving portion 188; instead, the second rail 18 itself is provided with at least one toothed surface recessed as described above and integrally formed with the second rail 18 instead of as separate insertable track 58. Furthermore, the at least one toothed surface can be located along one or more surfaces of the second rail 18 such as the top surface 180, bottom surface 182, inner surface 184 and/or outer surface 186.

The track 58 is located proximally to the distal end 178 of the second rail 18 such that the flanks of all of the teeth on the track 58 are configured to permit unidirectional travel of the third slider 22 in a direction parallel to the X-axis and away from the first slider 14 and toward the distal end 178 while the locking tooth of the third slider 22 is engaged. Hence, the left flanks of all of the teeth on the track 58 are perpendicular to the baseline 84 or top land 82 and the right flanks are angled to permit the third slider 22 to move outwardly toward the distal end 178 but prevent or restrict movement of the third slider 22 toward the first slider 14 or the proximal end 176 of the second rail 18.

Still referencing FIGS. 20-22, the second rail 18 includes an aperture 190 near the distal end 178 extending from the top surface 180 to the bottom surface 182 of the second rail 18 and configured to receive a stop pin 86 having an enlarged head 88 as shown and described in FIG. 11. The enlarged head 88 is not flush but is positioned above the top surface 180 when the stop pin 86 is in place and serves to stop the sliding motion of the third slider 22 preventing it from moving off the second rail 18. The stop pin 86 is placed after the third slider 22 is connected to the second rail 18. The third slider 22 is arrested when traveling toward the first slider 14 by abutting the first slider 14 itself.

Turning now to FIGS. 23-24, the third slider 22 will now be described. The third slider 22 includes a housing 192, a blade mount 92, a plurality of antifriction bearings 94 and a lock 96 (see FIG. 18).

The housing 192 of the third slider 22 will now be described with reference to FIGS. 24a-24d. The housing 192 is made of any suitable material including any metal such as steel, surgical steel or titanium and defines a second rail receiving portion 200. The housing 192 has a top surface 202 and a bottom surface 204 interconnected by a plurality of side walls having side surfaces 206 to the outside to define the housing 192. The second rail receiving portion 200 is formed as a passageway sized and configured to receive the second rail 18 in sliding engagement with the housing 192. The second rail receiving portion 200 includes a first opening formed in a side surface 206 at one end of the housing 192 and a second opening formed in a side surface at a second end of the housing 192 directly opposite from the first opening to define a passageway extending therebetween. The passageway has a cross-sectional area that is slightly larger than the cross-sectional area of the second rail and a cross-sectional shape that is the same as the cross-sectional shape of the second rail 18.

The housing 192 of the third slider 22 further includes a lock receiving portion 208. The lock receiving portion 208 is sized and configured to receive a lock 96 therein. The lock receiving portion 208 intersects with the second rail receiving portion 200, preferably, at approximately 90 degrees. The lock receiving portion 208 includes an opening in a side surface 206 of the housing 192 and defines a passageway extending inwardly from the opening into the housing 192. The lock receiving portion 208 traverses or crosses the second rail receiving portion 200. The lock receiving portion 208 includes a back wall or stop 210 formed at the inside end of the lock receiving portion 208.

Still referencing FIGS. 21a-24d, the housing 192 of the third slider 22 further includes one or more bearing receiving portions 212 along at least two sides of the second rail receiving portion 200 and interconnecting with the second rail receiving portion 200. The bearing receiving portions 212 are shown to be square or rectangular in shape, although they can have any cross-sectional shape and be curved or rounded so long as they are configured to receive antifriction bearings 94. One side of each of the square or rectangular shaped bearing receiving portion 212 is open to the second rail receiving portion 200 such that when an antifriction bearing 94 is inserted in the bearing receiving portion 212 it provides a point or line contact with the second rail 18. In the variation shown in FIGS. 24a-24d, there are a total of eight bearing receiving portions adjacent to the second rail receiving portion 200 configured to support the second rail 18. Two bearing receiving portions 212a, 212b are located above the second rail receiving portion 200 and generally adjacent to the top 180 of the second rail 18 when it is inserted and two bearing receiving portions 212c, 212d are located below the second rail receiving portion 200 and generally adjacent to the bottom surface 182 of the second rail 18 when it is inserted. Hence, there are four bearing receiving portions 212a, 212b, 212c, 212d each having a longitudinal axis that is parallel to the Y-axis or otherwise perpendicular to the longitudinal length of the second rail 18 when the second rail 18 is inserted inside the housing 192. The housing 192 further includes pin apertures 214 opening to the side surfaces 206 on either side of the second rail receiving portion 200. The pin apertures 214 extend inwardly to interconnect with the bearing receiving portions 212 and are configured to hold the antifriction bearings 94 in position. The pin apertures 214 have a cross-sectional area that is smaller than the cross-sectional area of the bearing receiving portions 212 taken perpendicular to the longitudinal axes of the bearing receiving portions or Y-axis.

Furthermore, two bearing receiving portions 212e, 212f are located along one side of second rail receiving portion 200 and generally adjacent to the outer surface 186 of the second rail 18 when it is inserted and two bearing receiving portions 212g, 212h are located along and generally adjacent to the inner surface 184 of the second rail 18 when it is inserted. Hence, there are four bearing receiving portions 212e, 212f, 212g, 212h each having a longitudinal axis that is parallel to the Z-axis or otherwise perpendicular to the longitudinal length of the second rail 18 when the second rail 18 is inserted into the housing 192. Pin apertures 214 extend inwardly to interconnect with the bearing receiving portions 212 and are configured to hold the antifriction bearings 94 in position.

The housing 192 of the third slider 22 further includes a blade mount portion 216. The blade mount portion 216 is configured to connect to a blade mount 92. The blade mount portion 216 of the housing 192 is configured as a flange that extends outwardly from the housing 192. In the variation shown in FIGS. 24a-24d, the blade mount portion 216 is located inwardly toward the center of the retractor such that the flange extends between and at an angle to the second rail receiving portion 200. The blade mount portion 216 includes a threaded aperture 218 configured to receive a threaded tow angle post 124 of the same or similar kind described with reference to FIG. 14. The tow angle post 124 is configured to be threadingly inserted into the threaded aperture 218 of the blade mount portion 216 of the housing 192. With the tow angle post 124 inserted, a blade mount 92 of the same kind as described in FIG. 15 is connected in the same manner. A blade mount 92 is the same as that described with reference to FIG. 15. The blade mount 92 is captured between the housing 192 and a tow angle return 148 as described above. The tow angle return 148 is threaded onto the distal end of the tow angle post 124.

Antifriction bearings 94 and bearing pins 156 of the same kind described in reference to FIGS. 17a-17b are disposed inside the bearing receiving portions 212 and retained therein by bearing pins 156 welded to the housing 192. The cylindrical bearings 94 are connected to the housing 192 such that they can rotate about their respective pins 156 relative to the housing 192.

Figure 19:
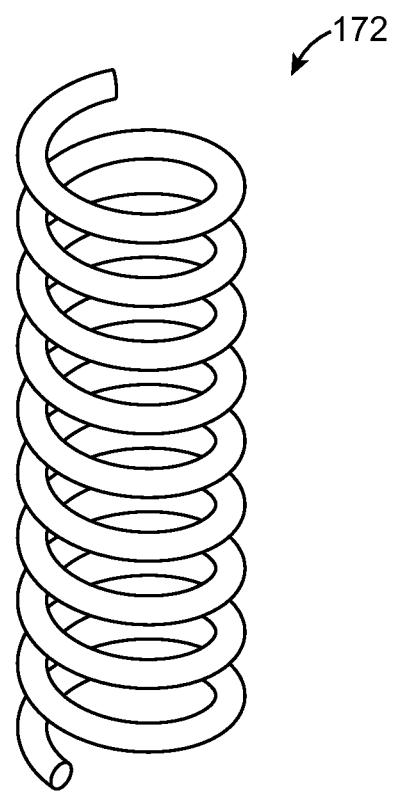
FIG. 19 is a top perspective view of the lock spring according to the present invention.

A lock 96 of the same kind as described in reference to FIGS. 18-19 is disposed inside the lock receiving portion 208 of the third housing 192. The locking tooth 166 extends from the inner surface and into the through-way 164 of the lock 96. The protruding locking tooth 166 includes a locking surface that is substantially perpendicular with respect to the inner surface and an angled or ramped surface that is angled with respect to the inner surface of the lock. The through-way is sized and configured to receive the second rail 18 inside the through-way 164. Also, the locking tooth 166 is sized and configured to engage with the teeth 76 of the track 58 of the second rail 18 such that the locking surface of the locking tooth 166 engages the perpendicular flanks of the track 58. The angled surface of the locking tooth 166 permits sliding engagement with the angled flanks of the track 76 such that the locking tooth 166 serves as a unidirectional stop. The lock 96 includes a spring 172 that is disposed between the lock 96 and the third housing 192 to bias the locking tooth 166 into the teeth 76 of the track 58 in the second rail 18.

The third slider 192 is assembled with respect to the second rail 18 by inserting the second rail 18 into the second rail receiving portion 200 of the third housing 192. Before the second rail crosses the lock receiving portion 208 of the housing, the lock spring 172 is disposed inside the lock receiving portion 208 followed by the lock 96 which is oriented such that the through-way 164 of the lock 96 is aligned with the second rail receiving portion 200. The lock 96 may have to be depressed slightly to pass the second rail 18 through the lock throughway 164. The lock 96 is captured by the second rail 18 residing inside the third housing 192. The distal end 178 of the second rail 18 is passed through the third housing 192 until the aperture 190 at first distal end 178 extends out from the third housing 192. A stop pin 86 is then inserted into the aperture to prevent the third slider 22 from sliding off the second rail 18. The second rail 18 is inserted into the second rail receiving portion 200 such that the teeth 76 of the track 58 face inwardly towards the locking tooth 166 of the lock 96 for engagement therewith. The lock 96 is biased by the spring 172 such that the locking tooth 166 engages the teeth 76 of the track 58. Since the lock 96 is movable by depressing the first end 158 relative to the housing 192 to thereby release the locking tooth 166 from the teeth 76 of the track 58, the third slider 22 can then be moved relative to the second rail 18 in any direction along the X-axis. In the variation shown, the third slider 22 is free to move outwardly toward the distal end 178 of the second rail 18 by nature of the ramped locking tooth 166 engaging the angled flanks of the track 58 as described above. This configuration permits the third slider 22 to move outwardly toward the first distal end 178 but the lock 96 prevents movement of the third slider 22 inwardly away from the first distal end 178 as the perpendicular surface of the locking tooth 166 and the perpendicular flank of the track 58 would engage each other to arrest movement of the third slider 22 relative to the second rail 18. This configuration allows the third slider 22 to move outwardly to expand the tissue opening or wound area preventing the collapse of the tissue opening allowing users to take surgical action in the retracted zone. To close or move the third slider 22 to close or reduce the retraction or tissue opening, the user would depress the first end 158 of the lock 96 to release the locking tooth 166 from engagement with the recessed track 58. With the lock 96 depressed to disengage the locking tooth 166, the second rail 18 does not contact the third slider 22. Instead, the second rail 18 contacts one or more of the antifriction bearings 94.

Turning now to FIGS. 25-26, the second slider 16 will now be described. The second slider 16 is a mirror image of the first slider 14. The second slider 16 is mounted on the second distal end 30 of the first rail 12 and includes a housing 220, a blade mount 92, a plurality of antifriction bearings 94 and a lock 96 (see FIGS. 18a-18b).

The housing 220 is made of any suitable material including any metal such as steel, surgical steel, or titanium and defines a first rail receiving portion 222 and a third rail receiving portion 224. The housing is polygonal in shape forming a L-shaped structure having a top surface 226 and a bottom surface 228 interconnected by a plurality of side walls having side surfaces 230 to the outside to define the housing 220. The first rail receiving portion 222 is formed as a passageway sized and configured to receive the first rail 12 in sliding engagement therein. The passageway of first rail receiving portion 222 includes a first opening formed in a side surface 230 at one end of the housing 220 and extends to a second opening formed in a side surface 230 at a second end of the housing 220 directly opposite from the first opening to define the passageway. The passageway has a cross-sectional area that is slightly larger than the cross-sectional area of the first rail 12 and a cross-sectional shape that is the same as the cross-sectional shape of the first rail 12.

The housing 220 includes a third rail receiving portion 224. The third rail receiving portion 224 is formed as a passageway that is sized and configured to receive the third rail 20 therein. The passageway of third rail receiving portion 224 includes a first opening formed in a side surface 230 at one end of the housing 220. A second opening formed in a side surface 230 at a second end opposite the first opening is optional as an alternative variation. The passageway extends from the first opening into the housing 220 and does not necessarily have to extend or open to the second surface opposite the first opening. The passageway has a cross-sectional area that is slightly larger than the cross-sectional area of the third rail 20 and a cross-sectional shape that is the same as the cross-sectional shape defined by the third rail 20. The first rail receiving portion 222 and the third rail receiving portion 224 are shown to be perpendicular to each other with the first rail receiving portion 222 substantially parallel to the Y-axis and the third rail receiving portion 224 substantially parallel to the X-axis. Although the first and third rail receiving portions 222, 224 are shown to be configured at 90 degrees to each other the invention is not so limited and the first and third rail receiving portions 222, 224 can be angle with respect to each other. For example, the angle between the first and third rail-receiving portions 222, 224 can be acute at approximately 30 degrees as angled as far apart as approximately 150 degrees.

The housing 220 further includes a lock receiving portion 232. The lock receiving portion 232 is sized and configured to receive a lock 96 therein. The lock receiving portion 232 intersects with the first rail receiving portion 222, preferably, at approximately 90 degrees. The lock receiving portion 232 includes an opening in a side surface 230 of the housing 220 and defines a passageway extending inwardly from the opening and into the housing 220. The lock receiving portion 232 traverses or crosses the first rail receiving portion 222. The lock receiving portion 222 includes a back wall or stop 234 formed at the inside end of the lock receiving portion 232. In the variation shown in FIGS. 26a-26d, the lock receiving portion 232 is aligned with the third rail receiving portion 224, both being perpendicular to the first rail receiving portion 222.

Still referencing FIGS. 26a-26d, the housing 220 further includes one or more bearing receiving portions 236 along at least two sides of the first rail receiving portion 222 and interconnecting with the first rail receiving portion 222 such that antifriction bearings inserted into the bearing receiving portion 236 contact the first rail 12. The bearing receiving portions 236 are shown to be square or rectangular in shape, although they can have any cross-sectional shape and be curved or rounded. One side of each of the square or rectangular shaped bearing receiving portion 236 is open to the first rail receiving portion 222 such that when an antifriction bearing 94 is inserted in the bearing receiving portion 236 it provides a point or line contact with the first rail 12. In the variation shown in FIGS. 25-26, there are a total of eight bearing receiving portions 236 adjacent to the first rail receiving portion 222. Two bearing receiving portions 236a, 236b are located above the first rail receiving portion 222 and generally adjacent to the top surface 32 of the first rail 12 when it is inserted. Two bearing receiving portions 236c, 236d are located below the first rail receiving portion 222 and generally adjacent to the bottom surface 34 of the first rail 12 when it is inserted. Hence, there are four bearing receiving portions 236a, 236b, 236c, 236d each having a longitudinal axis that is parallel to the X-axis or otherwise perpendicular to the longitudinal length of the first rail 12 when it is inserted. The housing 220 further includes pin apertures 238 opening to the side surfaces 230 on either side of the first rail receiving portion 222. The pin apertures 238 extend inwardly to interconnect with the bearing receiving portions 236 and hold the antifriction bearings 94 in position. The pin apertures 238 have a cross-sectional area that is smaller than the cross-sectional area of the bearing receiving portions 236 taken perpendicular to the longitudinal axes of the bearing receiving portions 236.

Furthermore, two bearing receiving portions 236e, 236f are located along one side of first rail receiving portion 222 and generally adjacent to the outer surface 38 of the first rail 12 when it is inserted and two bearing receiving portions 236g, 236h are located along the opposite or other side of the first rail receiving portion 222 and generally adjacent to the inner surface 36 of the first rail 12 when it is inserted. Hence, there are four bearing receiving portions 236e, 236f, 236g, 236h each having a longitudinal axis that is parallel to the Z-axis or otherwise perpendicular to the longitudinal length of the first rail 12 when it is inserted. The housing 220 further includes pin apertures 238 opening to the top and bottom surfaces 226, 228 on either side of the first rail receiving portion 222. The pin apertures 238 extend inwardly to interconnect with the bearing receiving portions 236 and hold the antifriction bearings 94 in position. The pin apertures 238 have a cross-sectional area that is smaller than the cross-sectional area of the bearing receiving portions 222 taken perpendicular to the longitudinal axes of the bearing receiving portions 222 or Z-axis.

The housing 220 further includes a blade mount portion 240. The blade mount portion 240 is configured to connect to a blade mount 92. The blade mount portion 240 of the housing 220 is configured as a flange that extends outwardly from the housing 220 and toward the retractor zone. The blade mount portion 240 is located in the seat of an L-shaped housing 220 such that the flange extends between and at an angle to the first rail receiving portion 222 and the third rail receiving portion 224. The blade mount portion 240 includes a threaded aperture 242 configured to receive a threaded tow angle post 124.

The tow angle post 124 is the same as described with reference to FIG. 14. The tow angle post 124 is configured to be threadingly inserted into the threaded aperture 242 of the blade mount portion 240 of the housing 220. A blade mount 92 shown and described in reference to FIG. 15 is configured to connect to the blade mount portion 240 of the housing 220 and in particular pivotably attach to underneath the flange as described above. The blade mount 92 is captured between the housing 220 and a tow angle return 148 as described with respect to FIG. 16.

Antifriction bearings 94 such as the roller bearings 94 as described above with reference to FIG. 17 are disposed in the bearing receiving portions 236 and retained therein by bearing pins 156 welded to the housing 220. The cylindrical bearings 94 are connected to the second slider 16 such that they can rotate about their respective pins relative to the housing 220. When connected to the housing 220 of the second slider 16, the antifriction bearings 94 extending slightly into first rail receiving portion 222.

A lock 96 as described with reference to FIG. 18 is disposed inside the lock receiving portion 232 of the housing 220 and configured such that the locking tooth 166 is spring biased to engage the teeth 76 of the third rail 20. In one variation, the lock 96 is configured to prevent movement of the second slider 16 relative to the first rail 12 unless the lock 96 is depressed against the spring 19 to disengage the locking tooth 166 from the teeth 76 on the first rail 12. In another variation, the teeth 76 on the first rail 12 are configured or angled with respect to the locking tooth 166 such that unidirectional travel of the second slider 16 is permitted while the without disengaging the lock 96 from being in contact with the first rail 12. Preferably, unidirectional travel of the second slider 16 in a direction away from the handle 44 is permitted and movement toward the handle is prevented or locked. The angled surface of the locking tooth 166 permits sliding engagement with the angled flanks of the second track 58b such that the locking tooth 166 serves as a unidirectional stop.

The second slider 16 is assembled with respect to the first rail 12 in the same manner as the first slider 14 is assembled with respect to the first rail 12 with the lock 96 being captured by the first rail 12 inside the housing 220. A stop pin 86 prevents the second 16 slider from sliding off the second distal end 30 of the first rail 12. The first rail 12 is inserted into the first rail receiving portion 222 such that the teeth 76 of the second track 58b face inwardly towards the locking tooth 166 of the lock 96 for engagement therewith. The lock 96 is biased by the spring 172 disposed between the lock 96 and the housing 220 such that the locking tooth 166 engages the teeth 76 of the second track 58b. Since the lock 96 is movable by depressing the first end 158 relative to the housing 220 to thereby release the locking tooth 166 from the teeth 76 of the track 58, the second slider 16 can then be moved along the first rail 12 in any direction along the Y-axis. In the variation shown, the second 16 slider is free to move outwardly toward the second distal end 30 of the first rail 12 with the locking tooth 166 engaged with the teeth 76 on the first rail 12 by nature of the ramped locking tooth arrangement relative to the angled flank arrangement of the second track 58b. This configuration permits the second slider 16 to move outwardly toward the second distal end 30 but the lock 96 prevents movement of the second slider 16 inwardly away from the second distal end 30 as the perpendicular surface of the locking tooth 166 and the perpendicular flank of the track 58b would engage each other to arrest movement of the second slider 16 relative to the first rail 12 with the locking tooth 166 engaged. This configuration allows the second slider 16 to move outwardly to expand the tissue opening or wound area preventing the collapse of the tissue opening allowing users to take surgical action in the retracted zone. To close or move the second slider 16 to close or reduce the retraction or tissue opening, the user would depress the first end 158 of the lock 96 to release the locking tooth 176 from engagement with the second track 58b. The first rail 12 does not contact the housing 220. Instead, the first rail 12 contacts one or more antifriction bearings 94 in sliding engagement therewith.

The third rail 20 is the same as the second rail 18 shown and described in reference to FIGS. 20-22. The proximal end of the third rail 20 is sized and configured to be received inside the third rail receiving portion 224 of the second slider 16. The third rail 20 is inserted into the third rail receiving portion 224 of the second slider 16 and pins are passed through apertures in the second slider 16 and third rail 20 and welded to connect the third rail 20 to the second slider 16. Because the third rail receiving portion 224 is perpendicular to the first rail receiving portion 222, the third rail 20 will be perpendicular to the first rail 12 when connected to the second slider 16. Movement of the second slider 16 will result in movement of the second rail 20 along with the second slider 16.

The third rail 20 includes at least one track 58. The track 58 is the same as described above with respect to FIGS. 8-10 and disposed in a track-receiving portion of the third rail 20. The track 58 provides the third rail 20 with a toothed surface that is recessed from the inner surface of the third rail 20. The teeth 76 do not protrude or extend beyond the outer surface of the third rail 20. Thereby, the track 58 is set within the third rail 20 and located proximally to the distal end of the third rail 20. The third rail 20 is also provided with a stop pin 86 as described above with respect to FIG. 11 which serves to stop the sliding motion of the fourth slider 24 from moving off the third rail 20. The fourth slider 24 is arrested when traveling toward the second slider 16 by abutting the second slider 16 itself.

Figure 27:
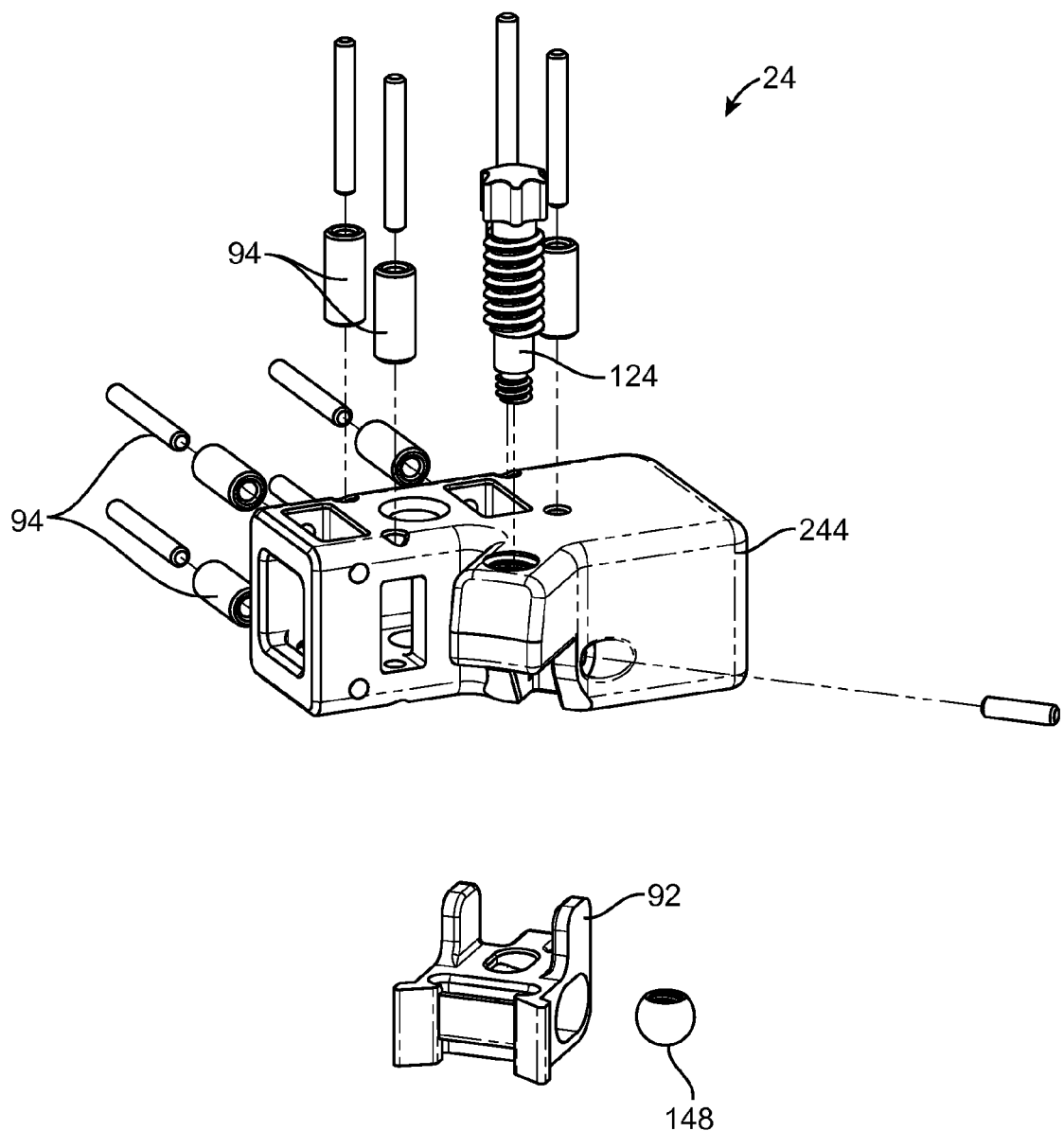
FIG. 27 is a top perspective exploded view of the fourth slider according to the present invention.
Figure 28A:
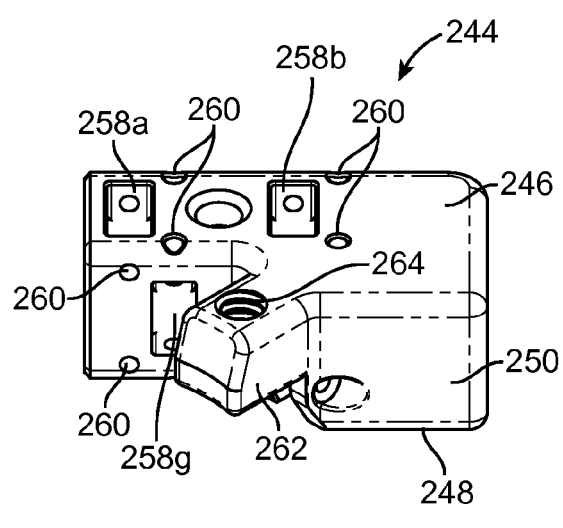
FIG. 28A is a top perspective view of the housing of the fourth slider according to the present invention.
Figure 28B:
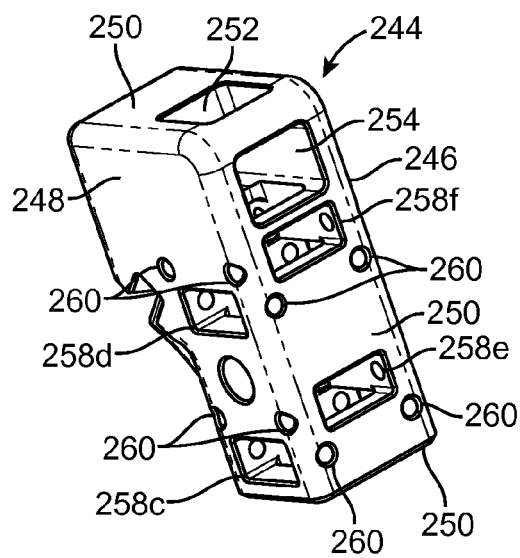
FIG. 28B is a bottom perspective view of the housing of the fourth slider according to the present invention.
Figure 28C:
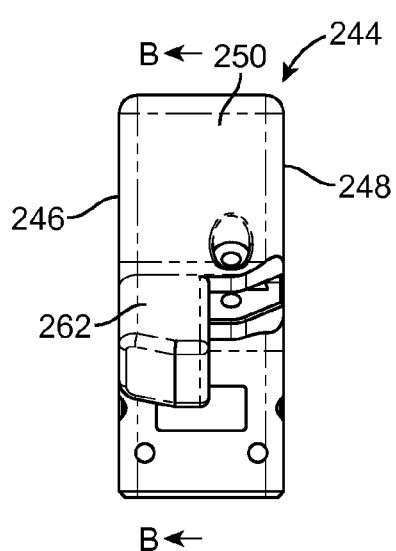
FIG. 28C is an end elevational view of the housing of the fourth slider according to the present invention.
Figure 28D:
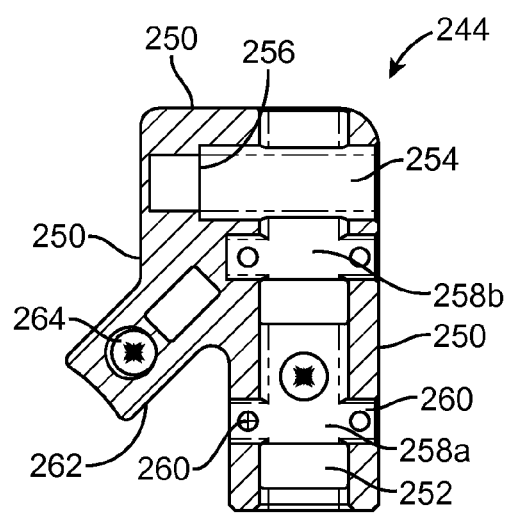
FIG. 28D is a cross-sectional view taken along line B-B of FIG. 28C of the housing of the fourth slider according to the present invention.

Turning now to FIGS. 27-28, the fourth slider 24 will now be described. The fourth slider 24 includes a housing 244, and a blade mount 92, a plurality of antifriction bearings 94 and a lock 96 connected to the housing 244.

The housing 244 of the fourth slider 24 will now be described with reference to FIGS. 28a-28d. The housing 244 is made of any suitable material including any metal such as steel, surgical steel, or titanium. The housing 244 is the same as but a mirror image of the housing 192 of the third slider 22 shown and described with respect to FIGS. 23-24. The housing 244 has a top surface 246 and a bottom surface 248 interconnected by a plurality of side walls having side surfaces 250 to the outside to define the housing 244. The housing 244 includes a third rail receiving portion 252 that is formed as a passageway sized and configured to receive the third rail 20 in sliding engagement with the housing 244. The third rail receiving portion 252 includes a first opening formed in a side surface 250 at one end of the housing 244 and a second opening formed in a side surface 250 at a second end of the housing 244 directly opposite from the first opening to define a passageway extending therebetween. The passageway has a cross-sectional area that is slightly larger than the cross-sectional area of the third rail 20 and a cross-sectional shape that is the same as the cross-sectional shape of the third rail 20.

The housing 244 of the fourth slider 24 further includes a lock receiving portion 254. The lock receiving portion 254 is sized and configured to receive a lock 96 therein of the type described in reference to FIG. 18. The lock receiving portion 254 intersects with the third rail receiving portion 252, preferably, at approximately 90 degrees. The lock receiving portion 254 includes an opening in a side surface of the housing 244 and defines a passageway extending inwardly from the opening into the housing 244. The lock receiving portion 254 traverses or crosses the third rail receiving portion 254. The lock receiving portion 254 includes a back wall or stop 256 formed at the inside end of the lock receiving portion 254.

Still referencing FIGS. 27-28, the housing 244 of the fourth slider 24 further includes one or more bearing receiving portions 258 along at least two sides of the third rail receiving portion 252 and interconnecting with the third rail receiving portion 252. The bearing receiving portions 258 are shown to be square or rectangular in shape, although they can have any cross-sectional shape and be curved or rounded. One side of each of the square or rectangular shaped bearing receiving portion 258 is open to the third rail receiving portion 252 such that when an antifriction bearing 94 is inserted in the bearing receiving portion 258 it provides a point or line contact with the third rail 20. In the variation shown in FIGS. 28a-28d, there are a total of eight bearing receiving portions 258 adjacent to the third rail receiving portion 252. Two bearing receiving portions 258a, 258b are located above the third rail receiving portion 252 and generally adjacent to the top surface of the third rail 20 when it is inserted. Two bearing receiving portions 258c, 258d are located below the third rail receiving portion 252 and generally adjacent to the bottom of the third rail 20 when it is inserted. Hence, there are four bearing receiving portions 258a, 258b, 258c, 258d each having a longitudinal axis that is parallel to the Y-axis or otherwise perpendicular to the longitudinal length of the third rail 20 when it is inserted. The housing 244 further includes pin apertures 260 opening to the side surfaces 250 on either side of the third rail receiving portion 252. The pin apertures 260 extend inwardly to interconnect with the bearing receiving portions 258 and are configured to hold the antifriction bearings 94 in position. The pin apertures 260 have a cross-sectional area that is smaller than the cross-sectional area of the bearing receiving portions 258 taken perpendicular to the longitudinal axes of the bearing receiving portions 258.

Furthermore, two bearing receiving portions 258e, 258f are located along one side of third rail receiving portion 252 and generally adjacent to the outer surface of the third rail 20 when it is inserted. Two additional bearing receiving portions 258g, 258h are located along the opposite or other side of the third rail receiving portion 252 and generally adjacent to the inner surface of the third rail 20 when it is inserted. Hence, there are four bearing receiving portions 258e, 258f, 258g, 258h each having a longitudinal axis that is parallel to the Z-axis or otherwise perpendicular to the longitudinal length of the third rail 20 when inserted. The housing 244 further includes pin apertures 260 opening to the top and bottom surfaces 246, 248 on either side of the third rail receiving portion 252. The pin apertures 260 extend inwardly to interconnect with the bearing receiving portions 258 and are configured to hold the antifriction bearings 94 in position.

The housing 244 of the fourth slider 24 further includes a blade mount portion 262. The blade mount portion 262 is configured to connect to a blade mount 92. The blade mount portion 262 of the housing 244 is configured as a flange that extends outwardly from the housing 244. In the variation shown in FIGS. 28a-28d, the blade mount portion 162 is located inwardly toward the center of the retractor 10 such that the flange extends between and at an angle to the third rail receiving portion 252. The blade mount portion 262 includes a threaded aperture 264 configured to receive a threaded tow angle post 124 of the same or similar kind described with reference to FIG. 14. The tow angle post 124 is configured to be threadingly inserted into the threaded aperture 264 of the blade mount portion 262 of the housing 244 to attach a blade mount 92 of the type described with reference to FIG. 15 to the housing 244 capturing the blade mount 92 with a tow angle return 148 shown and described with reference to FIG. 16.

Antifriction bearings 94 and bearing pins 156 of the kind described in reference to FIGS. 17a-17b are disposed inside the bearing receiving portions 258 and retained therein by bearing pins 156 welded to the housing 244. The cylindrical roller bearings 94 are connected to the housing 244 such that they can rotate about their respective pins 156 relative to the housing 244.

A lock 96 of the same kind described in reference to FIG. 18 is disposed inside the lock receiving portion 254 of the housing 244. The throughway 164 of the lock 96 is sized and configured to receive the third rail 20 inside the throughway 164. Also, the locking tooth 166 is sized and configured to engage with the teeth 76 of the track 58 of the third rail 20. The angled surface of the locking tooth 166 permits sliding engagement with the angled flanks of the track 58 such that the locking tooth serves as a unidirectional stop while the lock 96 is engaged with the track 58. The lock 96 includes a spring 172 that is disposed between the lock 96 and the housing 244. In particular, the spring 172 is disposed in a spring receiving portion 174 formed at the second end 160 of the lock 96 with the opposite end of the spring abutting the back wall or stop 256 formed at the inside end of the lock receiving portion 254. The lock receiving portion 254 may also include a spring receiving portion to receive the other end of the spring 172. The spring is positioned to bias the lock 96 outwardly relative to the housing 244 to engage the locking tooth 166 to the track 58 of the third rail 20.

The fourth slider 24 is assembled with respect to the third rail 20 by inserting the third rail 20 into the third rail receiving portion 252 of the housing 244. Before the third rail 20 crosses the lock receiving portion 254 of the housing 244, the lock spring 172 is disposed inside the lock receiving portion 254 followed by the lock 96 which is oriented such that the through-way 164 of the lock 96 is aligned with the third rail receiving portion 252. The lock 96 is captured by the third rail 20 residing inside the housing 244. The distal end of the third rail 20 is passed through the housing 244 until the aperture at distal end extends out from the housing 244 and a stop pin 86 is then inserted into the aperture to prevent the fourth slider 24 from sliding off the third rail 20. The third rail 20 is inserted into the third rail receiving portion 252 such that the teeth 76 of the track 58 face inwardly towards the locking tooth 166 of the lock 96 for engagement therewith. The lock 96 is biased by the spring 172 such that the locking tooth 166 engages the teeth 76 of the track 58 of the third rail 20. Since the lock 20 is movable by depressing the first end relative to the housing 244 to thereby release the locking tooth 166 from the teeth 76 of the track 58, the fourth slider then can be moved relative to the third rail in any direction along the X-axis. In the variation shown, the fourth slider 24 is configured to move outwardly toward the distal end 178 of the third rail 20 while the locking tooth 166 is engaged by nature of the ramped locking tooth surface engaging the angled flanks of the track 58. This configuration permits the fourth slider 24 to move outwardly toward the distal end 178 while the lock is engaged but the lock 96 is configured to prevent movement of the fourth slider 24 inwardly toward the second slider 16. This configuration allows the fourth slider 24 to move outwardly to expand the tissue opening or wound area preventing the collapse of the tissue opening allowing users to take surgical action in the retracted zone. To close or move the fourth slider 24 to close or reduce the retraction or tissue opening, the user would depress the lock 96 to release the locking tooth 166 from engagement with the track 58 of the third rail 20. With the lock 96 depressed to disengage the locking tooth 166, the third rail 20 does not contact the fourth slider 24. Instead, the third rail 20 contacts one or more antifriction bearings 94 disposed inside the housing 244.

Turning now to FIG. 29, there is shown a retractor blade 266 according to the present invention. The retractor blade 266 is configured to removably attach to the blade mount 92 of each slider. The blades 266 are interchangeable with other blades 266 of different lengths and/or widths. Each blade 266 is an elongated piece of metal or plastic having a length and a width and a generally concave inner surface 268 and a convex outer surface 270. The concave inner surface 268 is configured to face the open retractor zone. The blade 266 includes a cantilevered flange 272 integrally formed down the middle of the blade 266. The proximal end 274 of the flange 272 is free to flex inwardly and outwardly with respect to the rest of the blade 266 whereas the distal end 276 of the flange 272 is integrally connected to the blade 266. The proximal end 274 of the flange 272 includes a first ledge 278 that extends out from the outer surface 270 of the blade 266. The proximal end 280 of the blade 266 includes a second ledge 282 extending from the outer surface 270 of the blade 266. A gap 284 is defined proximal to the proximal end 274 of the flange 272 and configured to receive a hook 300 of a blade instrument 288. The proximal end 280 of the blade 266 includes two guides 286 that extend from the outer surface 270 and are configured to receive the two outwardly extending flanges 140 on the blade mount 92 of a slider.

The blade 266 is connected to the blade mount 92 by first aligning the two guides 286 with the two flanges 140 of the blade mount 92. The first ledge 272 will contact the top of the sidewall 139 of the blade mount aperture 138. Further distal movement of the blade 266 will result in the first ledge 278 deflecting inwardly towards the inner surface 268 of the blade 266. The lower surface of the first ledge 278 is ramped to permit ease of deflection of the first ledge 278. After the sidewall of the blade mount aperture passes the first ledge 278, the first ledge 278 will snap back to its normal undeflected state and into residence underneath the sidewall 139 which will be also captured underneath the second ledge 282 retaining the blade 266 to the blade mount 92. The first ledge 282 is capable of deflection to capture and release the blade 266.

Figure 30A:
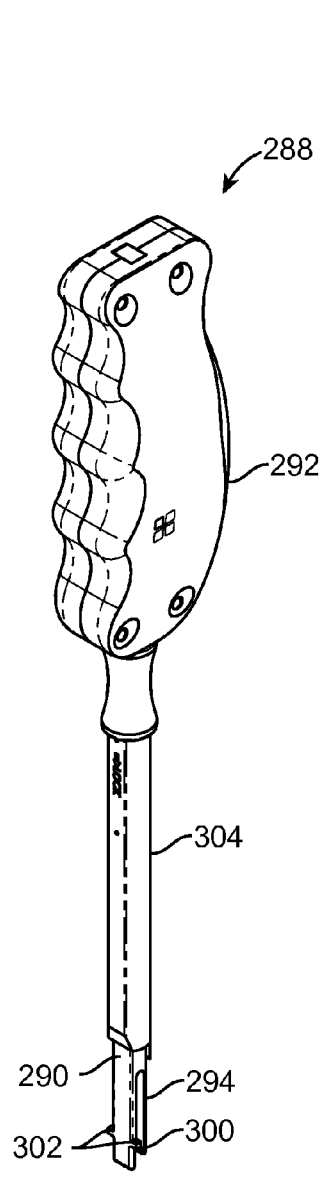
FIG. 30A is a top perspective view of the blade instrument according to the present invention.
Figure 30B:
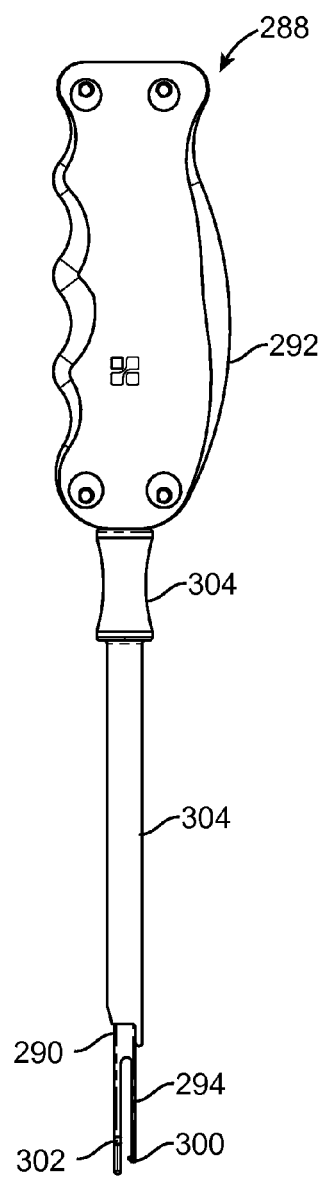
FIG. 30B is a side elevational view of the blade instrument according to the present invention.
Figure 30C:
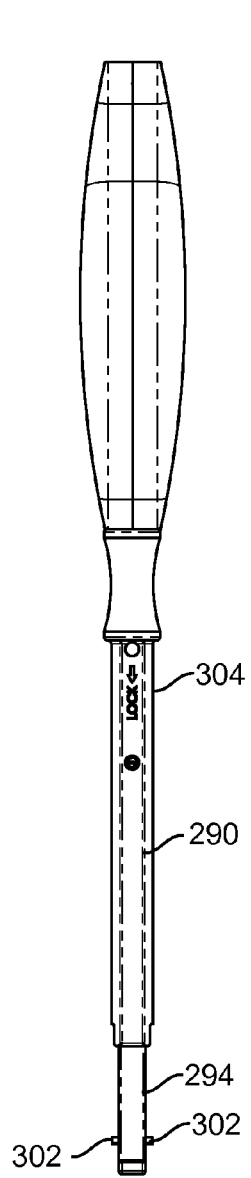
FIG. 30C is an end elevational view of the blade instrument according to the present invention.

Turning now to FIGS. 30a-30b, there is shown a blade instrument 288. The blade instrument 288 is configured for inserting and removing a blade 266. The blade instrument 288 includes an inner elongated rod 290 having handle 292 attached to the proximal end and a pronged distal end 294. The pronged distal end 294 includes a first prong 296 adjacent to and spaced apart from a second prong 298. The first prong 296 includes a hook 300 at the distal end and the second prong 298 includes two outwardly protruding knobs 302. The blade instrument 288 further includes an outer shaft 304 having a lumen that is sized and configured to receive the elongated rod 290 inside the lumen of the shaft 304. The shaft 304 is connected such that it is movable along the longitudinal axis relative to the elongated rod 290.

Figure 32:
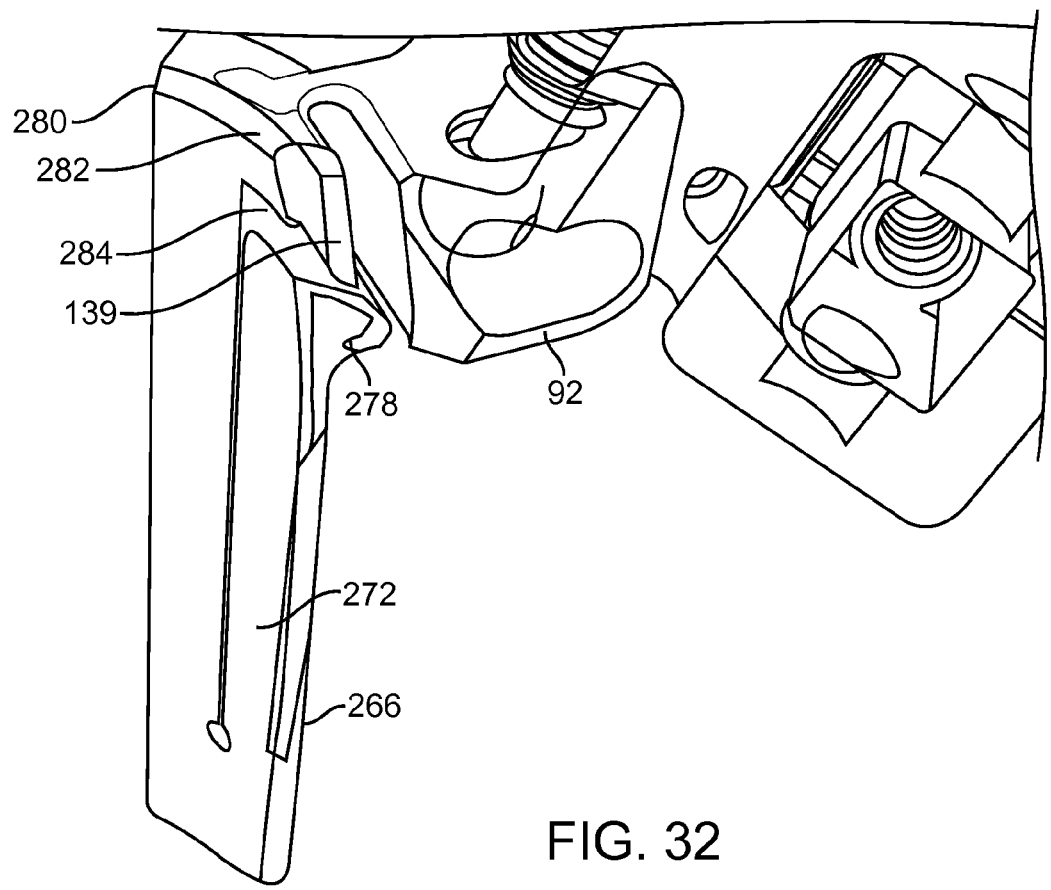
FIG. 32 is a partial sectional view of a blade connected to the blade mount according to the present invention.

Turning now to FIGS. 31a-31b, the blade 266 is connected to the blade instrument 288 by capturing the hook 300 of the first prong 296 into the gap 284 of the blade 266. Both prongs 296, 298 are flexible and the second prong 298 is oriented towards the outer surface 270 of the blade 266 and the first prong 296 is oriented towards the inner surface 268 of the blade 266 with the hook 300 of the first prong 296 disposed inside the gap 284 to retain the blade 266 connected to the blade instrument 288. The outer shaft 304 is moved distally over the pronged distal end 294 to cover at least in part the pronged distal end 294 and prevent the prongs 296, 298 from splaying apart and disconnecting from the blade 266. When connected to the blade instrument 288, the blade 266 can be carried with or without the outer shaft 304 covering the pronged distal end 294. The pronged distal end 294 is uncovered by moving the outer shaft 304 proximally as shown in FIG. 31a such that the blade 266 is free to be released from the blade instrument 288 and connected to the blade mount 92 of the retractor 10. The second prong 298 is positioned inside the aperture 138 of the blade mount 92 and together with the blade 266, moved distally to snap the first ledge 278 underneath the blade mount 92 beneath the sidewall 139 and position the second ledge 282 above the blade mount sidewall 139 as shown in FIG. 32.

To remove the blade 266 from the retractor 10, the blade instrument 288 is positioned by inserting the second prong 298 into the blade receiving aperture of the blade mount until the knobs 302 contact the proximal end 280 of the blade 266. Insertion of the blade instrument 288 will result in the first ledge 278 being deflected toward the inner surface 268 of the blade 266 and out from underneath the blade mount sidewall 139 freeing it for removal in the proximal direction. The first prong 296 is positioned such that the hook 300 is inside the gap 284 of the blade 266. To assist the deflection of the first ledge 278, the outer shaft 304 is movable from a first position in which the prongs 296, 298 are not inside the lumen of the outer shaft 304 to a second position in which the outer shaft 304 covers at least a portion of the prongs 296, 298 such that the prongs are not outwardly deflectable and maintained in a closed positioned for capturing and removal of the blade 266 as shown in FIG. 31b.

The use of the retractor 10 will now be discussed. The entry point for the retractor 10 into the patient is determined with anterior, posterior and lateral fluoroscopy. An incision is made in the patient that is slightly larger than the width dimension of the closed retractor base. The closed retractor base dimension is approximately 2.0 to 5.0 centimeters in one variation and in another variation approximately 2.6 centimeters, which is the distance between the distal ends of the blades in the closed non-angled orientation. A first dilator is inserted into the incision and advanced through the fascia and muscle tissue. Placement of a dilator is confirmed with fluoroscopy and by palpating the bony anatomy. Additional dilators are placed sequentially by passing the next largest dilator over the previously inserted dilator. If resistance is met, a scalpel is used to further incise the skin and fascia. Retractor blade length is selected by measuring the tissue depth from the etch markings provided on the last dilator. The tissue depth read from the etch markings directly corresponds to the suggested retractor blade length for use with the retractor 10. The selected blades are inserted onto the blade mounts. When a blade 166 is fully seated within a blade mount there is an audible and tactile "click". Various retractor blades 266 of different lengths are interchangeable with the retraction and range from approximately 30 mm to 120 mm in length. Each length being coded to a different retractor blade color for ease of selection and installation into the retractor 10. With the blades 266 attached to the retractor 10, the retractor 10 is inserted into a patient wound for distracting tissue of the surgical site.

Figure 33:
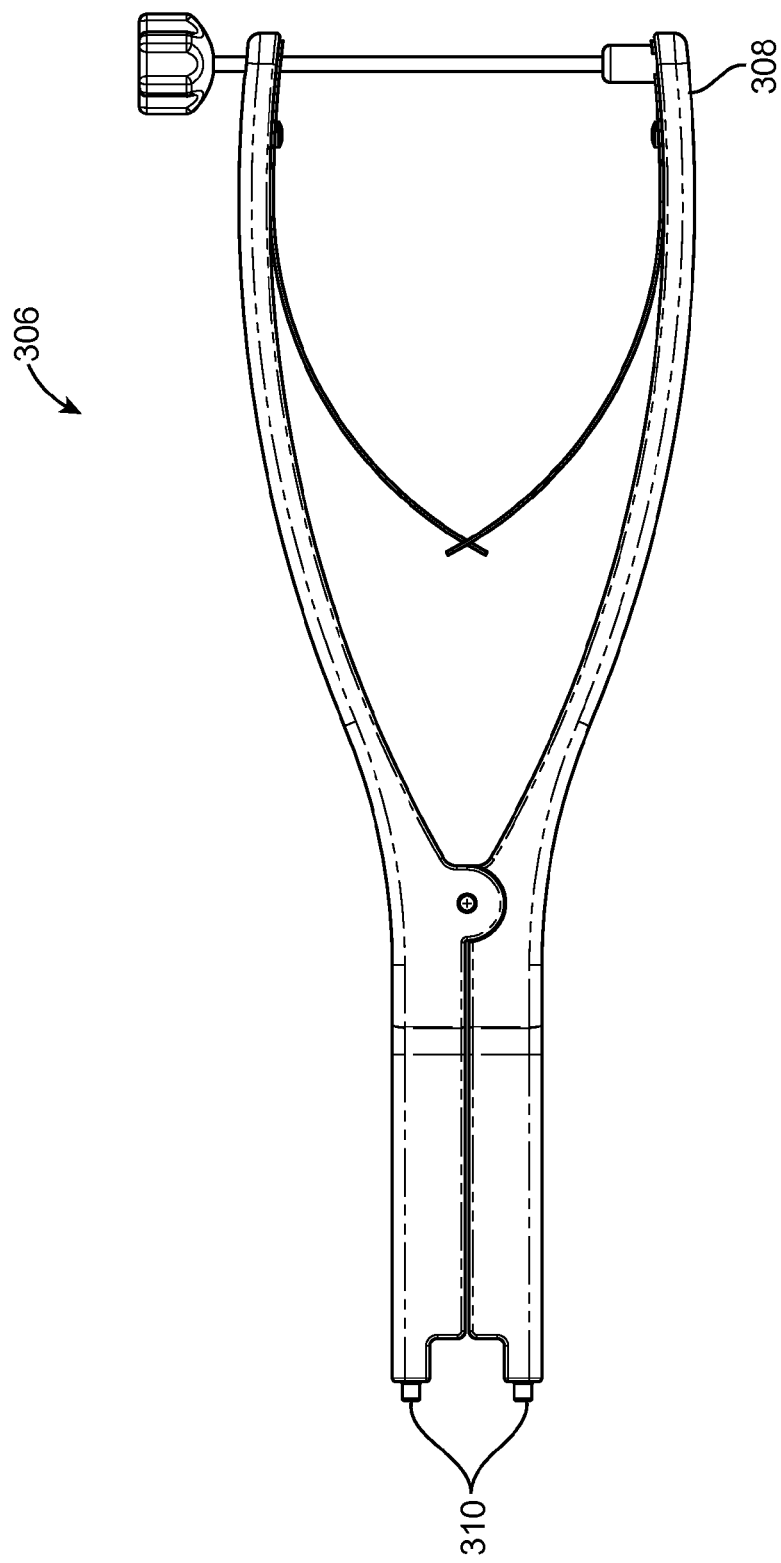
FIG. 33 is a side view of a slider instrument according to the present invention.

Turning now to FIG. 33, a slider instrument 306 according to the present invention will now be described. The slider instrument 306 is used for distracting the retractor 10 to increase the retractor zone for obtaining surgical access to the target tissue site. The slider instrument 306 includes a handle 308 at the proximal end and a pair of movable prongs 310 at the distal end. The prongs 310 are sized and configured for insertion into distraction apertures 312 formed in the top surface each of the sliders 14, 16, 22, 24.

Figure 34A:
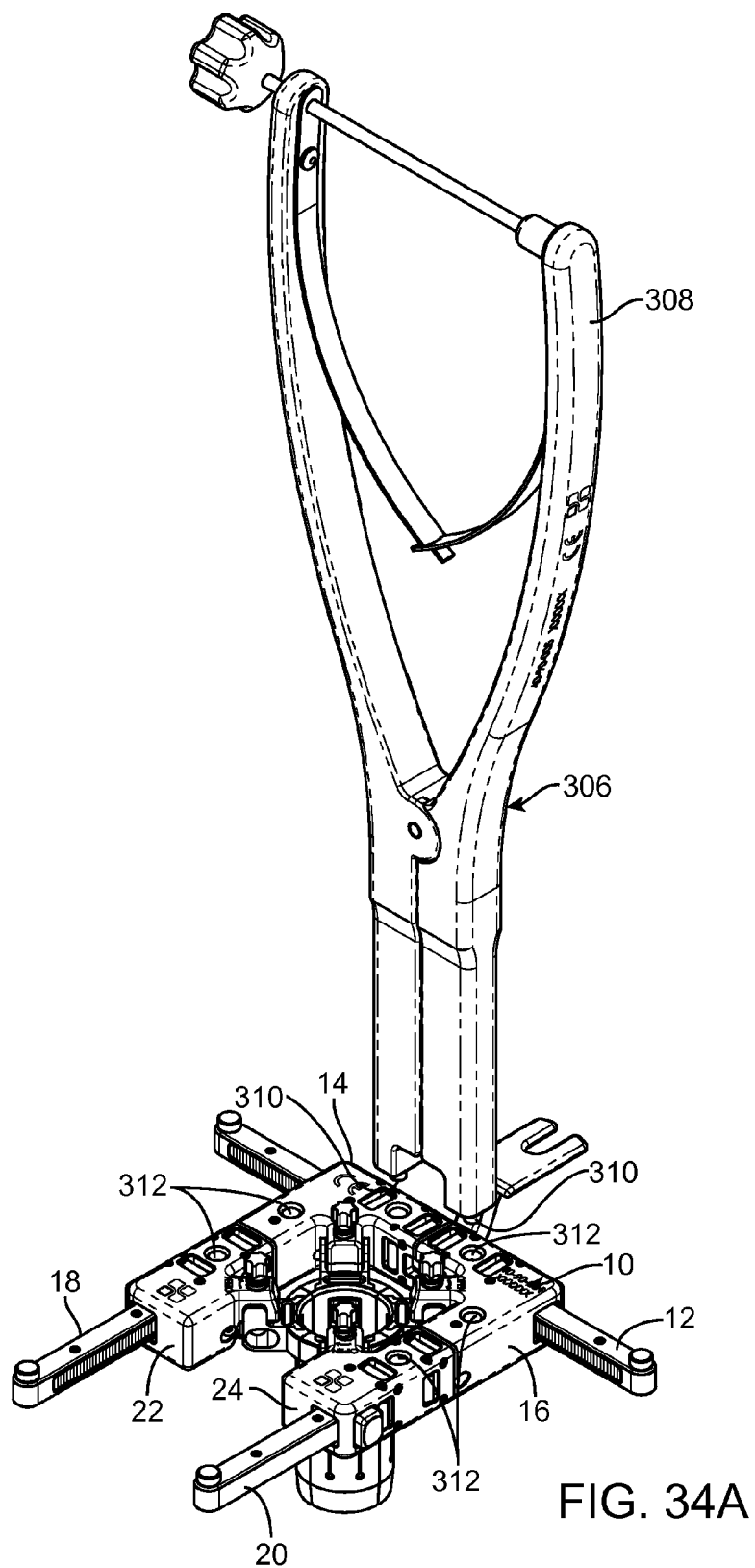
FIG. 34A is a top perspective view of the distraction instrument and retractor according to the present invention.
Figure 34B:
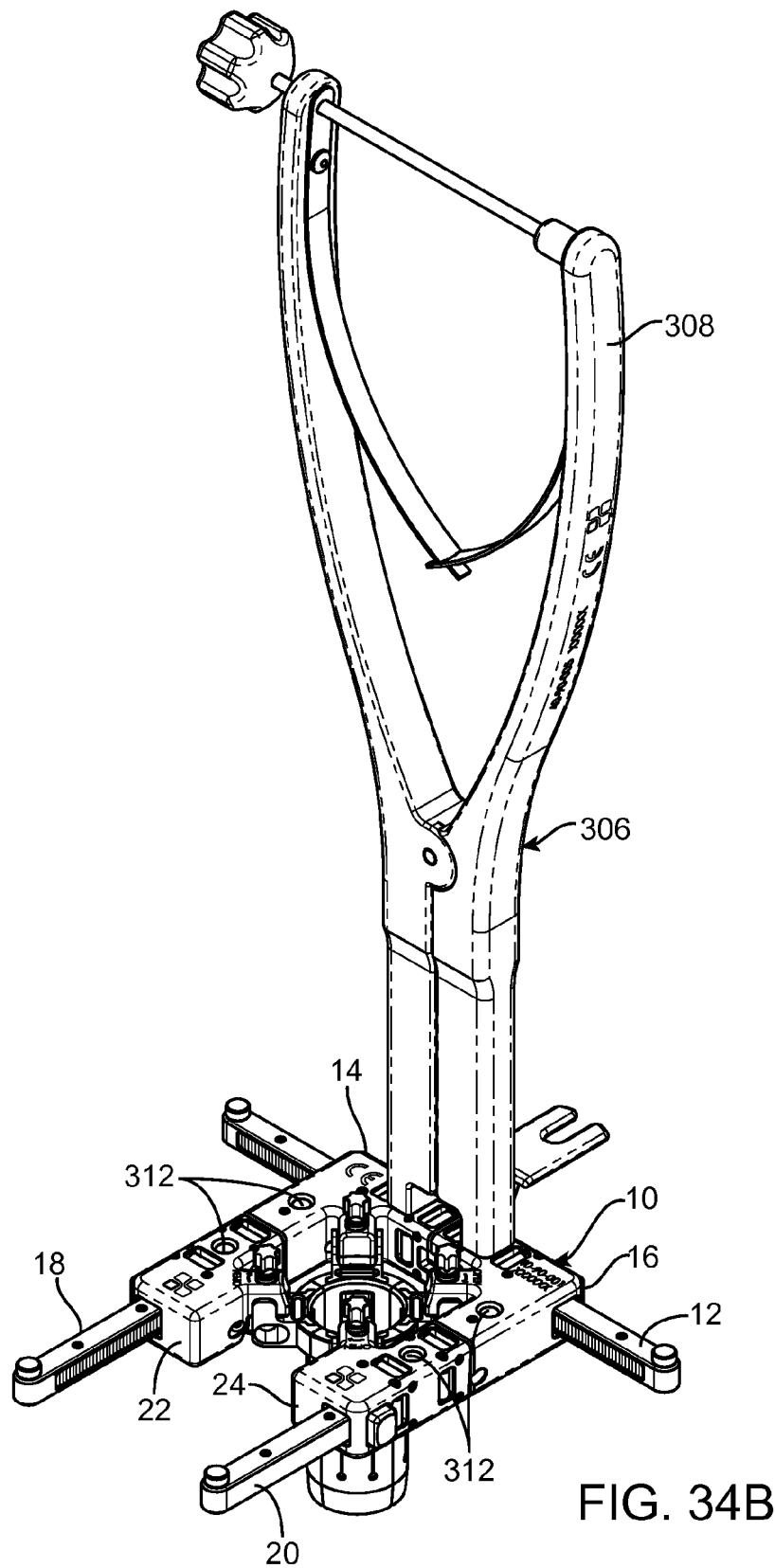
FIG. 34B is a top perspective view of the distraction instrument and retractor according to the present invention.
Figure 35A:
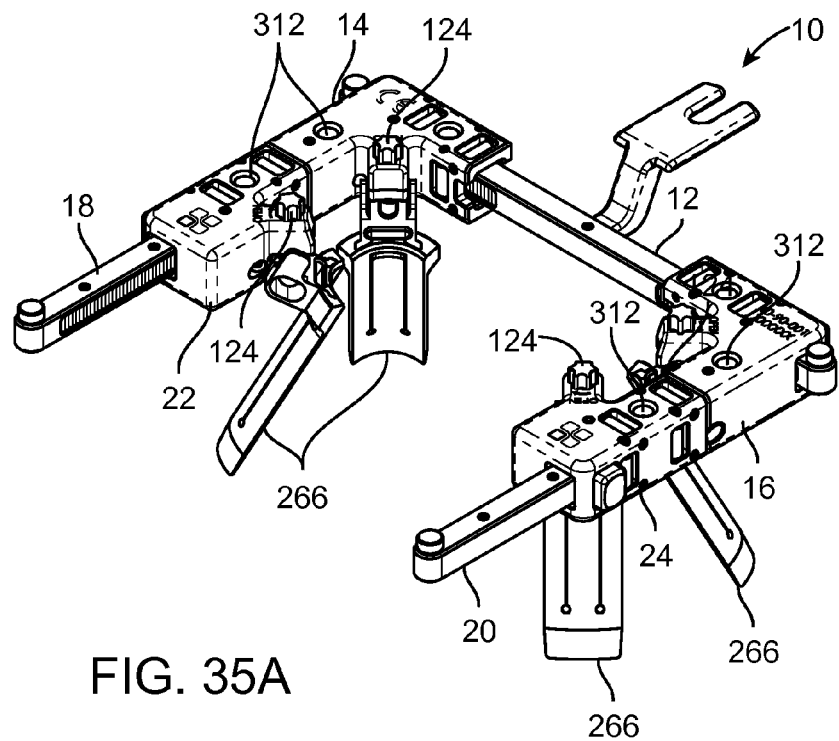
FIG. 35A is a top perspective view of the retractor with the first and second sliders distracted according to the present invention.
Figure 35B:
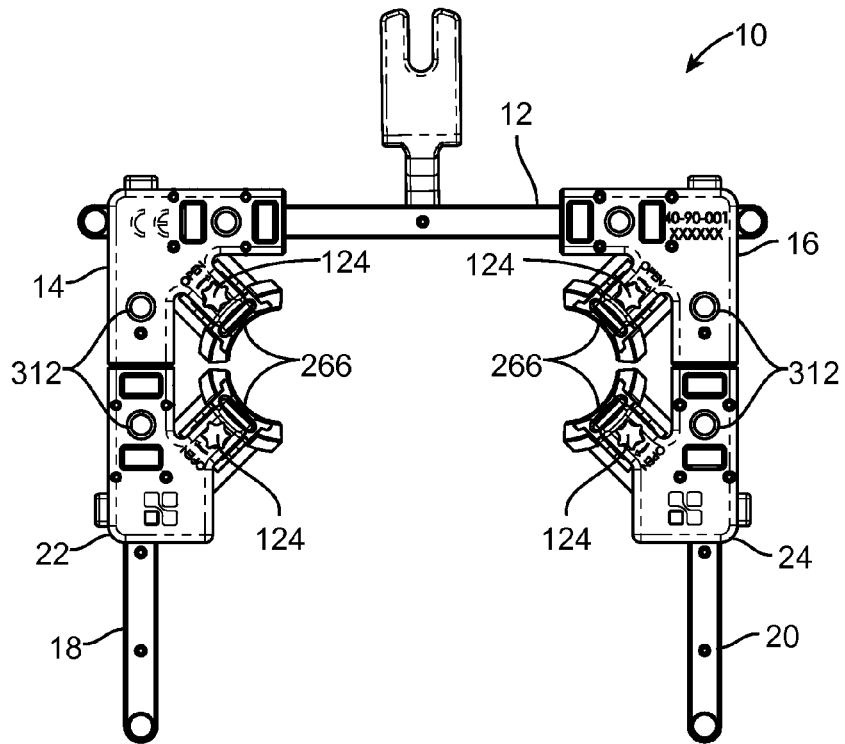
FIG. 35B is a top view of the retractor with the first and second sliders distracted according to the present invention.
Figure 35C:
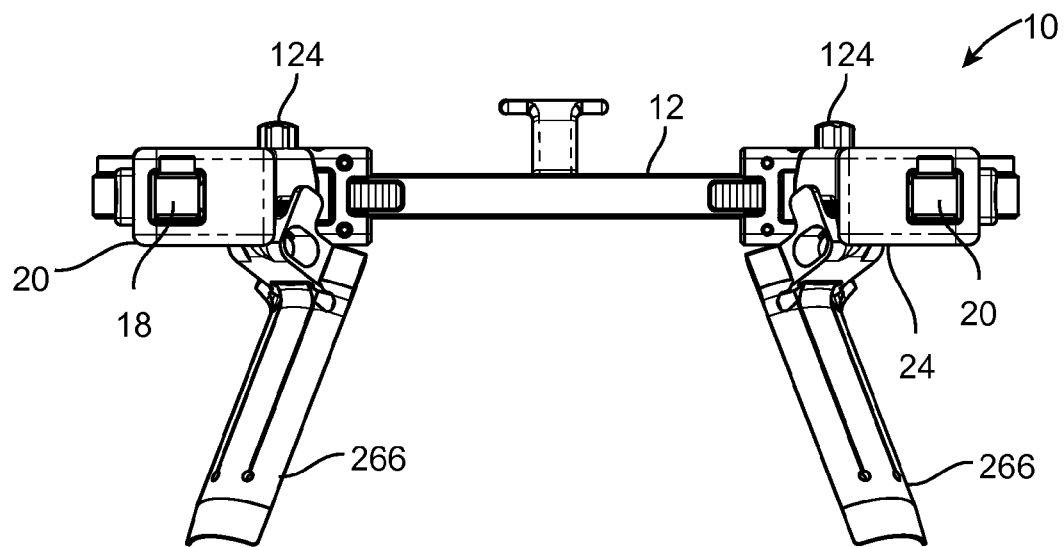
FIG. 35C is an end elevational view of the retractor with the first and second sliders distracted according to the present invention.
Figure 35D:
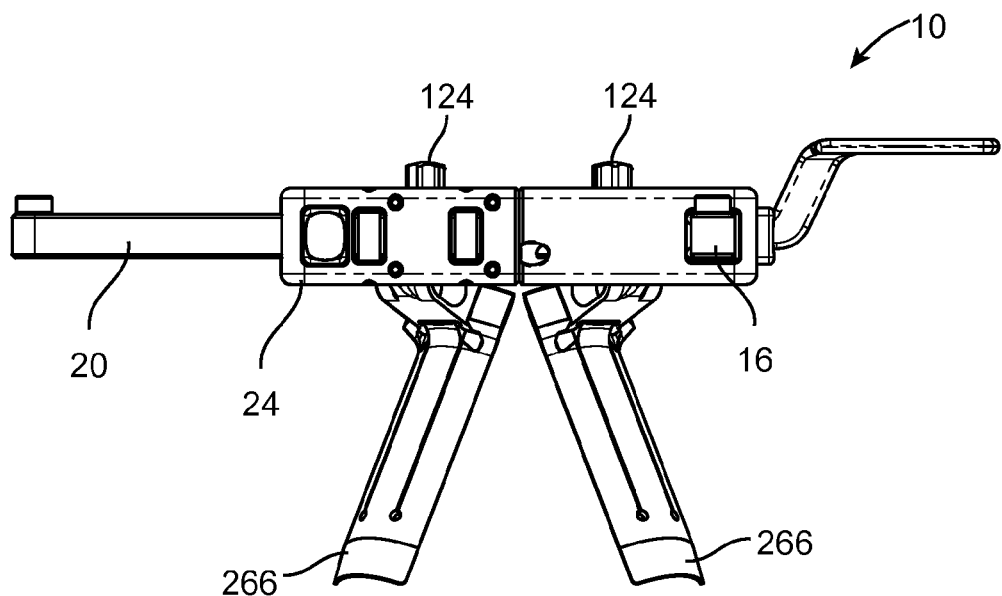
FIG. 35D is a side elevational view of the retractor with the first and second sliders distracted according to the present invention.
Figure 36A:
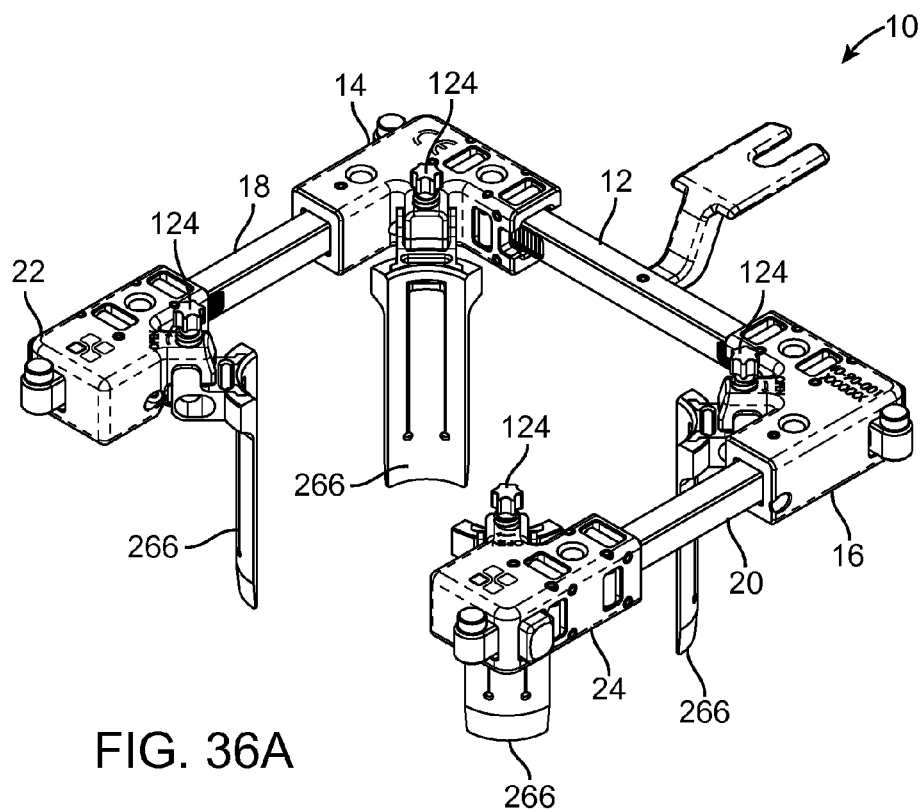
FIG. 36A is a top perspective view of the retractor with the first, second, third and fourth sliders distracted with respect to each other according to the present invention.
Figure 36B:
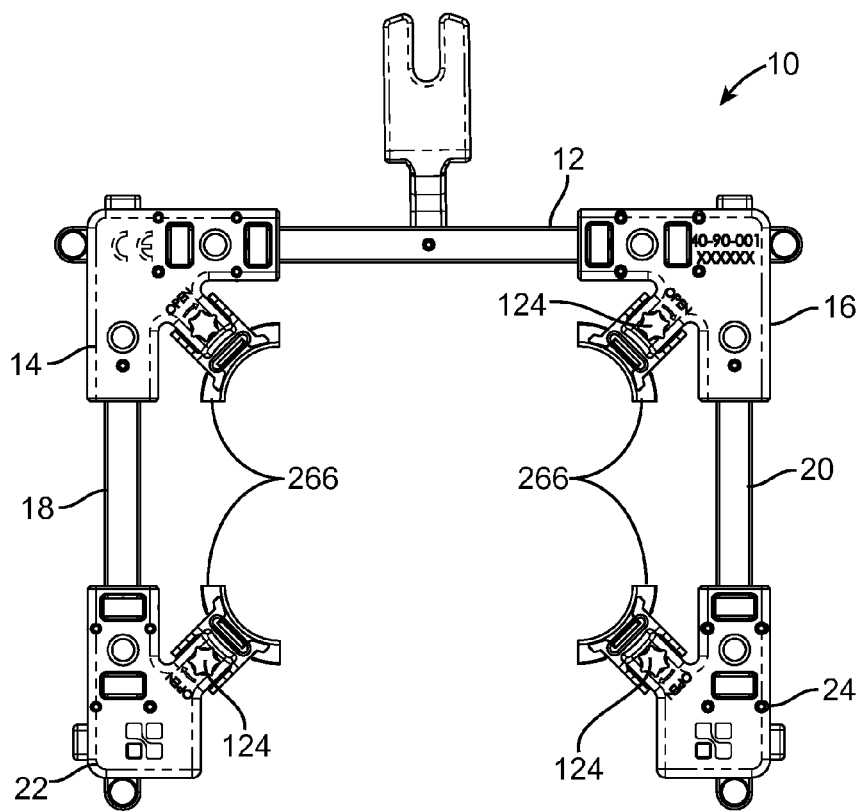
FIG. 36B is a top view of the retractor with the first, second, third and fourth sliders distracted with respect to each other according to the present invention.
Figure 36C:
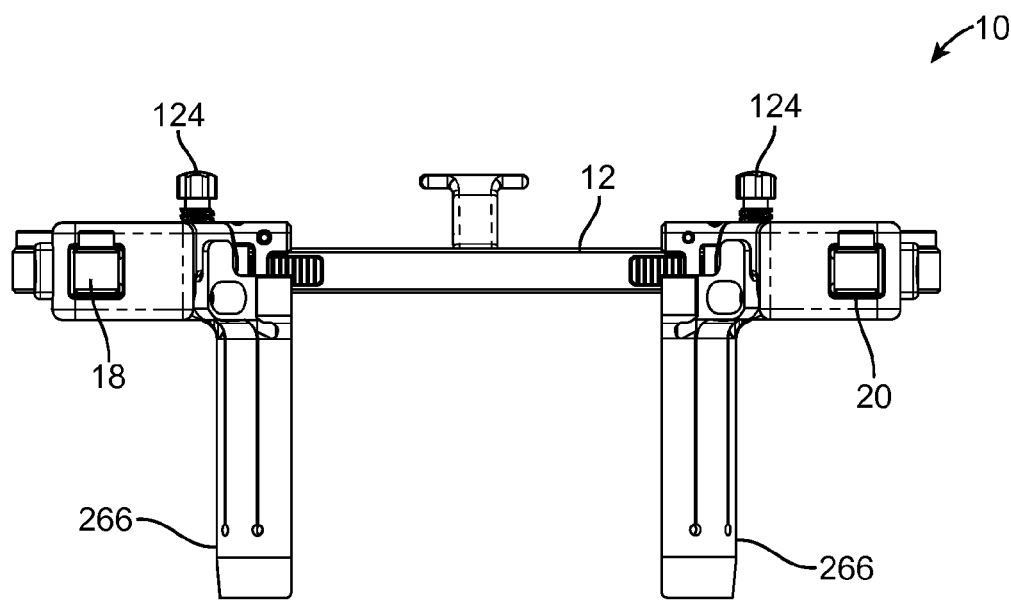
FIG. 36C is an end elevational view of the retractor with the first, second, third and fourth sliders distracted with respect to each other according to the present invention.
Figure 36D:
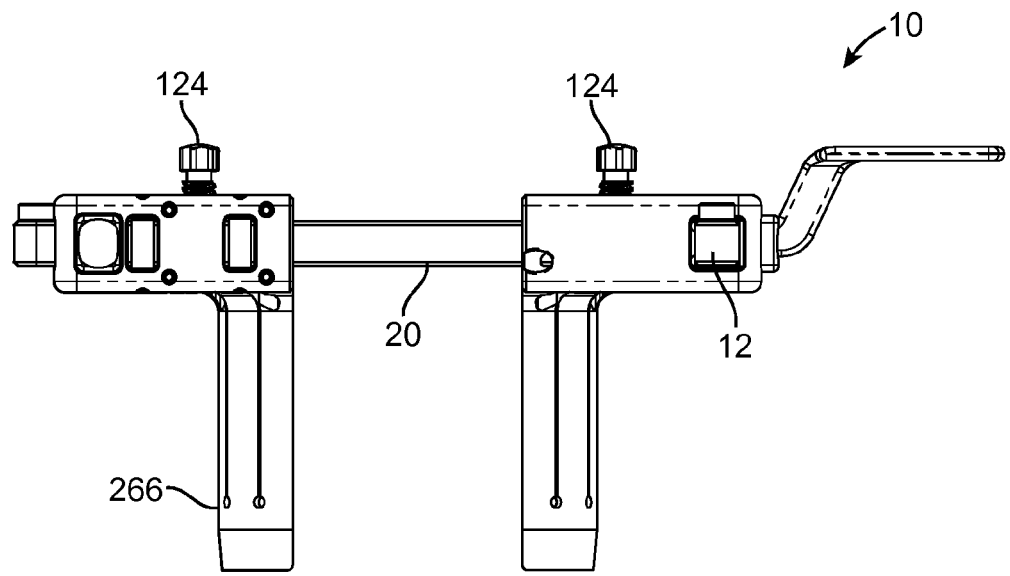
FIG. 36D is a side elevational view of the retractor with the first, second, third and fourth sliders distracted with respect to each other according to the present invention.
Figure 37A:
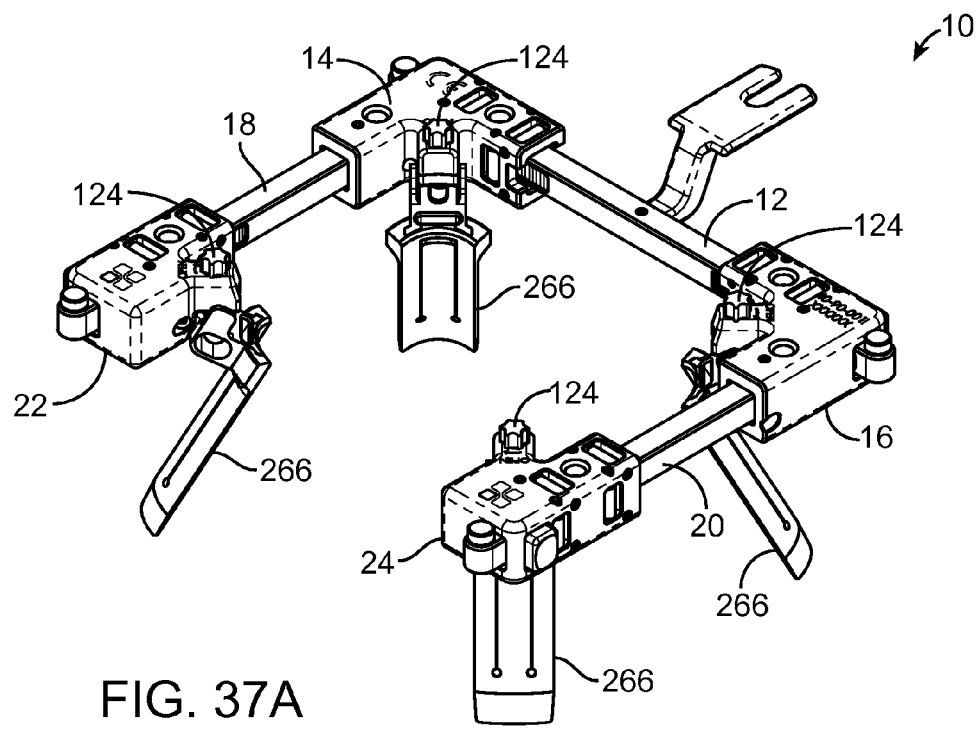
FIG. 37A is a top perspective view of the retractor with the first, second, third and fourth sliders distracted and the blades angled outwardly according to the present invention.
Figure 37B:
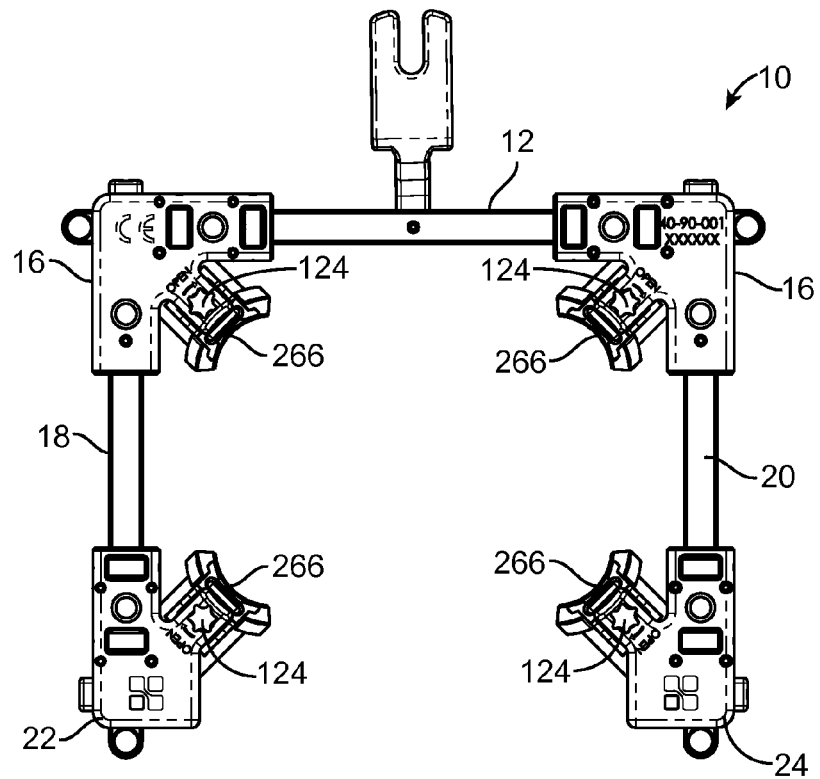
FIG. 37B is a top view of the retractor with the first, second, third and fourth sliders distracted and the blades angled outwardly according to the present invention.
Figure 37C:
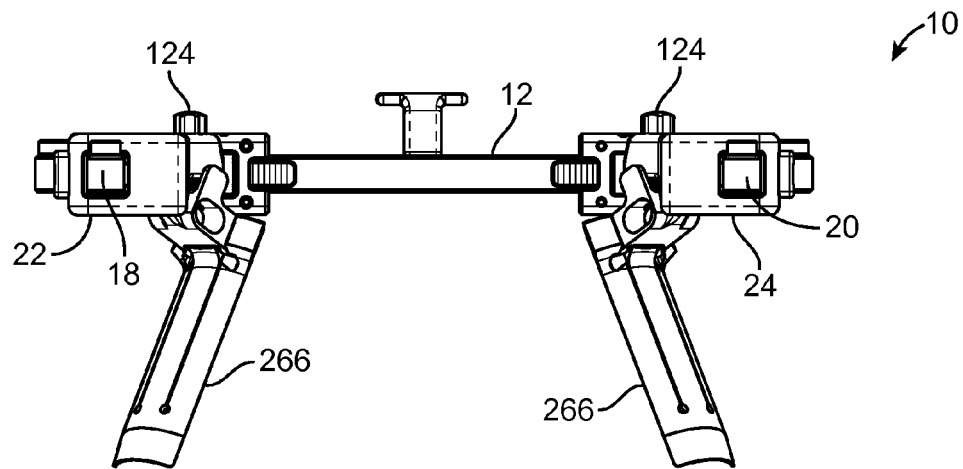
FIG. 37C is an end elevational view of the retractor with the first, second, third and fourth sliders distracted and the blades angled outwardly according to the present invention.
Figure 37D:
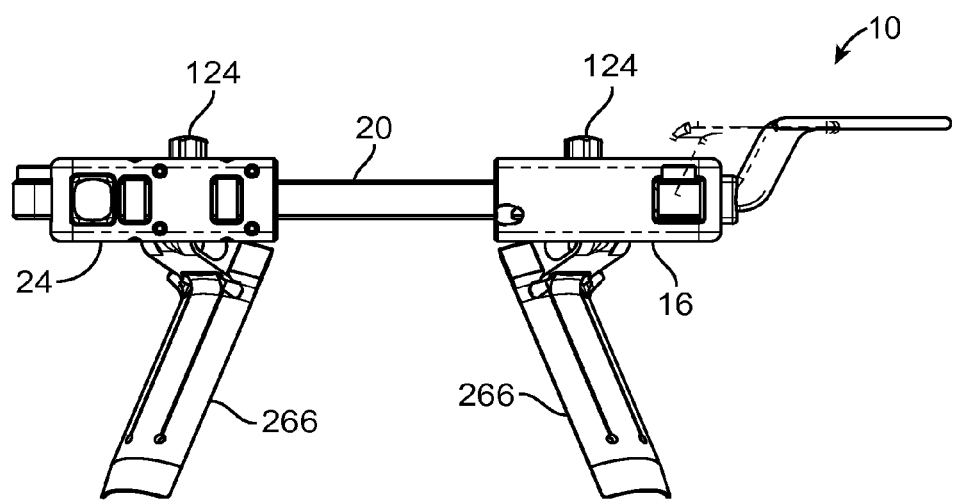
FIG. 37D is a side elevational view of the retractor with the first, second, third and fourth sliders distracted and the blades angled outwardly according to the present invention.
Figure 38A:
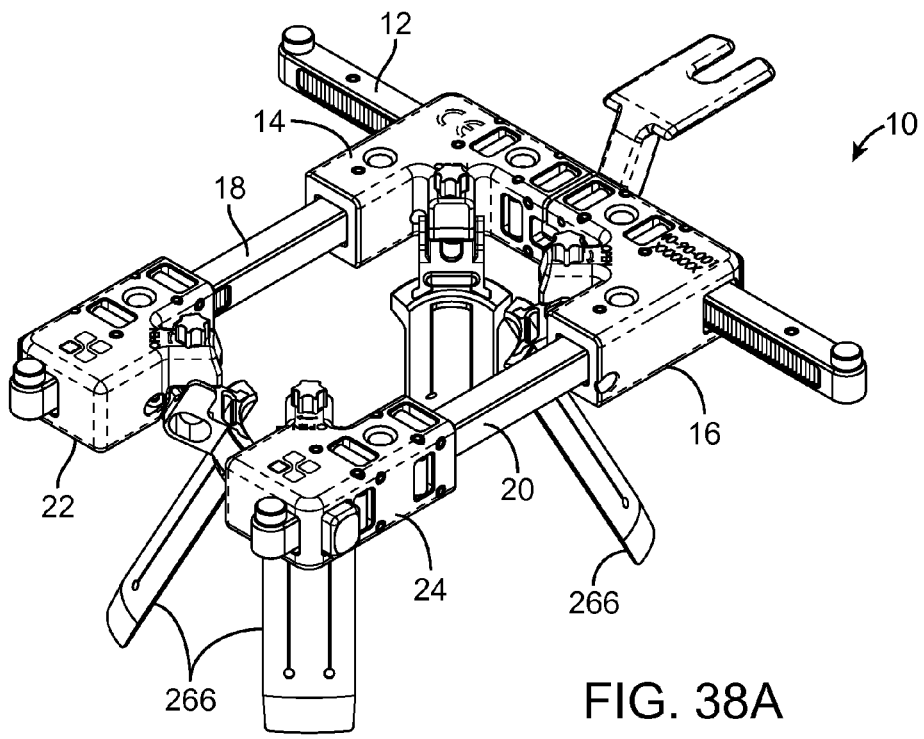
FIG. 38A is a top perspective view of the retractor with the third slider distracted relative to the first slider and the fourth slider distracted relative to the second slider and the blades angled according to the present invention.
Figure 38B:
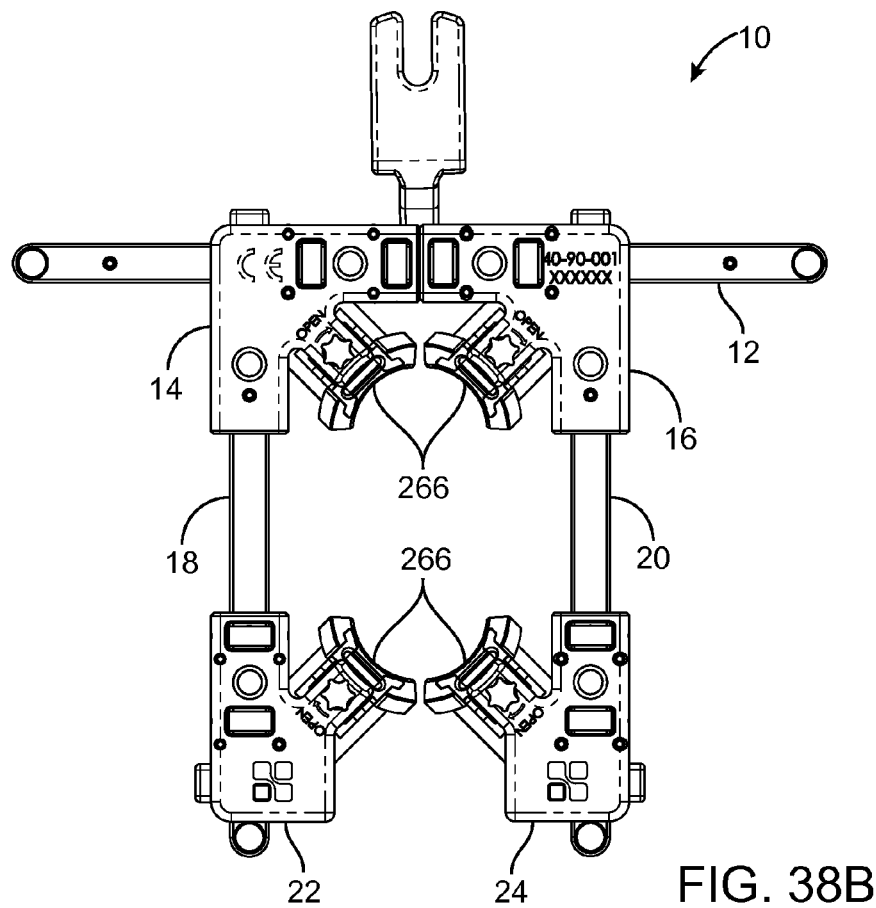
FIG. 38B is a top view of the retractor with the third slider distracted relative to the first slider and the fourth slider distracted relative to the second slider and the blades angled according to the present invention.
Figure 38C:
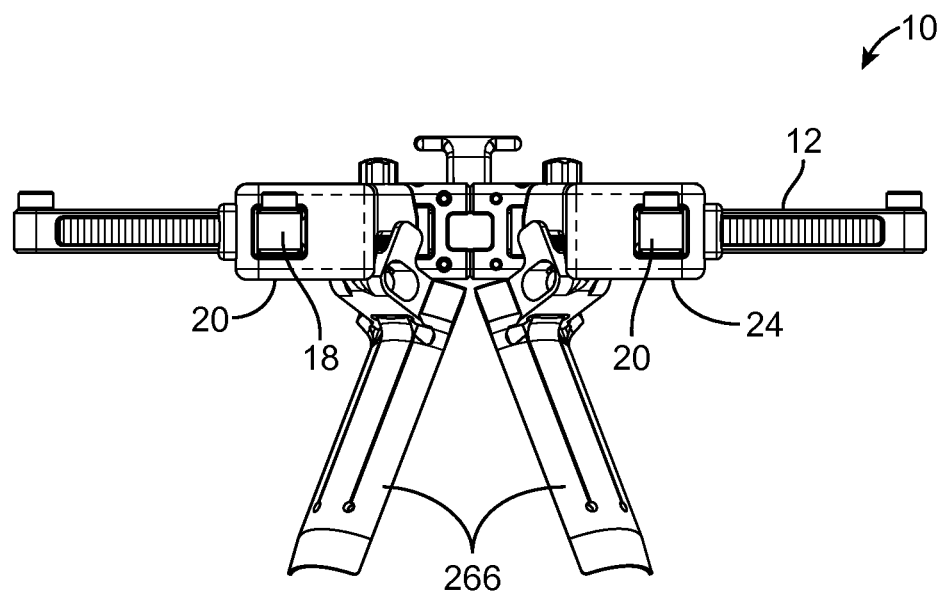
FIG. 38C is an end elevational view of the retractor with the third slider distracted relative to the first slider and the fourth slider distracted relative to the second slider and the blades angled according to the present invention.
Figure 38D:
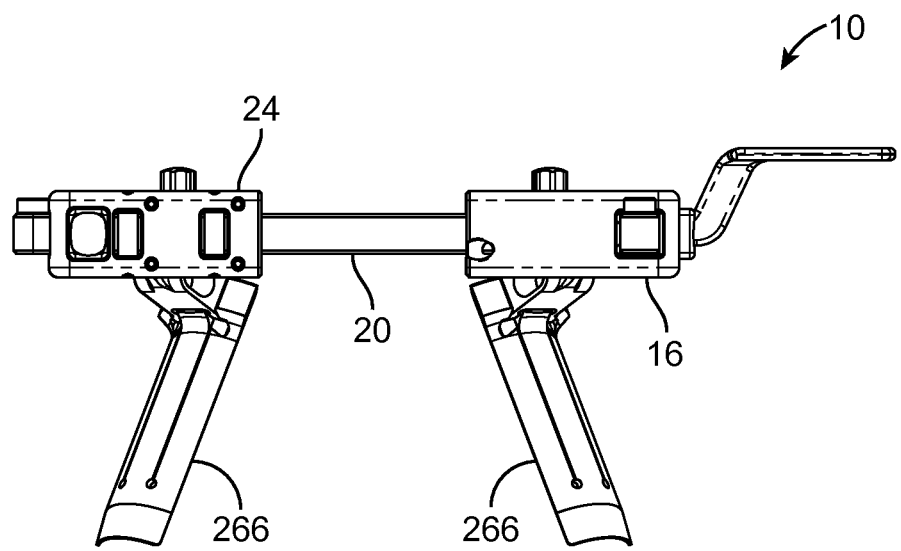
FIG. 38D is a side elevational view of the retractor with the third slider distracted relative to the first slider and the fourth slider distracted relative to the second slider and the blades angled according to the present invention.

FIG. 34a illustrates the slider instrument 306 positioned above a retractor 10 such that prongs 310 are above and aligned with distraction apertures 312 in the first and second sliders 14, 16 with the handle 308 in a first position. The prongs 310 are inserted into the distraction apertures 312 as shown in FIG. 34b and the handle 308 squeezed to spread apart the prongs 310 and sliders 14, 16 from the orientation shown in FIG. 34 to the orientation shown in FIG. 35 for a medial-lateral distraction. The medial-lateral translation distance is approximately 1.0 mm and up to a maximum span in the range of between approximately 2.0 centimeters and approximately 10.0 centimeters in one variation. The slider instrument 306 is removed and positionable inside distraction apertures 312 in the first and third sliders 14, 22 to move them apart from each other and also into the second and fourth sliders 16, 24 to move them apart from each other from the orientation shown in FIG. 35 to the orientation shown in FIG. 36 for a cephalad-caudal expansion of the retractor. Of course, although distraction is referred to in the medial-lateral and cephalad-caudal direction with respect to the patient, the invention is not limited to the orientation of the instrument with respect to the patient anatomy. FIG. 36 illustrates a fully distracted retractor 10 with all of the sliders 14, 16, 22, 24 spread apart from each as much as possible with the blades 266 in substantially vertical orientation. A hex socket instrument (not shown) can be used to turn the tow angle posts of each of the sliders 14, 16, 22, 24, respectively, to angulate the blades 266 outwardly from the orientation shown in FIG. 36 to the orientation shown in FIGS. 37a-37d or to any position therebetween. The blades 266 angle up to a maximum of approximately 30 degrees in one variation. Maximum angulation of the blades 266 with respect to the Z-axis is between approximately 5 and 80 degrees. The size of the opening at the distal end of the blades depends upon blade length. If blades of a first length are employed, the maximum distal span for a 30-millimeter long blade is approximately 11 centimeters as shown. If blades of a second length are employed, the maximum distal span for a 90-millimeter long blade is approximately 17 centimeters for example.

The retractor 10 is shown in FIGS. 38a-38d with the third slider 22 distracted relative to the first slider 14 and the fourth slider 24 distracted relative to the second slider 16 and the blades 266 angled from a vertical orientation relative to the Z-axis. Any combination or degree of slider distraction and degree of angulation makes the retractor 10 suitable for customized distraction of the operative space.

Figure 39:
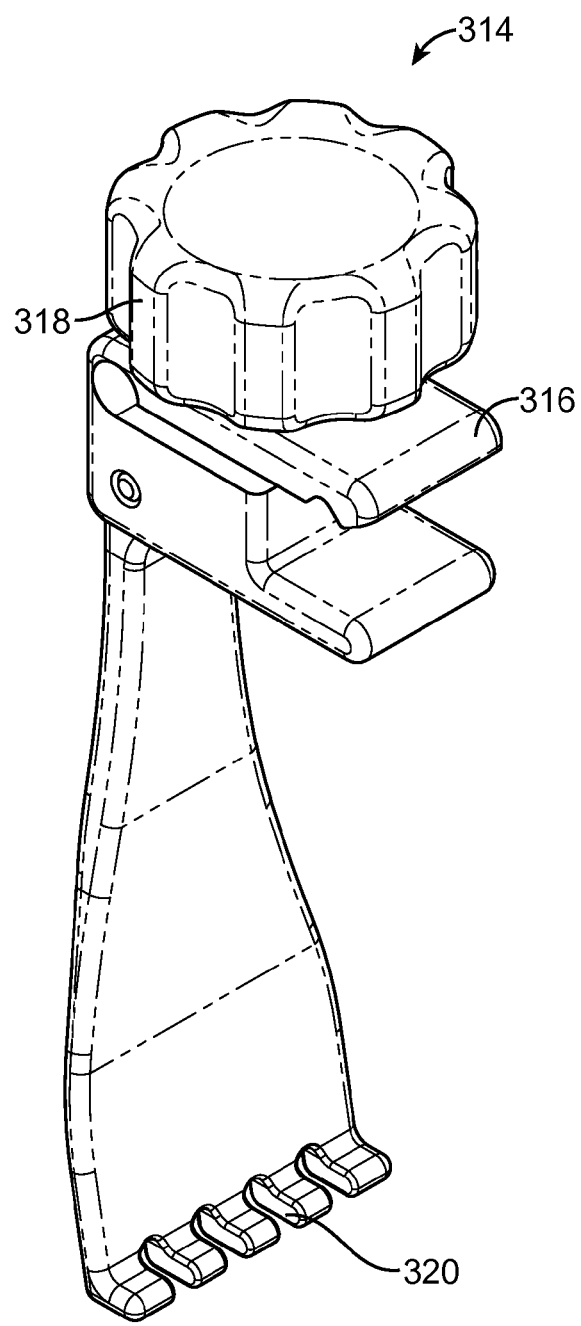
FIG. 39 is a perspective view of a medial blade according to the present invention.
Figure 40:
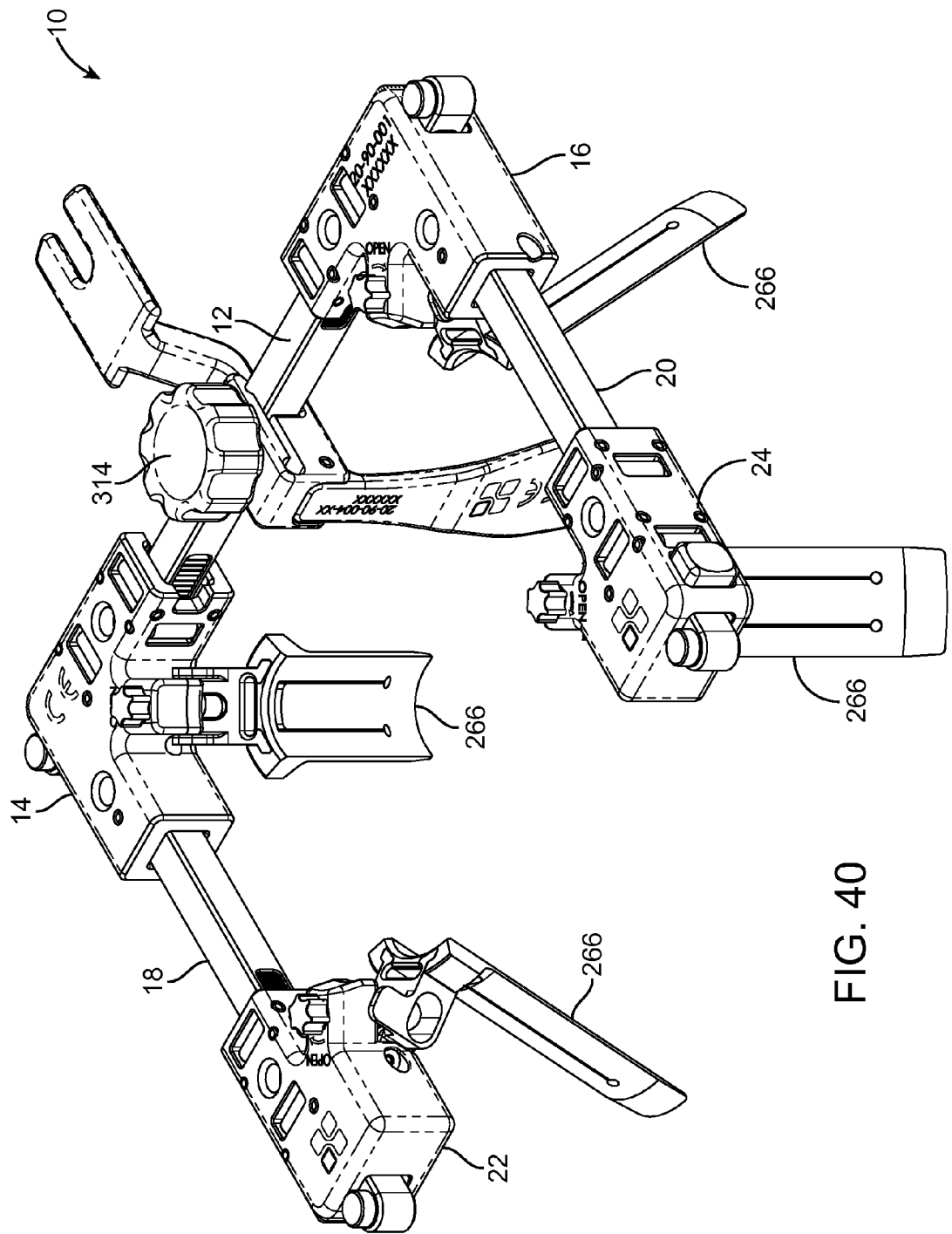
FIG. 40 is a perspective view of a medial blade connected to the retractor according to the present invention.
Figure 41:
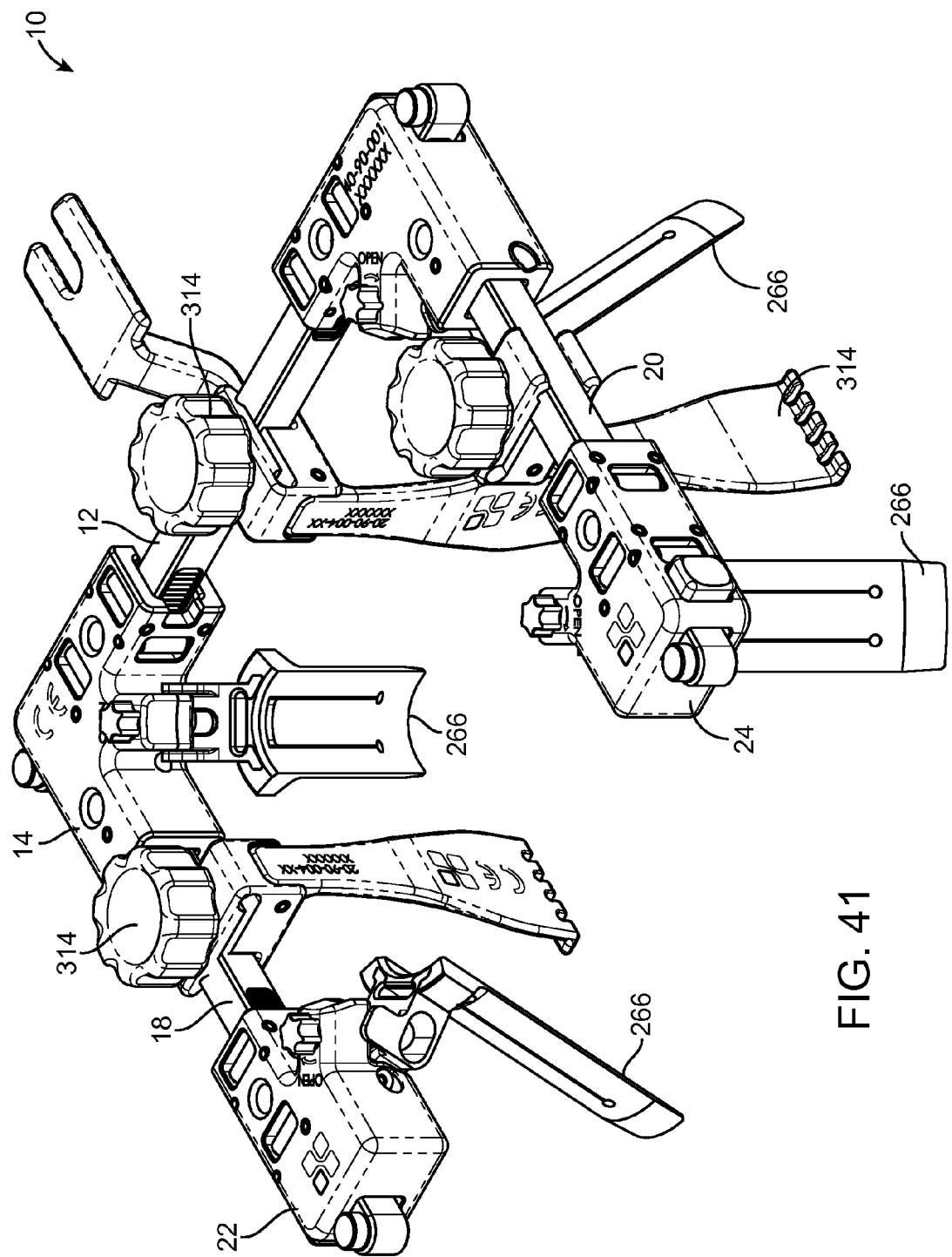
FIG. 41 is a perspective view of three medial blades connected to the retractor according to the present invention.

Turning now to FIG. 39, there is shown a medial blade 314 configured for placement on at least one of the rails 12, 18, 20 between the sliders 14, 16, 22, 24 for additional tissue retraction capability. The medial blade 314 includes a channel 316 for hooking onto one of the rails 12, 18, 20 and movable into a desired position along the rails 12, 18, 20. A locking knob 318 is provided for tightening the channel 316 onto the rail for connecting therewith. The distal end of the medial blade 314 is shown to include teeth 320. FIG. 40 illustrates a single medial blade 314 hooked on the first rail 12. FIG. 41 illustrates a medial blade 314 connected to the first rail in addition to a second and third medial blades 314 connected to the second and third rails 18, 20. The medial blades 314 can be connected to the rails for retaining tissue between the blades 266 from creeping into the retractor zone and may be angled for tissue retraction.

Removal of the retractor 10 will now be described. To remove the retractor 10 from the patient, any of the blades that are angled are reset to zero degrees with respect to the Z-axis by using a hex socket instrument to turn the one or more of the tow angle posts 124. To close the retractor 10 to thereby minimize or reduce the size of the retractor zone, any one of the locks 96 on the any of the sliders 14, 16, 22, 24 are depressed to disengage the locking tooth 166 from the track 58. With the locking tooth 166 disengaged, the sliders will easily slide in any direction along the rail and into a closed orientation relative to the other sliders to close the retractor 10 for its subsequent removal. For example, the lock 96 of the first slider 14 is depressed to move the first slider 14 toward the second slider 16 along rail 12. Similarly, the lock 96 of the third slider 22 is depressed to free it for movement along the second rail 18 and in a direction toward the first slider 14 to reduce the retractor size. Also, the lock 96 of the fourth slider 24 is depressed to slide it toward the second slider 16. The fully closed orientation of the sliders 14, 16, 22, 24 on the retractor 10 resembles the device depicted in FIG. 1. From this orientation, the retractor 10 is easily removed from the surgical site.

Figure 42A:
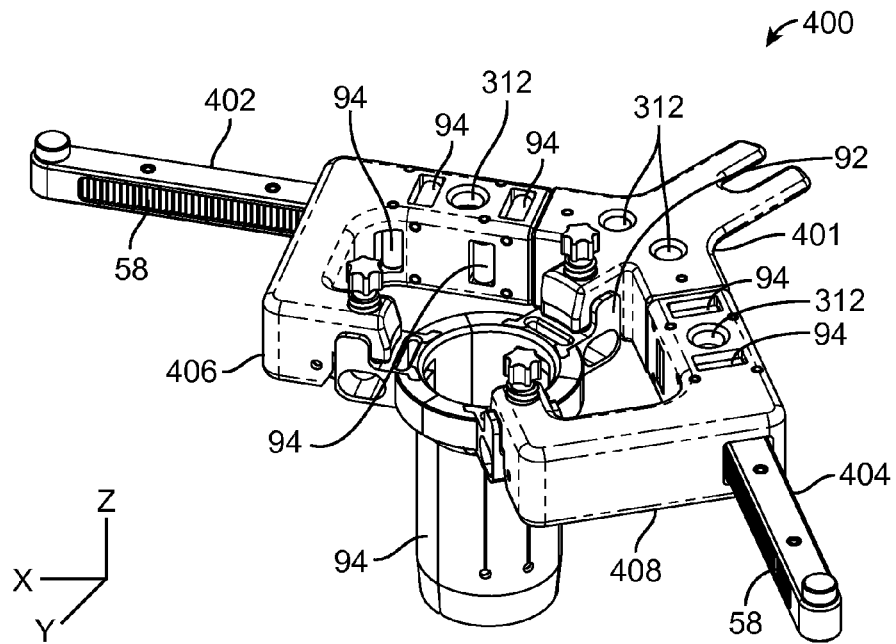
FIG. 42A is a top perspective view of another variation of the retractor according to the present invention.
Figure 42B:
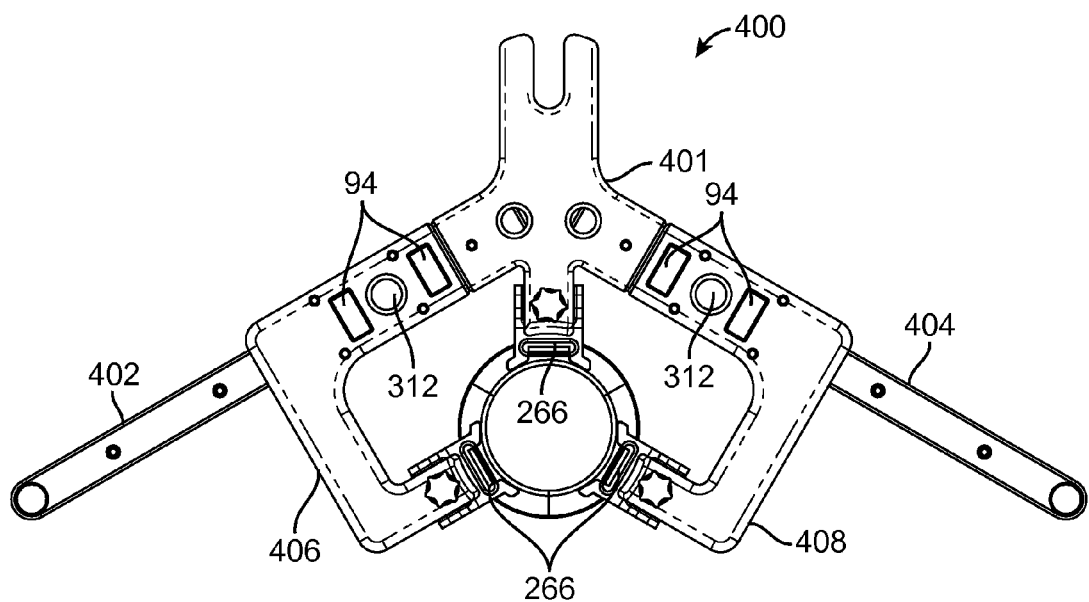
FIG. 42B is a top view of another variation of the retractor according to the present invention.
Figure 42C:
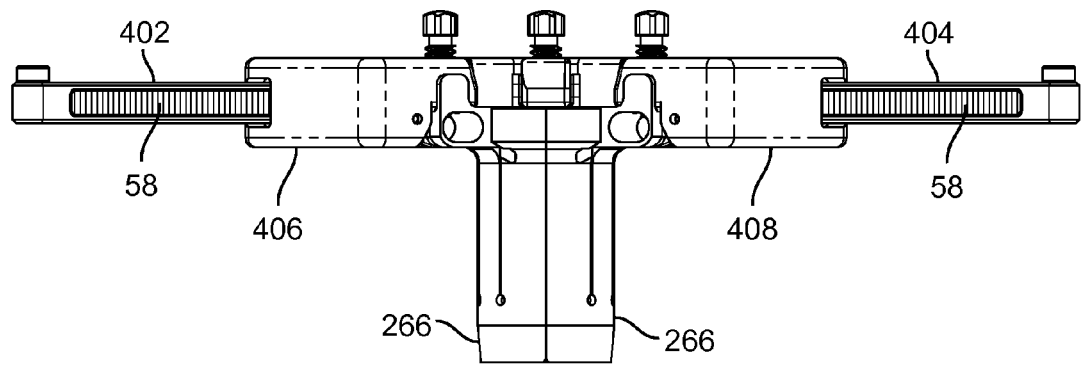
FIG. 42C is an end elevational view of another variation of the retractor according to the present invention.
Figure 42D:
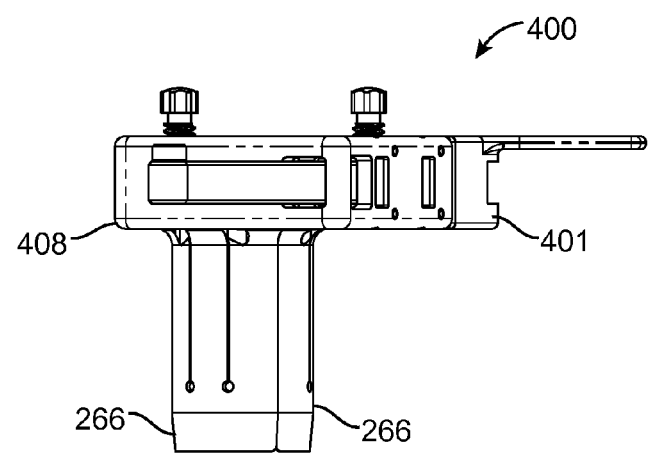
FIG. 42D is a side elevational view of another variation of the retractor according to the present invention.

Turning now to FIGS. 42a-42b, there is shown another variation of a retractor 400 according to the present invention. The retractor 400 includes a rail housing 401 connected to a first rail 402 and second rail 404. A first slider 406 is movably connected to the first rail 402 and a second slider 408 is connected to the second rail 404.

The rail housing 401 includes a first rail receiving portion and a second rail receiving portion. The first and second rail receiving portions are configured to receive and connect the first and second rails 402, 404. In the variation shown, the first and second rail receiving portions are angled such that connected first and second rails 402, 404 are angled with respect to each other and parallel to the X-Y plane. The angle between the first and second rails 402, 404 is shown to be greater than 90 degrees. The rail housing 401 includes a blade mount 92 of the same kind as described above with reference to FIG. 15 and connected in the same pivotable manner and provided with removable and interchangeable blades 266.

Figure 43A:
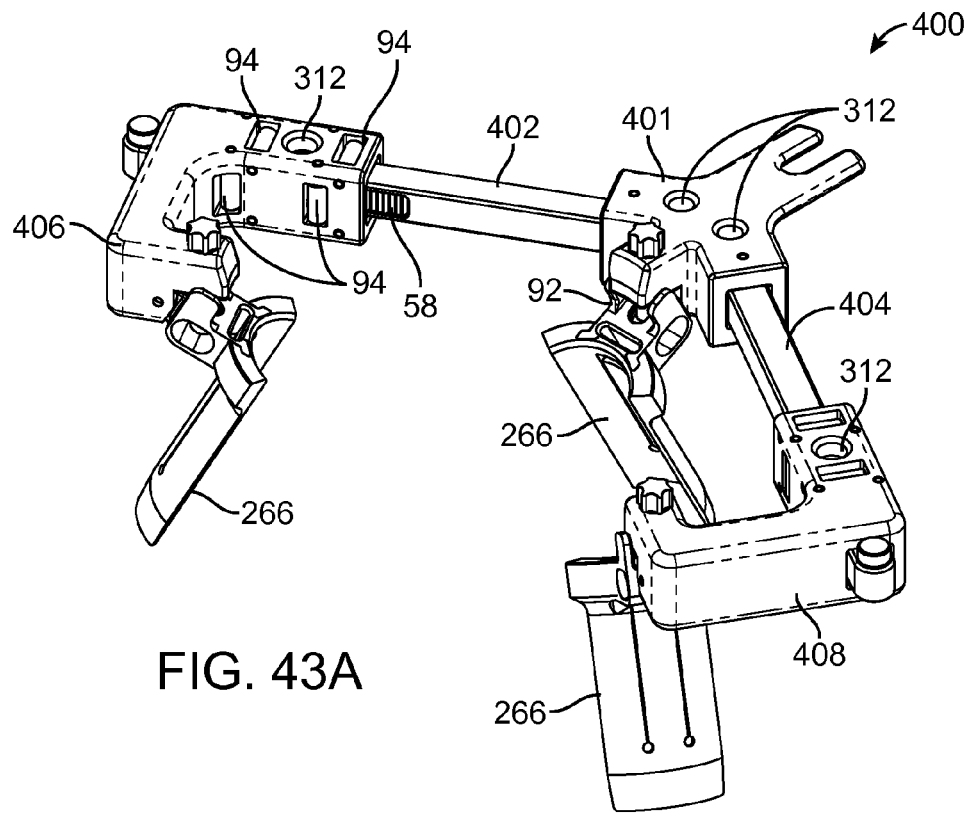
FIG. 43A is a top perspective view of the retractor of FIG. 42 with the sliders extended according to the present invention.
Figure 43B:
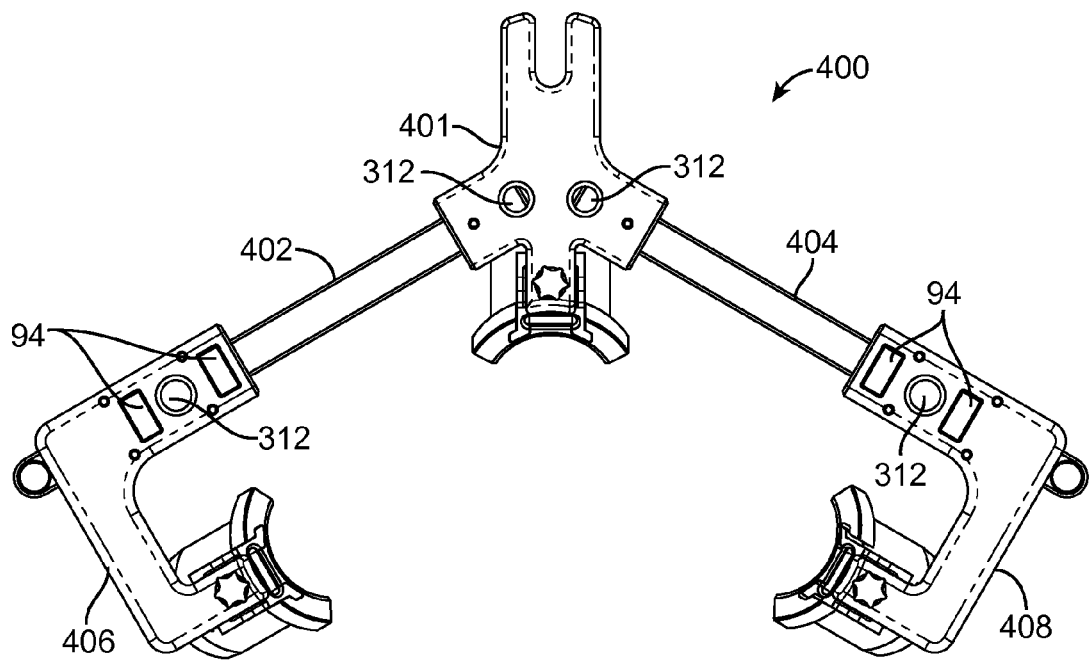
FIG. 43B is a top view of the retractor of FIG. 42 with the sliders extended according to the present invention.
Figure 43C:
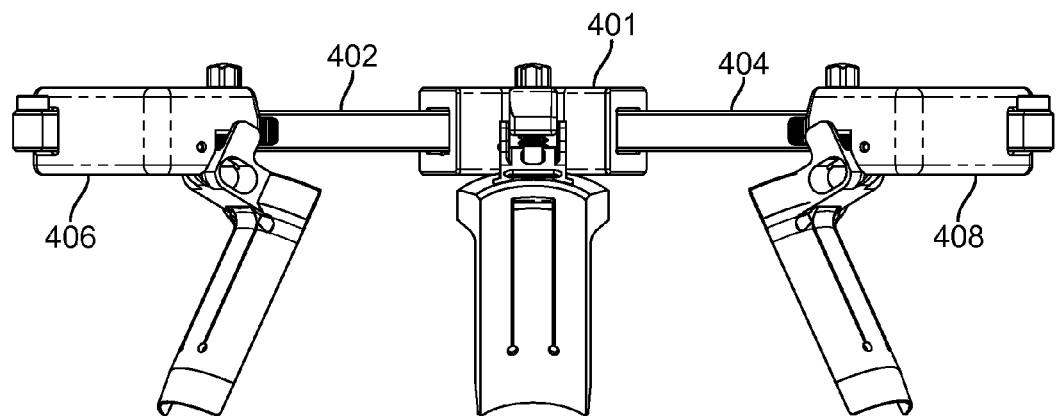
FIG. 43C is an end elevational view of the retractor of FIG. 42 with the sliders extended according to the present invention.
Figure 43D:
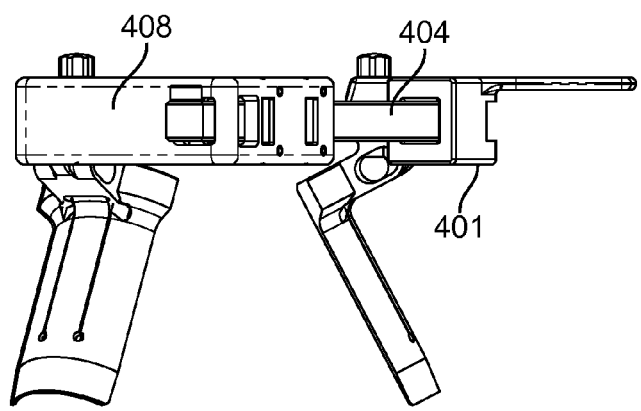
FIG. 43D is a side elevational view of the retractor of FIG. 42 with the sliders extended according to the present invention.

The first slider 406 includes a first rail receiving portion sized and configured to receive the first rail 40 in sliding engagement. The first slider 406 also includes bearing receiving portions configured to receive antifriction bearings 94 such that two bearings 94 are resident above and configured for contact with the top surface of the first rail 402 and two bearings 94 are resident below and configured for contact with the bottom surface of the first rail 402. Also, two bearings 94 are resident on one side and two bearings 94 are resident on the other side of the first rail 402 in the same manner as described above with the first, second, third, and fourth sliders 14, 16, 22, 24. The first slider 406 is also provided with a lock having a locking tooth configured for engagement with at least one recessed track 58 of the first rail 402. The first slider 406 is substantially U-shaped and the second slider 408 is also U-shaped and configured to be a mirror image of the first slider 406. Hence, the second slider 408 includes a second rail receiving portion configured to receive the second rail 404 therewith and with the same configuration of bearings 94 surrounding the second rail 404 including a lock and locking tooth as described above. Of course, the second rail 404 includes at least one recessed track 58 for engagement with the locking tooth. The first and second sliders 406, 408 each include a pivotably connected blade mount 92 of the like described above. The retractor 400 includes only three blades 266 such that each are configured to form a third of the circumference of the retractor zone defined by the closed orientation of the retractor 400. The U-shaped sliders 406, 408 are connect to their respective rails 402, 404 and extend away and return toward the rail housing 401 to provide blade mounts 92 for a close circular configuration of the blades 266. A slider instrument 306 is inserted into distraction apertures 312 to move the first slider 406 relative to the rail housing 401 and a second time to move the second slider 408 relative to the rail housing 401 to space apart the first and second sliders 406, 408 along the first and second rails 402, 404, respectively, from the orientation shown in FIGS. 42a-42b to the orientation shown in FIGS. 43a-43b. The retractor zone clearly visible in FIG. 43b is elongated in shape.

Figure 44:
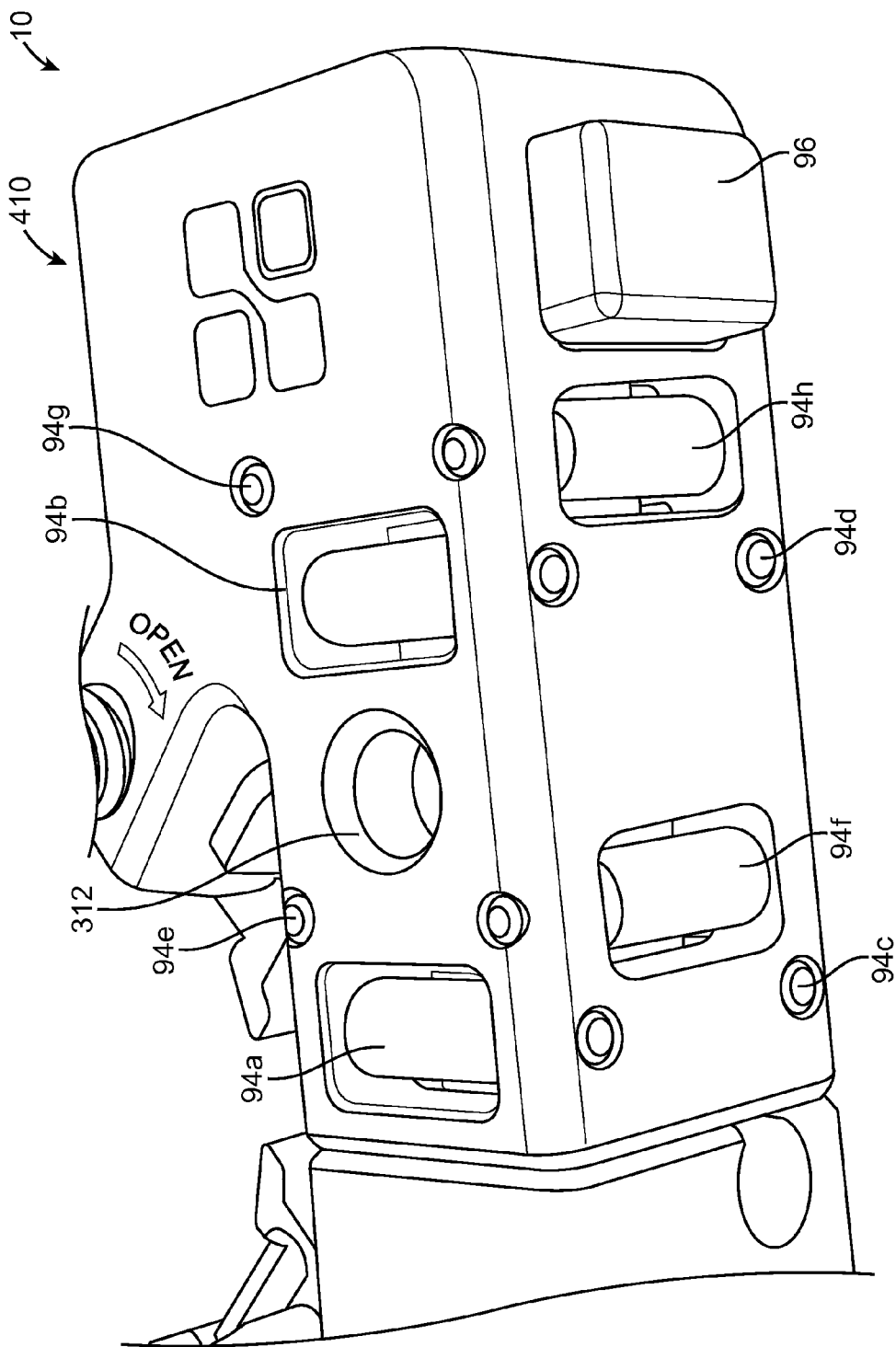
FIG. 44 is a top perspective section view of a retractor according to the present.

Turning now to FIG. 44, there is shown a top perspective view of a section of the retractor 10 illustrating the configuration of the antifriction bearings 94 in a slider relative to a rail. FIG. 44 shows two antifriction bearings 94a, 94b along the top surface of a rail. These two bearings 94a, 94b are located as far apart as possible inside the slider 410 to provide as much lateral stability and support to the rail as possible given the restraints provided by the lock 96. Two bearings 94c, 94d are positioned facing the bottom surface of the rail and are located directly beneath or aligned with the top two bearings 94a, 94b. In order to provide maximum stability, two vertical bearings 94e, 94f positioned alongside the rail are configured to be as close as possible to the horizontal bearings 94a, 94c and two vertical bearings 95g, 94h are positioned alongside the rail to be as close as possible to the horizontal bearings 94b, 94d. Each cylinder bearing of the plurality of bearings in the slider 410 have the same diameter and define a longitudinal axis about which each cylinder bearing is rotatable. The plurality of cylinder bearings in the slider 410 are arranged such that at least one cylinder bearing of the pair of cylinder bearings 94a, 94b that are adjacent to a first side of the rail are spaced from at least one cylinder bearing of the pair of cylinder bearings 94f, 94h that are adjacent to a second side of the first rail by a distance of not less than approximately one diameter as measured between their axes with the first side of the rail being adjacent to and intersecting with the second side of the rail. For example, the axis of bearing 94a is approximately one diameter away from the axis of bearings 94f and 94e. Since bearing 94a is directly inline with bearing 94c, bearing 94c is spaced apart from bearings 94e and 94f by a distance of approximately one diameter as measured from their axes.

The retractor 10 defines a retractor body that lies in a retractor plane with the retractor blades depending from the retractor plane. The blades are initially perpendicular to the retractor plane to provide the smallest size for insertion into a small incision. The blades can then be angled with respect to the plane to increase the tissue retraction. Generally, when a blade is moved relative to the rail or angled relative to the slider, it is moved against tissue and as such encounters opposing forces that torque the slider relative to the rail on which it is mounted. Because tissue, in particular, muscle can be very tough and offer much resistance to retraction forces exerted by the retractor, the torque on the slider relative to the rail can be very great. In prior art retractors, this torque resulted in sticktion or otherwise extreme pressure between the blade carrier and the rail and metal to metal contact of a typical rack and pinion construction. This invention successfully alleviates this undersirable trait of the prior art devices.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:
1. A surgical retractor, comprising:
a first rail and a second rail connected at an angle and defining a retractor plane; the first rail includes an outer surface and a plurality of teeth recessed with respect to the outer surface such that the plurality of teeth does not extend beyond the outer surface; the second rail includes an outer surface and a plurality of teeth recessed with respect to the outer surface such that the plurality of teeth of the second rail does not extend beyond the outer surface of the second rail;
a first slider configured to slide inwardly and outwardly along the first rail and carry a first blade at an angle to the retractor plane; the first slider including a first lock configured to arrest movement of the first slider in at least one direction relative to the first rail; the first slider including a plurality of bearings arranged about the outer surface of the first rail such that the plurality of bearings does not contact the plurality of teeth of the first rail;
a second slider configured to slide inwardly and outwardly along the second rail and carry a second blade at an angle to the retractor plane; the second slider including a second lock configured to arrest movement of the second slider in at least one direction relative to the second rail; the second slider including a plurality of bearings housed in the second slider and arranged about the outer surface of second rail such that the plurality of bearings does not contact the plurality of teeth of the second rail;
wherein the first rail includes four interconnected sides around a longitudinal axis; the plurality of bearings disposed in the first slider includes eight cylinder bearings configured such that a pair of cylinder bearings are located adjacent to each side of the first rail and spaced apart along the longitudinal axis; and
the second rail includes four interconnected sides around a longitudinal axis; the plurality of bearings disposed in the second slider includes eight cylinder bearings configured such that a pair of cylinder bearings are located adjacent to each side of the second rail and spaced apart along the longitudinal axis.

2. The surgical retractor of claim 1 wherein each cylinder bearing of the plurality of bearings in the first slider have a diameter and define a longitudinal axis about which each cylinder bearing is rotatable; the plurality of cylinder bearings in the first slider are configured such that at least one cylinder bearing of the pair of cylinder bearings that are adjacent to a first side of the first rail are spaced from at least one cylinder bearing of the pair of cylinder bearings that are adjacent to a second side of the first rail by a distance of not less than approximately one diameter as measured between their axes; the first side of the first rail being adjacent to and intersecting with the second side of the first rail; and each cylinder bearing of the plurality of bearings in the second slider have a diameter and define a longitudinal axis about which each cylinder bearing is rotatable; the plurality of cylinder bearings in the second slider are configured such that at least one cylinder bearing of the pair of cylinder bearings that are adjacent to a first side of the second rail are spaced from at least one cylinder bearing of the pair of cylinder bearings that are adjacent to a second side of the second rail by a distance of not less than approximately one diameter as measured between their axes; the first side of the second rail being adjacent to and intersecting with the second side of the second rail.

3. The surgical retractor of claim 2 wherein the plurality of cylinder bearings in the first slider are configured such that the pair of cylinder bearings that are adjacent to the first side of the first rail are positioned opposite from the pair of cylinder bearings that are adjacent to a third side of the first rail; the first and third sides of the first rail being parallel; and the pair of cylinder bearings that are adjacent to the second side of the first rail are positioned opposite from the pair of cylinder bearings that are adjacent to a fourth side of the first rail; the second and fourth sides of the first rail being parallel; and wherein the plurality of cylinder bearings in the second slider are configured such that the pair of cylinder bearings that are adjacent to the first side of the second rail are positioned opposite from the pair of cylinder bearings that are adjacent to a third side of the second rail; the first and third sides of the second rail being parallel; and the pair of cylinder bearings that are adjacent to the second side of the second rail are positioned opposite from the pair of cylinder bearings that are adjacent to a fourth side of the second rail; the second and fourth sides of the second rail being parallel.

4. The surgical retractor of claim 1 wherein the first lock is biased to engage the teeth of the first rail and releasable to permit movement in both directions along the first rail; and the second lock is biased to engage the teeth of the second rail and releasable to permit movement in both directions along the second rail.

5. The surgical retractor of claim 1 further including a third slider configured to slide inwardly and outwardly along the first rail and carry a third blade at an angle to the retractor plane; the third slider including a third lock configured to arrest movement of the third slider in at least one direction relative to the first rail; the third slider including a plurality of bearings arranged about the outer surface of the first rail such that the plurality of bearings does not contact the plurality of teeth of the first rail; and wherein the second rail is connected to the third slider.

6. The surgical retractor of claim 5 further including a third rail connected to the second slider; the third rail being in the retractor plane and angled with respect to the first rail; the third rail includes an outer surface and a plurality of teeth recessed with respect to the outer surface such that the plurality of teeth does not extend beyond the outer surface; and a fourth slider configured to slide inwardly and outwardly along the third rail and carry a fourth blade at an angle to the retractor plane; the fourth slider including a fourth lock configured to arrest movement of the fourth slider in at least one direction relative to the third rail; the fourth slider including a plurality of bearings arranged about the outer surface of the third rail such that the plurality of bearings does not contact the plurality of teeth of the third rail.

7. The surgical retractor of claim 6 wherein the plurality of bearings disposed in the third slider includes eight cylinder bearings configured such that a pair of spaced apart cylinder bearings are located adjacent to each side of the first rail;

the third rail includes four sides and the plurality of bearings disposed in the fourth slider includes eight cylinder bearings configured such that a pair of spaced apart cylinder bearings are located adjacent to each side of the third rail.

8. The surgical retractor of claim 6 wherein the fourth lock is biased to engage the teeth of the third track and releasable to permit movement in both directions along the third rail.

\* \* \* \* \*